US008697950B2

(12) United States Patent
Gaxiola et al.

(10) Patent No.: US 8,697,950 B2
(45) Date of Patent: *Apr. 15, 2014

(54) VACUOLAR PYROPHOSPHATASES AND USES IN PLANTS

(75) Inventors: Roberto A. Gaxiola, Tempe, AZ (US); Gerald R. Fink, Chestnut Hill, MA (US); Seth L. Alper, Boston, MA (US)

(73) Assignees: University of Connecticut, Farmington, CT (US); Whitehead Institute For Biomedical Research, Cambridge, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/890,795

(22) Filed: Aug. 7, 2007

(65) Prior Publication Data

US 2008/0104733 A1 May 1, 2008

Related U.S. Application Data

(63) Continuation-in-part of application No. 11/119,683, filed on May 2, 2005, which is a continuation of application No. 09/834,998, filed on Apr. 13, 2001, now abandoned, which is a continuation of application No. 09/644,039, filed on Aug. 22, 2000, now abandoned.

(60) Provisional application No. 60/164,808, filed on Nov. 10, 1999.

(51) Int. Cl.
*A01H 5/00* (2006.01)
*C12N 15/82* (2006.01)
*C12N 5/04* (2006.01)

(52) U.S. Cl.
USPC ........... 800/295; 800/298; 800/278; 800/289; 800/290; 435/419; 435/468

(58) Field of Classification Search
None
See application file for complete search history.

(56) References Cited

U.S. PATENT DOCUMENTS

| | | |
|---|---|---|
| 4,707,359 A | 11/1987 | McMullen |
| 4,945,050 A | 7/1990 | Sanford |
| 5,071,962 A | 12/1991 | Morrison |
| 5,100,792 A | 3/1992 | Sanford |
| 5,294,593 A | 3/1994 | Khan |
| 5,310,673 A | 5/1994 | Shibata |
| 5,451,240 A | 9/1995 | Trowbridge |
| 5,538,877 A | 7/1996 | Lundquist et al. |
| 5,750,862 A | 5/1998 | John |
| 5,837,545 A | 11/1998 | Guy et al. |
| 5,859,338 A | 1/1999 | Meyerowitz |
| 5,977,441 A | 11/1999 | Oliver |
| 6,063,731 A | 5/2000 | Back |
| 6,069,009 A | 5/2000 | Pepin |
| 6,087,175 A | 7/2000 | John |
| 6,087,176 A | 7/2000 | Durzan |
| 6,198,026 B1 | 3/2001 | Fabijanski |
| 6,200,808 B1 | 3/2001 | Simmonds |
| 6,239,327 B1 | 5/2001 | Grossniklaus |
| 6,248,935 B1 | 6/2001 | Cigan |
| 6,255,564 B1 | 7/2001 | Fabijanski |
| 6,936,750 B2 * | 8/2005 | Blumwald et al. ............ 800/298 |
| RE39,114 E | 5/2006 | Barry |
| 7,041,875 B1 | 5/2006 | Blumwald |
| 7,071,378 B1 | 7/2006 | Bonello |
| 7,071,382 B2 | 7/2006 | Cahoon |
| 7,534,933 B2 | 5/2009 | Gaxiola |
| 8,003,852 B2 | 8/2011 | Gaxiola et al. |
| 8,058,515 B2 | 11/2011 | Gaxiola et al. |
| 8,168,864 B2 | 5/2012 | Gaxiola et al. |
| 2002/0023282 A1 | 2/2002 | Gaxiola |
| 2002/0178464 A1 | 11/2002 | Gaxiola et al. |
| 2003/0213015 A1 | 11/2003 | Gaxiola |
| 2005/0262598 A1 | 11/2005 | Gaxiola |
| 2005/0278808 A1 | 12/2005 | Gaxiola |
| 2009/0288222 A1 | 11/2009 | Gaxiola et al. |

FOREIGN PATENT DOCUMENTS

| | | |
|---|---|---|
| WO | WO 97/26365 | 7/1997 |
| WO | WO 99/05902 | 2/1999 |
| WO | WO 99/47679 | 9/1999 |
| WO | WO 99/61616 | 12/1999 |
| WO | WO 00/75330 | 12/2000 |
| WO | WO 01/33945 | 5/2001 |
| WO | WO 01/45494 A2 | 6/2001 |
| WO | WO 02/15674 | 2/2002 |
| WO | WO 02/16558 | 2/2002 |
| WO | WO 02/072849 A2 | 9/2002 |

(Continued)

OTHER PUBLICATIONS

Gaxiola et al. (PNAS, 96:1480-1485, Published Feb. 16, 1999).*
Kay et al. (Science, 236:1299-1302, 1987).*
Bremberger et al. (Planta, 175:465-470, 1988).*
Nakamura et al. (Plant Cell Physiol., 33:139-149, 1992).*
Kim et al. (Plant Physiol., 106:375-382, 1994 ).*
Rausch et al. (J. Plant Physiol. 148:425-433, 1996).*
Barkla et al. (Annu. Rev. Plant Physiol. Plant Mol. Biol., 47:159-184, 1996).*
Kay et al (Science, 236:1299-1302, 1987).*
Li et al. (Science, 310:121-125, 2005.*

(Continued)

*Primary Examiner* — Vinod Kumar
(74) *Attorney, Agent, or Firm* — Hamilton, Brook, Smith & Reynolds, P.C.

(57) ABSTRACT

The present invention relates to a transgenic plant which is tolerant to a salt, comprising one or more plant cells transformed with exogenous nucleic acid which alters expression of vacuolar pyrophosphatase in the plant. The present invention also relates to a transgenic plant with increased Pi uptake, comprising one or more plant cells transformed with exogenous nucleic acid which alters expression of vacuolar pyrophosphatase in the plant. Also encompassed by the present invention are transgenic progeny and seeds of the transgenic plants described herein. Progeny transgenic plant grown from seed are also described.

37 Claims, 7 Drawing Sheets

(56) References Cited

FOREIGN PATENT DOCUMENTS

| WO | WO 2007/049275 A2 | 5/2007 |
|---|---|---|
| WO | WO 2007/053974 A1 | 5/2007 |
| WO | WO 2009/020528 | 2/2009 |

OTHER PUBLICATIONS

López-Bucio et al. (Plant Physiol., 129:244-256, 2002).*
Kochian et al. (Annu. Rev. Plant Biol., 55:459-493, 2004).*
Apse, M.P., et al., "Salt Tolerance Conferred by Overexpression of a Vacuolar Na+/H+ Antiport in *Arabidopsis*," *Science* 285: 1256-1258 (Aug. 20, 1999).
Gaxiola, R., et al., "A Novel and Conserved Salt-Induced Protein is an Important Determinant of Salt Tolerance in Yeast," *EMBO'J.* 11(9):3157-3164 (Sep. 1992).
Gaxiola, R.A., et al., "The Yeast CLC Chloride Channel Functions in Cation Homeostasis," *Proc. Natl. Acad. Sci. USA* 95(7):4046-4050 (Mar. 1998).
Gaxiola, R.A., et al., "The *Arabidosis thaliana* Proton Transporters, AtNhx1 and Avp1, Can Function in Cation Detoxification in Yeast," *Proc. Natl. Acad. Sci. USA* 96:1480-1485 (Feb. 1999).
Hechenberger, M., et al., "A Family of Putative Chloride Channels from *Arabidopsis* and Functional Complementation of a Yeast with a CLC Gene Disruption," *J Biol. Chem.* 271(52):33632-33638 (Dec. 27, 1996).
Nass, R., et al., "Novel Localization of a Na+/H+ Exchanger in a Late Endosomal Compartment of Yeast," *J. Biol. Chem.* 273(33):21054-21060 (Aug. 14, 1998).
Sato, M.H., et al., "The AtVAM3 Encodes a Syntaxin-Related Molecule Implicated in the Vacuolar Assembly in *Arabidopsis thaliana*," *J. Biol. Chem.* 272(39):24530-24535 (Sep. 26, 1997).
Stitt, M., "Pyrophosphate as an Energy Donor in the Cytosol of Plant Cells: an Enigmatic Alternative to ATP," *Bot. Acta* 111:167-175 (1998).
Xie, X.S., et al., "Isolation and Reconstruction of the Chloride Transporter of Clathrin-Coated Vesicles," *J. Biol. Chem.* 264(32):18870-18873 (Nov. 1989).
Topfer, R., et al., "A Set of Plant Expression Vectors for Transcriptional and Translational Fusions," *Nucleic Acid Res.* 15(14):5890 (Jul. 24, 1987).
Zhen, R.G., et al., "Acidic Residues Necessary for Pyrophosphate-Energized Pumping and Inhibition of the Vacuolar H+-pyrophosphatase by N,N'-Dicyclohexylcarbodiimide," *J. Biol. Chem.* 272(35):22340-22348 (Aug. 29, 1997).
Ballesteros, E., et al., "Na+/H+ antiport activity in tonoplast vesicles isolated from sunflower roots induced by NaCl stress," *Physiol. Plant.*, 99:328-334 (1997).
Gibeaut, D.M., et al., "Maximal Biomass of *Arabidopsis thaliana* Using a Simple, Low-Maintenance Hydroponic Method and Favorable Environmental Conditions," *Plant Physiol.* 115:317-319 (1997).
Kim, Y., et al., "Isolation and Characterization of cDNAs Encoding the Vacuolar H+ -Pyrophosphatase of *Beta vulgaris*," *Plant Physiol.*, 106:375-382 (1994).
Kirsch, M., et al., "Salt stress induces an increased expression of V-type H+-ATPase in mature sugar beet leaves," *Plant Mol. Biol.*, 32:543-547 (1996).
Neuhaus, J-M, and Rogers, J.C., "Sorting of proteins to vacuoles in plant cells," *Plant Mol. Biol.*, 38:127-144 (1998).
Paris, N., et al., "Molecular Cloning and Further Characterization of a Probable Plant Vacuolar Sorting Receptor," *Plant Physiol.*, 115:29-39 (1997).
Serrano, R., and Gaxiola, R., "Microbial Models and Salt Stress Tolerance in Plants," *Critical Reviews in Plant Sciences*, 13(2):121-138 (1994).
Stitt, M., "Pyrophosphate as an Energy Donor in the Cytosol of Plant Cells: an Enigmatic Alternative to ATP," *Bot. Acta.* 111:167-175 (1998).
Tsiantis, M.S., et al., "Salt regulation of transcript levels for the c subunit of a leaf vacuolar H+-ATPase in the halphyte *Mesembryanthemum crystallinum*," *The Plant Journal*, 9(5):729-736 (1996).
Vitale, A., and Raikhel, N.V., "What do proteins need to reach different vacuoles?," *Trends in Plant Science*, 4:148-154 (1999).
Zhen, R.G., et al., "Acidic Residues Necessary for Pyrophosphate-energized Pumping and Inhibition of the Vacuolar H+-pyrophosphatase by N,N'-Dicyclohexylcarbodiimide," *J. of Biol. Chem.*, 272(35):22340-22348 (1997).
Safafian, V., et al., "Molecular cloning and sequence of cDNA encoding the pyrophosphate-energized vacuolar membrane proton pump of *Arabidopsis thaliana*," *Proc. Natl. Acad. Sci. USA*, 89:1775-1779 (1992).
Lerchl, J., et al., "Molecular cloning, characterization and expression analysis of isoforms encoding tonoplast-bound proton-translocating inorganic pyrophosphatase in tobacco," *Plant Mol. Biol.*, 29:833-840 (1995).
Kim, E.J., et al., "Heterologous expression of plant vacuolar pyrophosphatase in yeast demonstrates sufficiency of the substrate-binding subunit for proton transport," *Proc. Natl. Acad. Sci. USA*, 91:6128-6132 (1994).
Schwappach, B., et al., "Golgi Localization and Functionally Important Domains in the $NH_2$ and COOH Terminus of the Yeast CLC Putative Chloride Channel Gef1p," *J. of Biol. Chem.*, 273(24):15110-15118 (1996).
Hong, B., et al., "Identification of a Calmodulin-Regulated $Ca^{2+}$-ATPase in Endoplasmic Reticulm," *Plant Physiology*, 119:1165-1175 (1999).
Burbidge, A., et al., "Structure and expression of a cDNA encoding a putative neoxanthin cleavage enzyme (NCE), isolated from a wilt-related tomato (*Lycopersicon esculentum* Mill.) Library," *J. of Exp. Botany*, 47(317):2111-2112 (1997).
Al-Awqati, Q., "Chloride channels of intracellular organelles," *Current Opinion in Cell Biology 1995*, 7:504-508.
Antebi, A. and Fink, G. R., "The Yeast $Ca^{2+}$-ATPase Homologue, PMR1, is Required for Normal Golgi Function and Localizes in a Novel Golgi-Like Distribution," *Mol. Biol. Cell*, 3:633-654, (1992).
Ballester, R., et al., "Genetic Analysis of Mammalian GAP Expressed in Yeast," *Cell*, 59:681-686, (1989).
Baltscheffsky, M., et al., "$H^+$-Proton-Pumping Inorganic Pyrophosphatase: A Tightly Membrane-Bound Family," *FEBS Letters*, 452:121-127, (1999).
Barkla, B.J., et al., "The Plant Vacuolar $Na^+/H^+$ Antiport," *Symp. Soc. Exp. Biol.*, 48:141-153, (1994).
Barkla, B.J., et al., "Tonoplast $Na^+/H^+$ Antiport Activity and Its Energization by the Vacuolar $H^+$-ATPase in the Halophytic Plant *Mesembryanthemum crystallinum* $L^1$," *Plant Physiol.*, 109:549-556, (1995).
Bassham, D.C. and Raikhel, N.V., "An *Arabidopsis* VPS45p Homolog Implicated in Protein Transport to the Vacuole," *Plant Physiol.*, 117:407-415, (1998).
Bechtold, N., et al., "In Planta *Agrobacterium* Mediated Gene Transfer by Infiltration of Adult *Arabidopsis* Plants," *C.R. Jances Acad. Sci. Ser. III Sci. Vie*, 361:1194-1199, (1993).
Becker, D., "Bynary Vectors Which Allow the Exchange of Plant Selectable Markers and Reporter Genes," *Nucleic Acids Research*, 18: pp. 203, (1990).
Bidonde, S., et al., "Expression and Characterization of Three Tomato 1-Aminocyclopropane-1-Carboxylate Oxidase cDNA in Yeast," *Eur. J. Biochem.*, 253:20-26, (1998).
Carystinos, G.D., et al. "Vacuolar $H^+$-Translocating Pyrophosphatase Is Induced by Anoxia or Chilling in Seedlings of Rice[1]," *Plant Physiol.*, 108:641-649, (1995).
Counillon, L., et al., "A Point Mutation of the $Na^+/H^+$ Exchanger Gene (NHE1) and Amplification of the Mutated Allele confer Amiloride Resistance Upon Chronic Acidosis," *Proc. Natl. Acad. Sci. USA*, 90:4508-4512, (1993).
Cunningham, S.D., and Ow., D.W., "Promises and Prospects of Phytoremediation," *Plant Physiol.*, 110:715-719, (1996).
Darley, C.P., et al., "Chill-Induced Changes in the Activity and Abundance of the Vacuolar Proton-Pumping Pyrophosphatase From Mung Bean Hypocotyls," *Plant Physiol.*, 109:659-665, (1995).
Davies, J.M., "The Bioenergetics of Vacuolar H+ Pumps," In: Leigh RA, Sanders D (eds) The Plant Vacuole, pp. 340-363. Academic Press, San Diego, (1997).

(56) References Cited

OTHER PUBLICATIONS

Davies, J. M., "Vacuolar Energization: Pumps, Shunts and Stress," *Journal of Experimental Botany*, 48(308):633-641, (1997).
Drews, G., et al., "In Situ Hybridization to RNA in Plant Tissue," *Plant Molec. Biol. Rep.*, 5:242-250, (1988).
Drozdowicz, Y.M., et al., "AVP2, a Sequence-Divergent, $K^+$-Insensitive $H^+$-Translocating Inorganic Pyrophosphatase from *Arabidopsis*," *Plant Physiol.*, 123:353-362, (2000).
Farré, E. M., et al., "Accceleration of Potato Tuber Sprouting by the Expression of a Bacterial Pyrophosphatase," *Nature Biotechnology*, 19: 268-272 (2001).
Galway, et al., "Growth and Ultrastructure of *Arabidopsis* Root Hairs: The rhd3 Mutation Alters Vacuole Enlargement and Tip Growth," *Planta*, 201:209-218, (1997).
Gaxiola, et al., "Drought-and-Salt-Tolerant Plants result From Overexpression of the AVP1 $H^+$-Pump," *PNAS*, 98(20):11444-11449, (2001).
Gietz, D., et al., "Improved Method for High Efficiency Transformation of Intact Yeast Cells," *Nucl. Acids Res.*, 20:p. 1425, (1992).
Gogarten, et al. "The Use of Antisence mRNA to Inhibit the Tonoplast $H^+$ATPase in Carrot," *The Plant Cell*, 4:851-864, (1992).
Guiltinan, M.J. and McHenry, L., "Epitope Tagging for the Detection of Fusion Protein Expression in Transfenic Plants," *Methods Cell Biol.*, 49:143-151, (1995).
Guo, H.H., et al., "Protein Tolerance to Random Amino Acid Change," *PNAS*, 101(25):9205-9210, (2004).
Gupta, et al. "Maintenance of Photosynthesis at Low Leaf Water Potential in Wheat,", *Plant Physiol.*, 89:1358-1365, (1989).
Hajdukiewicz, Z., et al. "The Small, Versatile pPZP Family of *Agrobacterium* Binary Vectors for Plant Transformation," *Plant Molecular biology*, 25:989-994, (1994).
Haughn, G.W. and Somerville, C., "Sulfonylurea-resistant Mutants of *Arabidopsis thaliana*," *Mol Gen Genet*, 204: 430-434 (1986).
Hill, M.A. and Preiss J., "Functional Analysis of Conserved Histidines in ADP-Glucose Pyrophosphorylase from *Escherichia coli*," *Biochemical and Biophysical Research Communications*, 244:573-577, (1998).
Hirschi, et al., "CAx1, an $H^+/Ca^{2+}$ Antiport From *Arabidopsis*," *Proc. Natl. Acad. Sci. USA*, 93:8782-8786, (1996).
Jauh, G.Y., et al., "Tonoplast Intrinsic Protein Isoforms as Markers for Vacuolar Functions," *The Plant Cell*, 11:1867-1882, (1999).
Kennedy, B.K., et al., "Redistribution of Silencing Proteins From Telomeres to the Nucleolus Is Associated With Extension of Life Span in *S. cerevisiae*," *Cell*, 89:381-391, (1997).
Kieber, J.J., et al., "CTR1, a Negative Regulator of the Ethylene Response Pathway in *Arabidopsis*, Encodes a Member of the Rat Family of Protein Kinases," *Cell*, 72:427-441, (1993).
Krysan, P.J., et al., "Identification of Transferred DNA Insertions Within *Arabidopsis* Genes Involved in Signal Transduction and Ion Transport," *Proc. Natl. Acad. Sci. USA*, 93:8145-8150, (1996).
Lazar, E., et al., "Transforming Growth Factor α: Mutation of Aspartic Acid 47 and Leucine 48 Results in Different Biological Activities," *Molecular and Cellular Biology*, 8(3):1247-1252, (1988).
Leigh, "Solute Composition of Vacuoles," *Advances in Botanical Research, The Plant Vacuole*, 25:171-194, (1997).
Levi, M., et al., "Rapid Immunofluorescent Determination of Cells in the S Phase in Pea Root Meristems: An Alternative to Autoradiography," *Physiologic Plantarum*, 71: 68-72, (1987).
Li, J., et al., "*Arabidopsis* $H^+$-PPase AVP1 Regulates Auxin-Mediated Organ Development," *Science*, 310:121-125, (2005).
Madhani, H.D., et al., "MAP Kinases with Distinct Inhibitory Functions Impart Signaling Specificity During Yeast Differentiation," *Cell*, 91:673-684, (1997).
Madrid, R., et al., "Ectopic Potassium Uptake in trk1 trk2 Mutants of *Saccharomyces cerevisiae* Correlates With a Highly Hyperpolarized Membrane Potential," *The Journal of Biological Chemistry*, 272(24):14838-14844, (1998).

Marty, F., "The Biogenesis of Vacuoles: Insights from Microscopy," In: Leight RA, Sanders D (eds) The Plant Vacuole, pp. 1-42. Academic Press, San Diego, (1997).
McCormick, S., "Transformation of tomato with *Agrobacterium tumerfaciens*," In: Lindsey, K. (ed) Plant Tissue Culture Manual, pp. 1-9. Kluwer Academic Publishers, Dordrecht, The Netherlands, (1991).
McCusker, J.H. et al., "Pleiotropic Plasma Membrane ATPase Mutations of *Saccharomyces cerevisiae*," *Molecular and Cellular Biology*, 7(11):4082-4088, (1987).
Mitsuda, N., et al., "Pollen-Specific Regulation of Vacuolar $H^+$-PPase Expression by Multiple *cis*-Acting Elements," *Plant Molecular Biology*, 46: 185-192 (2001).
Mullen, R.T., et al., "Identification of the Peroxisomal Targeting Signal for Cottonseed Catalase," *The Plant Journal*, 12(2):313-322, (1997).
Murguia, J.R., et al., "A Salt-Sensitive 3'('),5'-Bisphosphate Nucleotidase Involved in Sulfate Activation," *Science*, 267:232-234, (1995).
Nass, R., et al., "Intracellular Sequestration of Sodium by a Novel $Na^+/H^+$ Exchanger in Yeast is Enhanced by Mutations in the Plasma Membrane $H^+$-ATPase," *The Journal of Biological Chemistry*, 272(42):26145-26152, (1997).
Niyogi, K.K. and Fink, G.R., "Two Anthranilate Synthase Genes in *Arabidopsis*: Defense-Related Regulation of the Tryptophan Pathway," *The Plant Cell*, 4:721-733, (1992).
Park, S., et al., "Up-Regulation of a $H^+$-Pyrophosphatase ($H^+$-PPase) as a Strategy to Engineer Drought-Resistant Crop Plants," *PNAS 102* (52): 18830-18835 (2005).
Quesada, A., et al., "PCR-Identification of a *Nicotiana plymbaginifolia* cDNA Homologous to the High-Affinity Nitrate Transporters of the crnA Family," *Plant Molecular Biology*, 34:265-274, (1997).
Randall, S.K. and Sze, H., "Properties of the Partially Purified Tonoplast $H^+$-Pumping ATPase From Oat Roots," *The Journal of Biological Chemistry*, 261(3):1364-1371, (1986).
Rate, D.N., et al., "The Gain-of-Function *Arabidopsis* acd6 Mutant Reveals Novel Regulation and Function of the Salicylic Acid Signaling Pathway in Controlling Cell Death, Defenses, and Cell Growth," *The Plant Cell*, 11:1695-1708, (1999).
Rausch, et al., Salt Stress Responses of Higher Plants: The Role of Proton Pumps and $Na/H^+$-Antiporters, *Plant Physiol.*, 148:425-433, (1996).
Rea, P.A. and Turner, J.C., "Tonoplast Adenosine Triphosphatase and Inorganic Pyrophosphatase," *Method in Plant Biochemistry*, 3:385-405, (1990).
Rodriguez-Navarro, A. and Ramos, J., "Dual System for Potassium Transport in *Saccharomyces cerevisiae*," *Journal of Bacteriology*, 159(3):940-945, (1984).
Sandler, S.J., et al., "Inhibition of Gene Expression in Transformed Plants by Antisense RNA," *Plant Molecular Biology*, 11:301-310, (1988).
Schiefelbein, et al., Pollen Tube and Root-Hair Tip Growth is Disrupted in a Mutant of *Arabidopsis thaliana*, *Plant Physiol.*, 103:979-985, (1993).
Schneider, B.L., et al., "Use of Polymerase Chain Reaction Epitope Tagging for Protein Tagging in *Saccharomyces cerevisiae*," *Yeast*, 11(13):1265-1274, (1995).
Schumaker, K. S. and Sze, H., "A $Ca^{2+}/H^+$ Anitport System Driven by the Proton Electrochemical Gradient of a Tonoplast $H^+$-ATPase From Oat Roots," *Plant Physiol.*, 79: 1111-1117 (1985).
Sheveleva, E., et al., "Increased Salt and Drought Tolerance by D-Ononitol Production in Transgenic *Nicotiana tabacum* L.," *Plant Physiol.*, 115:1211-1219, (1997).
Sorin, A., et al., "PMR1, a $Ca^{2+}$-AtPase in Yeast Golgi, Has Properties Distinct From Sarco/Endoplasmic Reticulum and Plasma Membrane Calcium Pumps," *The Journal of Biological Chemistry*, 272(15):9895-9901, (1997).
Sugita, K., et al., "A Transformation Vector for the Production of Marker-Free Transgenic Plants Containing a Single Copy Transgene at High Frequency," *Plant Journal*, 22(5): 461-469 (2000).

(56) References Cited

OTHER PUBLICATIONS

Sze, et al. "Energization of Plant Cell Membranes by H+-Pumping ATPases: Regulation and Biosynthesis,", *The Plant Cell*, 11:677-689, (1999).
van der Krol, A.R., et al., "Inhibition of Flower Pigmentation by Antisense CHS Genes: Promoter and Minimal Sequence Requirements for the Antisense Effect," 14:457-466, (1990).
Wu, S.J., et al., "SOS1, A Genetic Locus Essential for Salt Tolerance and Potassium Acquisition," *The Plant Cell*, 8:617-627, (1996).
Zemo, D.A. and McCabem, J.T., "Transcriptional Responses of the Rat Vasopressin Gene to Acute and Repeated Acute Osmotic Stress," *Neuroscience Research*, 44:45-50, (2002).
Zhen, R.G., et al., "Aminomethylenediphosphonate: A Potent Type=Specific Inhibitor of Both Plant and Phototrophic Bacterial H+-Pyrophosphatases," *Plant Physiol.*, 104:153-159, (1994).
Zhen, R.G., et al., "Localization of Cytosolically Oriented Maleimide-Reactive Domain of Vacuolar H+-Pyrophosphatase," *The Journal of Biological Chemistry*, 269(37):23342-23350, (1994).
Zhen, R.G., et al., "The Molecular and Biochemical Basis of Pyrophosphate-Energized Proton Translocation at the Vacuolar Membrane," *Advances in Botanical Research, The Plant Vacuole*, 25:298-337, (1997).
Hung, S., et al., "Vacuolar H+-Pyrophosphatase cDNA (Accession No. U31467) from Etiolated Mung Bean Seedlings," Plant Gene Register PGR 95-082, *Plant Physiol.*, 109:1125-1127 (1995).
Ikeda, M., et al., "A Vacuolar H+-Pyrophosphatase in *Acetabularia acetabulum*: Molecular Cloning and Comparison with Higher Plants and a Bacterium," *J. of Exp. Botany*, 50(330):139-140 (1999).
Nakanishi, Y. et al., "Molecular Cloning and Sequencing of the cDNA for Vacuolar H+-Pyrophosphatase from *Chara corallina*," *Biochimica et Biophysica Acta*, 1418:245-250 (1999).
Sakakibara, Y. et al., "Identification of the Gene Structure and Promoter Region of H+-Translocating Inorganic Pyrophosphatase in Rice (*Oryza sativa* L.)," *Biochimica et Biophysica Acta*, 1444:117-124 (1999).
Sakakibara, Y. et al., "Isolation and Characterization of cDNAs encoding Vacuolar H+-Pyrophosphatase Isoforms From Rice (*Oryza sativa* L.)," *Plant Molecular Biol.*, 31:1029-1038 (1996).
Smart, L.B., et al., "Genes Involved in Osmoregulation During Turgor-Driven Cell Expansion of Developing Cotton Fibers Are Differentially Regulated," *Plant Physiol.*, 116:1539-1549 (1998).
Suzuki, Y., et al., "Molecular Cloning of Vacuolar H+-Pyrophosphatase and Its Expression During the Development of Pear Fruit," *Plant Cell Physiol.*, 40(8):900-904 (1999).
Tanaka, Y., et al., "Molecular Cloning of cDNA for Vacuolar Membrane Proton-Translocating Inorganic Pyrophosphatase in *Hordeum vulgare*," *Biochem & Biophys. Res. Comm.*, 190(3):1110-1114 (1993).
Barkla, B.J. and Pantoja, O., "Physiology of Ion Transport across the Tonoplast of Higher Plants," *Annu. Rev. Plant Physiol. Plant Mol. Biol.*, 47:159-184 (1996).
Kay, R., et al., "Duplication of CaMV 35S Promoter Sequences Creates a Strong Enhancer for Plant Genes," *Science*, 236:1299-1302 (1987).
Abdullah, R., et al., "Efficient Plant Regeneration From Rice Protoplasts Through Somatic Embryogenesis,"*Bio/Technology*, 4:1087-1090 (1986).
Abel, S., et al., "Phosphate Sensing in Higher Plants," *Physiol. Plant.*, 115:1-8 (2002).
Arango, M., et al., "The Plasma Membrane Proton Pump ATPase: The Significance of Gene Subfamilies," *Planta*, 216:355-365 (2003).
Bouche-Pillon, et al., "Immunolocalization of the Plasma Membrane H+-ATPase in Minor Veins of *Vicia faba* in Relation to Phloem Loading," *Plant Physiol.*, 105:691-697 (1994).
Cao, J., et al., "Regeneration of Herbicide Resistant Transgenic Rice Plant Following Microprojectilemediated Transformation of Suspension Culture Cells," *Plant Cell Rep.*, 11:589-591 (1992).
Clough, S.J. and Bent, A.F. "Floral Dip: A Simplified Method for *Agrobacterium*-Mediated Transformation of *Arabidopsis thaliana*," *Plant J.*, 16:735-743 (1998).

Drozdowicz, Y.M. and Rea, P.A., "Vacuolar H+-Pyrophosphatases: From Evolutionary Backwaters Into Mainstream," *Trends Plant Sci.*, 6(5):206-211 (2001).
Estelle, M. and Somerville, C., "Auxin-Resistant Mutants of *Arabidopsis thaliana* with an Altered Morphology," *Mol. Gen. Genet.*, 206:200-206 (1987).
Gahoonia, T.S. and Nielsen, N.E., "Root Traits as Tools for Creating Phosphorus Efficient Crop Varieties," *Plant Soil*, 260:47-57 (2004).
Gaxiola, R.A., et al., "Plant Proton Pumps," *FEBS Lett.*, 581:2204-2214 (2007).
Gillooly, J.F., et al., "The Metabolic Basis of Whole-Organism RNA and Phosphorus Content," *Proc. Natl. Acad. Sci. USA*, 102(33):11923-11927 (2005).
Hammond, J.P., et al., "Genetic Responses to Phosphorus Deficiency," *Ann. Bot.*, 94:323-332 (2004).
Hartel, H., et al., "DGD1-Independent Biosynthesis of Extraplastidic Galactolipids After Phosphate Deprivation in *Arabidopsis*?," *Proc. Natl. Acad. Sci. USA*, 97(19):10649-10654 (2000).
Hermans, C., et al., "How Do Plants Respond to Nutrient Shortage by Biomass Allocation?," *Trends Plant Sci.*, 11(12):610-617 (2006).
Holford, I.C.R., "Soil Phosphorus: Its Measurements and Its Uptake by Plants," *Aust. J. Soil Res.*, 35:227-239 (1997).
Kausch, A.P., et al., "Effects of Microprojectile Bombardment on Embryogenic Suspension Cell Cultures of Maize (*Zea mays* L.) Used for Genetic Transformation," *Planta*, 196:501-509 (1995).
Kochian, L., et al., "How Do Crop Plants Tolerate Acid Soils? Mechanisms of Aluminium Tolerance and Phosphorus Efficiency," *Annu. Rev. Plant Biol.*, 55:459-493 (2004).
Lopez-Bucio, et al., "Phosphate Availability Alters Architecture and Causes Changes in Hormone Sensitivity in the *Arabidopsis* Root System," *Plant Physiol.*, 129:244-256 (2002).
Maeshima, M., "Vacuolar H+-Pyrophosphatase," *Biochimica et Biophysica Acta*, 1465:37-51 (2000).
McSteen, P. and Leyser, O., "Shoot Branching," *Annu. Rev. Plant Biol.*, 56:353-374 (2005).
Misson, J., et al., "A Genome-Wide Transcriptional Analysis Using *Arabidopsis thaliana* Affymetrix Gene Chips Determined Plant Responses to Phosphate Deprivation," *PNAS*, 102(33):11934-11939 (2005).
Muchhal, U.S., et al., "Phosphate Transporters From the Higher Plant *Arabidopsis thaliana*," *Proc. Natl. Acad. Sci. USA*, 93:10519-10523 (1996).
Murashige, T. and Skoog, F., "A Revised Medium for Rapid Growth and Bioassays With Tobacco Tissue Culture," *Physiol. Plant.*, 15:473-497 (1962).
Murphy, A., Eisinger, et al., "Early Copper-Induced Leakage of K+ From *Arabidopsis* Seedlings is Mediated by Ion Channels and Coupled to Citrate Efflux," *Plant Physiol.*, 121:1375-1382 (1999).
Murphy, J. and Riley, J.P., "A Modified Single Solution Method for the Determination of Phosphate in Natural Waters," *Anal. Chico. Acta*, 27:31-36 (1962).
Raghothama, K.G., "Phosphate Acquisition," *Annu. Rev. Plant Physiol. Plant Mol. Biol.*, 50:665-693 (1999).
Rea, P.A., et al., "Vacuolar H(+)-Translocating Pyrophosphatases: A New Category of Ion Translocase," *Trends Biochem. Sci.*, 17:348-353 (1992).
Sanchez-Calderon, L., et al., "Characterization of Low Phosphorus Insensitive Mutants Reveals a Crosstalk Between Low Phosphorus-Induced Determinate Root Development and Activation of Genes Involved in the Adaptation of *Arabidopsis* to Phosphorus Deficiency," *Plant Physiol.*, 140: 879-889 (2006).
Shen, H., et al., "Root Plasma Membrane H+-Atpase is Involved in the Adaptation of Soybean to Phosphorus Starvation," *J. Exp. Bot.*, 57(6):1353-1362 (2006).
Vance, C.P., et al., "Phosphorus Acquisition and Use: Critical Adaptations by Plants for Securing a Nonrenewable Resource," *New Phytologist*, 157:423-447 (2003).
Ward, J., et al., "Dissociation and Reassembly of the Vacuolar H+-ATPase Complex From Oat Roots," *Plant Physiol.*, 99:161-169 (1992).
Xiang, C., et al., "A Mini Binary Vector Series for Plant Transformation," *Plant Mol. Biol.*, 40:711-717 (1999).

(56) References Cited

OTHER PUBLICATIONS

Yan, F., et al., "Adaptation of H+-Pumping and Plasma Membrane H+ ATPase Activity in Proteoid Roots of White Lupin Under Phosphate Deficiency," *Plant Physiol.*, 129:50-63 (2002).

Zhu, Y., et al., "A Link Between Citrate and Proton Release by Proteoid Roots of White Lupin (*Lupinus albus* L.) Grown Under Phosphorus-Deficient Conditions," *Plant Cell Physiol.*, 46(6):892-901 (2005).

Bremberger, C., et al., "Separation and purification of the tonoplast ATPase and pyrophosphatase from plants with constitutive and inducible *Crassulacean* acid metabolism", *Planta*, vol. 175, Springer-Verlag, pp. 465-470, 1988.

Nakamura, Yoshiyuki, et al., "Stimulation of the Extrusion of Protons and $H^+$-ATPase Activities with the Decline in Pyrophosphatase Activity of the Tonoplast in Intact Mung Bean Roots under High-NaCl Stress and Its Relation to External Levels of $Ca^{2+}$ Ions", *Plant Cell Physiol.*, vol. 33, No. 2, JSPP, pp. 139-149, 1992.

Brini, F., et al., "Cloning and Characterization of a Wheat Vacuolar Cation/Proton Antiporter and Pyrophosphatase Proton Pump," *Plant Physiology and Biochemistry*, 43(4): 347-354 (Apr. 2005).

Fink, G., et al., "Increased Size, Salt and Drought Tolerance in *A. thaliana* Overexpressing AVP1 Vacuolar H+- Pyrophosphatase," *Plant Biology*, vol. 2001 [online], (Jul. 2001). Retrieved from URL: <http://abstracts.aspb.org/pb2001/public/P32/0206.html> [retrieved on Oct. 7, 2008].

Gaxiola, R., et al., "Ectopic Overexpression in Tomato of the *Arabidopsis* AVP1 Gene Results in Drought Tolerance," *Plant Biology*, [online] (Jul. 2003). Retrieved from URL: <http://abstracts.aspb.org/pb2003/public/P33/0948.html> [retrieved on Oct. 7, 2008].

Sarafian, V., et al., "Radiation-Inactivation Analysis of Vacuolar Proton Atpase and Proton Pyrophosphatase From *Beta-vulgaris* L. Functional Sizes for Substrate Hydrolysis and for Proton Transport," *Biochemical Journal*, 283(2): 493-497 (1992)(Month of Publication—not available).

Zhang, J., et al., "Improving Drought Tolerance in *Medicago truncatula* Via Translational Genomics," *Plant Biology*, vol. 2007, [online] (Jul. 2007). Retrieved from URL: <http://abstracts.aspb.org/pb2007/public/P09/P09019.html> [retrieved on Oct. 7, 2008].

International Search Report for International Application No. PCT/US2008/009091 dated Oct. 30, 2008.

Notice of Allowance, U.S. Appl. No. 11/119,683, Dated: Sep. 15, 2011.

Yelenosky, G. and Guy, C.L., "Freezing Tolerance of Citrus, Spinach, and Petunia Leaf Tissue," *Plant Physiol.*, 89:444-451 (1989).

Canadian Office Action, Application No. 2,390,719, pp. 1-4, dated Mar. 27, 2012.

Canadian Office Action, Application No. 2,419,901, pp. 1-5, dated Mar. 26, 2012.

Edlund, A., et al., "Pollen and Stigma Structure and Function: The Role of Diversity in Pollination," *The Plant Cell*, vol. 16, S84-S97 (2004).

Canadian Office Action, Application No. 2,418,127, pp. 1-4, dated Apr. 13, 2012.

Altschul, S.F., et al., "Gapped BLAST and PSI-BLAST: A New Generation of Protein Database Search Programs," *Nucleic Acids Research*, 25(17):3389-3402, (1997).

Maruyama, C., et al., "Structural Studies of the Vacuolar H+-Pyrophosphatase: Sequence Analysis and Identification of the Residues Modified by Fluorescent Cyclohexylcarbodiimide and Maleimide," *Plant Cell Physiol.*, 39(10):1045-1053 (1998).

Meyerowitz, E.M., et al., "In Situ Hybridization to RNA in Plant Tissue," *Plant Molec. Biol. Rep.*, 5:242-250, (1987).

Nakanishi, Y. and Maeshima, M., "Molecular Cloning of Vacuolar H+-Pyrophosphatase and its Development Expression in Growing Hypocotyl of Mung Bean," *Plant Physiol.*, 116:589-597 (1998).

Notice of Abandonment, U.S. Appl. No. 09/934,088, mailed Jul. 27, 2005.

Office Action, U.S. Appl. No. 09/934,088, mailed Dec. 22, 2004.
Office Action, U.S. Appl. No. 09/934,088, mailed Sep. 24, 2003.
Office Action, U.S. Appl. No. 11/135,165, mailed Oct. 31, 2006.
Office Action, U.S. Appl. No. 11/135,165, mailed Jul. 25, 2007.
Office Action, U.S. Appl. No. 11/135,165, mailed Jun. 6, 2008.
Office Action, U.S. Appl. No. 11/135,165, mailed Oct. 22, 2009.
Final Office Action, U.S. Appl. No. 11/135,165, mailed Aug. 2, 2010.
Office Action, U.S. Appl. No. 11/135,165, mailed Feb. 28, 2011.
Office Action, U.S. Appl. No. 11/119,683, mailed Apr. 11, 2011.
Office Action—Pre Appeal Conf. Decision, U.S. Appl. No. 11/119,683, mailed Mar. 4, 2009.
Office Action—Pre Appeal Conf. Decision, U.S. Appl. No. 11/119,683, mailed Sep. 16, 2010.
Final Office Action, U.S. Appl. No. 11/119,683, mailed Mar. 16, 2010.
Office Action, U.S. Appl. No. 11/119,683, mailed Sep. 17, 2009.
Office Action, U.S. Appl. No. 11/119,683, mailed Jul. 18, 2008.
Office Action, U.S. Appl. No. 11/119,683, mailed Nov. 30, 2007.
Final Office Action, U.S. Appl. No. 11/119,683, mailed Jul. 10, 2007.
Office Action, U.S. Appl. No. 11/199,683, mailed Oct. 5, 2006.
Office Action( Res. Req), U.S. Appl. No. 11/119,683, mailed Jun. 14, 2006.
Office Action, U.S. Appl. No. 12/384,115, mailed Feb. 24, 2010.
Office Action, U.S. Appl. No. 12/384,115, mailed Sep. 16, 2010.
Notice of Allowance, U.S. Appl. No. 12/384,115, dated May 27, 2011.
Office Action, CA 2,419,901, dated Nov. 18, 2010.
Office Action, CA 2,419,901, dated Mar. 16, 2009.
Office Action, CA 2,390,719, dated Nov. 12, 2010.
Office Action, CA 2,390,719, dated Mar. 10, 2009.
Office Action, CA 2,418,127, dated Nov. 12, 2010.
Office Action, CA 2,418,127, dated Mar. 10, 2009.
Notice of Allowance, U.S. Appl. No. 10/344,658, Dated: Jan. 16, 2009.
Office Action—Advisory Action, U.S. Appl. No. 10/344,658, Dated: Dec. 9, 2008.
Office Action—Interview Summary, U.S. Appl. No. 10/344,658, Dated: Oct. 27, 2008.
Office Action, U.S. Appl. No. 10/344,658, Dated: Sep. 18, 2008.
Examiner-Initiated Interview Summary—Office Action, U.S. Appl. No. 10/344,658, Dated: Mar. 18, 2008.
Office Action Made Final, U.S. Appl. No. 10/344,658, Dated: Mar. 10, 2008.
Office Action, U.S. Appl. No. 10/344,658, Dated: Aug. 6, 2007.
Office Action, U.S. Appl. No. 10/344,658, Dated: Nov. 14, 2006.
Interview Summary—Office Action, U.S. Appl. No. 10/344,658, Dated: Aug. 1, 2006.
Office Action Made Final, U.S. Appl. No. 10/344,658, Dated: May 17, 2006.
Office Action, U.S. Appl. No. 10/344,658, Dated: Nov. 3, 2005.
International Search Report, PCT/US01/41806, completed Dec. 19, 2001.
International Preliminary Examination Report, PCT/US01/41806, completed Jun. 17, 2003.
Notification Concerning Transmittal of International Preliminary Report on Patentability with IPRP, PCT/US2008/009091, Mailed: Feb. 9, 2010, pp. 10.
International Search Report, PCT/US01/09548, mailed Jul. 31, 2001.
International Preliminary Examination Report (IPER), PCT/US01/09548, completed Aug. 1, 2003.
Final Office Action, U.S. Appl. No. 11/135,165, dated Oct. 13, 2011.
Notice of Allowance, for U.S. Appl. No. 11/135,165, dated Feb. 13, 2012.

\* cited by examiner

FIG. 2

```
-155   CTTAGATTTATCTTTGAGTCCCGAAACATCGAGGAACGCCTTCGAATCCCTCTCTCTCTGTGTGTGTTCTCTGTGTTCTCTCTCTCGCG    -67
 -66   CGAAGCGGTTCTCTTTCTTTTGTTTATTTGTTTTTATTTGTTTTTCTCTTATACGGAGGAGAGAAGATGGTGGCGCCTGCTTTGTTACCGGAG   27
                                                                  1-MetValAlaProAlaLeuLeuProGlu      9
  28   CTCTGGACGGAGATCCTTGTACCGATTTGTGCGGTGATTGGTATCGCCTTTTCGCTTTTCCAATGGTACGTTGTATCTCGCGTGAAACTCACC   120
  10   LeuTrpThrGluIleLeuValProIleCysAlaValIleGlyIleAlaPheSerLeuPheGlnTrpTyrValValSerArgValLysLeuThr    40
 121   TCTGACCTCGGCGCATCGTCTTCCGGTGGAGCTAACAATGGGAAGAATGGATACGGTGATTATCTAATCGAGGAAGAGGAAGGTGTTAATGAC   213
  41   SerAspLeuGlyAlaSerSerSerGlyGlyAlaAsnAsnGlyLysAsnGlyTyrGlyAspTyrLeuIleGluGluGluGluGlyValAsnAsp    71
 213   CAGAGTGTTGTCGCTAAGTGCGCTGAGATTCAGACTGCTATTTCCGAAGGTGCAACTTCATTCCTATTCACGGAGTACAAATATGTTGGTGTC   306
  72   GlnSerValValAlaLysCysAlaGluIleGlnThrAlaIleSerGluGlyAlaThrSerPheLeuPheThrGluTyrLysTyrValGlyVal   102
 307   TTCATGATTTTCTTTGCTGCTGTTATCTTTGTTTTCCTCGGCTCTGTTGAGGGATTCAGCACTGATAACAAGCCTTGTACTTACGACACCACC   399
 103   PheMetIlePhePheAlaAlaValIlePheValPheLeuGlySerValGluGlyPheSerThrAspAsnLysProCysThrTyrAspThrThr   133
 400   AGAACCTGCAAGCCTGCATTGGCTACTGCAGCTTTCAGTACCATTGCTTTCGTGCTTGGTGCTGTTACCTCTGTTCTATCTGGTTTCCTTGGG   492
 134   ArgThrCysLysProAlaLeuAlaThrAlaAlaPheSerThrIleAlaPheValLeuGlyAlaValThrSerValLeuSerGlyPheLeuGly   164
 493   ATGAAGATTGCTACATACGCTAATGCTAGGACCACTTTGGAGGCGAGGAAAGGTCTTGGAAAGGCGTTCATTGTTGCATTCAGGTCTGGTGCT   585
 165   MetLysIleAlaThrTyrAlaAsnAlaArgThrThrLeuGluAlaArgLysGlyValGlyLysAlaPheIleValAlaPheArgSerGlyAla   195
 586   CTGATGGGTTTCCTTCTTGCAGCGAGTGGTCTATTGGTGCTTTACATTACTATCAATGTGTTCAAGATCTATTACGGAGATGACTGGGAACGT   678
 196   ValMetGlyPheLeuLeuAlaAlaSerGlyLeuLeuValLeuTyrIleThrIleAsnValPheLysIleTyrTyrGlyAspAspTrpGluGly   226
 679   CTTTTTGAGGCTATTACTGGTTATGGTCTTGGTGGGTCTTCCATGGCTCTCTTTGGCCGTGTTGGTGGTGGGATCTACACTAAGGCTGCTGAT   771
 227   LeuPheGluAlaIleThrGlyTyrGlyLeuGlyGlySerSerMetAlaLeuPheGlyArgValGlyGlyGlyIleTyrThrLysAlaAlaAsp   257
 772   CTCGGCGCTGACCTTGTCGGTAAAATTGAGAGGAATATTCCAGAGGATGATCCAAGAAACCCAGCTGTCATTGCTGATAATGTCGGTGACAAT   864
 258   ValGlyAlaAspLeuValGlyLysIleGluArgAsnIleProGluAspAspProArgAsnProAlaValIleAlaAspAsnValGlyAspAsn   288
 865   GTTGGTGACATTGCTGGTATGGGATCTGATCTCTTTGGATCATATGCTGAAGCATCATGCGCTGCTCTTGTTGTTGCCTCGATCTCATCTTTC   957
 289   ValGlyAspIleAlaGlyMetGlySerAspLeuPheGlySerTyrAlaGluAlaSerCysAlaAlaLeuValValAlaSerIleSerSerPhe   319
 958   GGAATCAACCACGACTTCACTGCCATGTGCTACCCATTGCTCATCAGTTCAATGGGAATCTTGGTTTGTTTGATCACAACTCTCTTTGCCACT  1050
 320   GlyIleAsnHisAspPheThrAlaMetCysTyrProLeuLeuIleSerSerMetGlyIleLeuValCysLeuIleThrThrLeuPheAlaThr   350
1051   GACTTCTTTGAGATTAAGCTTGTCAAGGAGATTGAACCAGCATTGAAGAACCAGCTCATTATCTCAACTGTTATTATGACTGTTGCTATTCCT  1143
 351   AspPhePheGluIleLysLeuValLysGluIleGluProAlaLeuLysAsnGlnLeuIleIleSerThrValIleMetThrValGlyIleAla   381
1144   ATTGTGTCATGGGTTGGCTTACCGACCTCCTTTACCATCTTCAACTTTGGAACACAAAAAGTTGTCAAGAACTGGCAGCTATTCCTTTGTGTT  1236
 382   IleValSerTrpValGlyLeuProThrSerPheThrIlePheAsnPheGlyThrGlnLysValValLysAsnTrpGlnLeuPheLeuCysVal   412
1237   TGTGTTGGTCTTTGGGCTGGACTCATTATTGGTTTCGTCACTGAGTACTACACTAGTAACGCCTACAGCCCTGTGCAAGATGTTGCAGATTCA  1329
 413   CysValGlyLeuTrpAlaGlyLeuIleIleGlyPheValThrGluTyrTyrThrSerAsnAlaTyrSerProValGlnAspValAlaAspSer   443
1330   TGCAGAACTGGTGCAGCTACCAATGTTATCTTCGGCCTTGCTCTTGGTTACAAATCCGTCATTATTCCAATCTTTGCTATTGCTATCAGTATA  1422
 444   CysArgThrGlyAlaAlaThrAsnValIlePheGlyLeuAlaLeuGlyTyrLysSerValIleIleProIlePheAlaIleAlaIleSerIle   474
1423   TTCGTTAGCTTCAGCTTTGCTGCTATGTATGGTGTTGCTGTTGCTGCTCTTGGTATGCTCAGTACCATTGCCACTGGTTTGGCAATTGATGCT  1515
 475   PheValSerPheSerPheAlaAlaMetTyrGlyValAlaValAlaAlaLeuGlyMetLeuSerThrIleAlaThrGlyLeuAlaIleAspAla   505
1516   TATGGTCCCATCAGTGACAATGCTGGTGGTATTGCTGAAATGGCTGGAATGAGCCACCGCATCCGTGAAAGAACTGATGCTCTTGATGCCGCT  1608
 506   TyrGlyProIleSerAspAsnAlaGlyGlyIleAlaGluMetAlaGlyMetSerHisArgIleArgGluArgThrAspAlaLeuAspAlaAla   536
1609   GGAAACACCACTGCTGCTATTGGAAAGGGATTTGCCATTGGCTCTGCTGCCCTAGTCTCCTTGGCTCTCTTTGGTGCCTTTGTGAGCCGTGCA  1701
 537   GlyAsnThrThrAlaAlaIleGlyLysGlyPheAlaIleGlySerAlaAlaLeuValSerLeuAlaLeuPheGlyAlaPheValSerArgAla   567
1702   GGGATCCACACCGTAGATGTTTTGACCCCTAAAGTTATCATTGGGCTCCTTGTTGGTGCCATGCTTCCTTACTGGTTCTCTGCCATGACAATG  1794
 568   GlyIleHisThrValAspValLeuThrProLysValIleIleGlyLeuLeuValGlyAlaMetLeuProTyrTrpPheSerAlaMetThrMet   598
1795   AAGAGTGTGGGAAGTGCAGCTCTTAAGATGGTTGAAGAAGTTCGCAGGCAGTTCAACACCATCCCTGGACTTATGGAAGGAACCGCAAAACCA  1887
 599   LysSerValGlySerAlaAlaLeuLysMetValGluGluValArgArgGlnPheAsnThrIleProGlyLeuMetGluGlyThrAlaLysPro   629
1888   GACTACGCCACATGTGTCAAGATCTCCACCGATGCTTCCATCAAGGAAATGATACCTCCTGGTTGCCTTGTCATGCTCACACCTCTCATTGTT  1980
 630   AspTyrAlaThrCysValLysIleSerThrAspAlaSerIleLysGluMetIleProProGlyCysLeuValMetLeuThrProLeuIleVal   660
1981   GGTTTCTTCTTTGGAGTTGAGACCCTCTCTGGTGTCCTCGCCGGATCTCTTGTATCCGGTGTTCAGATCGCCATATCAGCATCTAACACTGGT  2073
 661   GlyPhePhePheGlyValGluThrLeuSerGlyValLeuAlaGlySerLeuValSerGlyValGlnIleAlaIleSerAlaSerAsnThrGly   691
2074   GGTCCCTGGGACAACGCCAAGAAATACATCGAGGCTGGTGTATCAGAGCACGCAAACAGCCTTGGACCAAAGGGTTCAGAGCCACACAAGGCA  2166
 692   GlyAlaTrpAspAsnAlaLysLysTyrIleGluAlaGlyValSerGluHisAlaAsnSerLeuGlyProLysGlySerGluProHisLysAla   722
2167   CCTCTCATTGGAGACACAATTGGAGACCCATTGAAGGATACTTCAGGACCTTCATTGAACATCCTCATCAAGCTCATGGCTGTTGAGTCTCTT  2259
 723   AlaValIleGlyAspThrIleGlyAspProLeuLysAspThrSerGlyProSerLeuAsnIleLeuIleLysLeuMetAlaValGluSerLeu   753
2260   GTCTTTGCTCCCTTCTTCGCCACTCACGGTGGTATCCTTTTCAAGTACTTCTAAACTCAATCCGAGGGAAGAAGATGACGATGATGAAGAAGA  2352
 754   ValPheAlaProPhePheAlaThrHisGlyIleLeuPheLysTyrPhe-  770
2353   AGAAGATGATGATGGCGATCGATTCTAAACTTTCTTTTTTACCATTCTTATTTTCGTTTACCGTAGGTGGTTAAAAAACCTTTTTGTTGATGA  2445
2446   GGCTCATTTAAAGAACCAACCAAATGATGTTTCTTTCTCTCACTCTCTGTCTTTCTGTTTTCTTTTTGTTCTGTTTAGAATTTAGAAATCCAC  2538
2539   CAAGTATTCGGTCGAGACTTGTTTTAGCCGTTACTTTCTGCTGCTTATATTTCCTAAATTGGTTGTCTTCTTCGAAACATAATTGGAATTTAT  2631
2632   TCTTACTGTTACTCTAAAAAAAAAAAA  2658
```

Figure 4

SEQUENCE LISTING

```
<160> NUMBER OF SEQ ID NOS: 21

<210> SEQ ID NO 1
<211> LENGTH: 538
<212> TYPE: PRT
<213> ORGANISM: Artificial Sequence
<220> FEATURE:
<223> OTHER INFORMATION: Arabidpsis - AtNhx1

<400> SEQUENCE: 1

Met Leu Asp Ser Leu Val Ser Lys Leu Pro Ser Leu Ser Thr Ser Asp
 1               5                  10                  15

His Ala Ser Val Val Ala Leu Asn Leu Phe Val Ala Leu Leu Cys Ala
             20                  25                  30

Cys Ile Val Leu Gly His Leu Leu Glu Glu Asn Arg Trp Met Asn Glu
         35                  40                  45

Ser Ile Thr Ala Leu Leu Ile Gly Leu Gly Thr Gly Val Thr Ile Leu
     50                  55                  60

Leu Ile Ser Lys Gly Lys Ser Ser His Leu Leu Val Phe Ser Glu Asp
 65                  70                  75                  80

Leu Phe Phe Ile Tyr Leu Leu Pro Pro Ile Ile Phe Asn Ala Gly Phe
                 85                  90                  95

Gln Val Lys Lys Lys Gln Phe Phe Arg Asn Phe Val Thr Ile Met Leu
            100                 105                 110

Phe Gly Ala Val Gly Thr Ile Ile Ser Cys Thr Ile Ile Ser Leu Gly
        115                 120                 125

Val Thr Gln Phe Phe Lys Lys Leu Asp Ile Gly Thr Phe Asp Leu Gly
    130                 135                 140

Asp Tyr Leu Ala Ile Gly Ala Ile Phe Ala Ala Thr Asp Ser Val Cys
145                 150                 155                 160

Thr Leu Gln Val Leu Asn Gln Asp Glu Thr Pro Leu Leu Tyr Ser Leu
                165                 170                 175

Val Phe Gly Glu Gly Val Val Asn Asp Ala Thr Ser Val Val Val Phe
            180                 185                 190

Asn Ala Ile Gln Ser Phe Asp Leu Thr His Leu Asn His Glu Ala Ala
        195                 200                 205

Phe His Leu Leu Gly Asn Phe Leu Tyr Leu Phe Leu Leu Ser Thr Leu
    210                 215                 220

Leu Gly Ala Ala Thr Gly Leu Ile Ser Ala Tyr Val Ile Lys Lys Leu
225                 230                 235                 240

Tyr Phe Gly Arg His Ser Thr Asp Arg Glu Val Ala Leu Met Met Leu
                245                 250                 255

Met Ala Tyr Leu Ser Tyr Met Leu Ala Glu Leu Phe Asp Leu Ser Gly
            260                 265                 270

Ile Leu Thr Val Phe Phe Cys Gly Ile Val Met Ser His Tyr Thr Trp
```

```
                275                 280                 285
His Asn Val Thr Glu Ser Ser Arg Ile Thr Thr Lys His Thr Phe Ala
    290                 295                 300

Thr Leu Ser Phe Leu Ala Glu Thr Phe Ile Phe Leu Tyr Val Gly Met
305                 310                 315                 320

Asp Ala Leu Asp Ile Asp Lys Trp Arg Ser Val Ser Asp Thr Pro Gly
                325                 330                 335

Thr Ser Ile Ala Val Ser Ser Ile Leu Met Gly Leu Val Met Val Gly
            340                 345                 350

Arg Ala Ala Phe Val Phe Pro Leu Ser Phe Leu Ser Asn Leu Ala Lys
        355                 360                 365

Lys Asn Gln Ser Glu Lys Ile Asn Phe Asn Met Gln Val Val Ile Trp
    370                 375                 380

Trp Ser Gly Leu Met Arg Gly Ala Val Ser Met Ala Leu Ala Tyr Asn
385                 390                 395                 400

Lys Phe Thr Arg Ala Gly His Thr Asp Val Arg Gly Asn Ala Ile Met
                405                 410                 415

Ile Thr Ser Thr Ile Thr Val Cys Leu Phe Ser Thr Val Val Phe Gly
            420                 425                 430

Met Leu Thr Lys Pro Leu Ile Ser Tyr Leu Leu Pro His Gln Asn Ala
        435                 440                 445

Thr Thr Ser Met Leu Ser Asp Asp Asn Thr Pro Lys Ser Ile His Ile
    450                 455                 460

Pro Leu Leu Asp Gln Asp Ser Phe Ile Glu Pro Ser Gly Asn His Asn
465                 470                 475                 480

Val Pro Arg Pro Asp Ser Ile Arg Gly Phe Leu Thr Arg Pro Thr Arg
                485                 490                 495

Thr Val His Tyr Tyr Trp Arg Gln Phe Asp Asp Ser Phe Met Arg Pro
            500                 505                 510

Val Phe Gly Gly Arg Gly Phe Val Pro Phe Val Pro Gly Ser Pro Thr
        515                 520                 525

Glu Arg Asn Pro Pro Asp Leu Ser Lys Ala
    530                 535

<210> SEQ ID NO 2
<211> LENGTH: 669
<212> TYPE: PRT
<213> ORGANISM: Artificial Sequence
<220> FEATURE:
<223> OTHER INFORMATION: Human - HsNhe-6

<400> SEQUENCE: 2

Met Ala Arg Arg Gly Trp Arg Arg Ala Pro Leu Arg Arg Gly Val Gly
1               5                   10                  15

Ser Ser Pro Arg Ala Arg Arg Leu Met Arg Pro Leu Trp Leu Leu Leu
            20                  25                  30

Ala Val Gly Val Phe Asp Trp Ala Gly Ala Ser Asp Gly Gly Gly Gly
        35                  40                  45

Glu Ala Arg Ala Met Asp Glu Glu Ile Val Ser Glu Lys Gln Ala Glu
    50                  55                  60

Glu Ser His Arg Gln Asp Ser Ala Asn Leu Leu Ile Phe Ile Leu Leu
65                  70                  75                  80

Leu Thr Leu Thr Ile Leu Thr Ile Trp Leu Phe Lys His Arg Arg Ala
                85                  90                  95

Arg Phe Leu His Glu Thr Gly Leu Ala Met Ile Tyr Gly Leu Leu Val
            100                 105                 110
```

```
Gly Leu Val Leu His Tyr Gly Ile His Val Pro Ser Asp Val Asn Asn
    115                 120                 125

Val Thr Leu Ser Cys Glu Val Gln Ser Ser Pro Thr Thr Leu Leu Val
    130                 135                 140

Thr Phe Asp Pro Glu Val Phe Phe Asn Ile Leu Leu Pro Pro Ile Ile
145                 150                 155                 160

Phe Tyr Ala Gly Tyr Ser Leu Lys Arg Arg His Phe Phe Arg Asn Leu
                165                 170                 175

Gly Ser Ile Leu Ala Tyr Ala Phe Leu Gly Thr Ala Ile Ser Cys Phe
                180                 185                 190

Val Ile Gly Ser Ile Met Tyr Gly Val Thr Leu Met Lys Val Thr
    195                 200                 205

Gly Gln Leu Ala Gly Asp Phe Tyr Phe Thr Asp Cys Leu Leu Phe Gly
    210                 215                 220

Ala Ile Val Ser Ala Thr Asp Pro Val Thr Val Leu Ala Ile Phe His
225                 230                 235                 240

Glu Leu Gln Val Asp Val Glu Leu Tyr Ala Leu Leu Phe Gly Glu Ser
                245                 250                 255

Val Leu Asn Asp Ala Val Ala Ile Val Leu Ser Ser Ser Ile Val Ala
                260                 265                 270

Tyr Gln Pro Ala Gly Asp Asn Ser His Thr Phe Asp Val Thr Ala Met
                275                 280                 285

Phe Lys Ser Ile Gly Ile Phe Leu Gly Ile Phe Ser Gly Ser Phe Ala
    290                 295                 300

Met Gly Ala Ala Thr Gly Val Val Thr Ala Leu Val Thr Lys Phe Thr
305                 310                 315                 320

Lys Leu Arg Glu Phe Gln Leu Leu Glu Thr Gly Leu Phe Phe Leu Met
                325                 330                 335

Ser Trp Ser Thr Phe Leu Leu Ala Glu Ala Trp Gly Phe Thr Gly Val
                340                 345                 350

Val Ala Val Leu Phe Cys Gly Ile Thr Gln Ala His Tyr Thr Tyr Asn
                355                 360                 365

Asn Leu Ser Thr Glu Ser Gln His Arg Thr Lys Gln Leu Phe Glu Leu
    370                 375                 380

Leu Asn Phe Leu Ala Glu Asn Phe Ile Phe Ser Tyr Met Gly Leu Thr
385                 390                 395                 400

Leu Phe Thr Phe Gln Asn His Val Phe Asn Pro Thr Phe Val Val Gly
                405                 410                 415

Ala Phe Val Ala Ile Phe Leu Gly Arg Ala Ala Asn Ile Tyr Pro Leu
                420                 425                 430

Ser Leu Leu Leu Asn Leu Gly Arg Arg Ser Lys Ile Gly Ser Asn Phe
                435                 440                 445

Gln His Met Met Met Phe Ala Gly Leu Arg Gly Ala Met Ala Phe Ala
    450                 455                 460

Leu Ala Ile Arg Asp Thr Ala Thr Tyr Ala Arg Gln Met Met Phe Ser
465                 470                 475                 480

Thr Thr Leu Leu Ile Val Phe Phe Thr Val Trp Val Phe Gly Gly Gly
                485                 490                 495

Thr Thr Ala Met Leu Ser Cys Leu His Ile Arg Val Gly Val Asp Ser
                500                 505                 510

Asp Gln Glu His Leu Gly Val Pro Glu Asn Glu Arg Arg Thr Thr Lys
    515                 520                 525

Ala Glu Ser Ala Trp Leu Phe Arg Met Trp Tyr Asn Phe Asp His Asn
```

```
                530             535             540
Tyr Leu Lys Pro Leu Leu Thr His Ser Gly Pro Pro Leu Thr Thr Thr
545                 550                 555                 560

Leu Pro Ala Cys Cys Gly Pro Ile Ala Arg Cys Leu Thr Ser Pro Gln
                565                 570                 575

Ala Tyr Glu Asn Gln Glu Gln Leu Lys Asp Asp Ser Asp Leu Ile
            580                 585                 590

Leu Asn Asp Gly Asp Ile Ser Leu Thr Tyr Gly Asp Ser Thr Val Asn
                595                 600                 605

Thr Glu Pro Ala Thr Ser Ser Ala Pro Arg Arg Phe Met Gly Asn Ser
        610                 615                 620

Ser Glu Asp Ala Leu Asp Arg Glu Leu Ala Phe Gly Asp His Glu Leu
625                 630                 635                 640

Val Ile Arg Gly Thr Arg Leu Val Leu Pro Met Asp Asp Ser Glu Pro
                645                 650                 655

Pro Leu Asn Leu Leu Asp Asn Thr Arg His Gly Pro Ala
                660                 665
```

<210> SEQ ID NO 3
<211> LENGTH: 633
<212> TYPE: PRT
<213> ORGANISM: Artificial Sequence
<220> FEATURE:
<223> OTHER INFORMATION: Yeast - ScNhx1

<400> SEQUENCE: 3

```
Met Leu Ser Lys Val Leu Leu Asn Ile Ala Phe Lys Val Leu Leu Thr
1               5                   10                  15

Thr Ala Lys Arg Ala Val Asp Pro Asp Asp Asp Glu Leu Leu Pro
            20                  25                  30

Ser Pro Asp Leu Pro Gly Ser Asp Pro Ile Ala Gly Asp Pro Asp
                35                  40                  45

Val Asp Leu Asn Pro Val Thr Glu Glu Met Phe Ser Ser Trp Ala Leu
50                  55                  60

Phe Ile Met Leu Leu Leu Ile Ser Ala Leu Trp Ser Ser Tyr Tyr
65                  70                  75                  80

Leu Thr Gln Lys Arg Ile Arg Ala Val His Glu Thr Val Leu Ser Ile
                85                  90                  95

Phe Tyr Gly Met Val Ile Gly Leu Ile Ile Arg Met Ser Pro Gly His
            100                 105                 110

Tyr Ile Gln Asp Thr Val Thr Phe Asn Ser Ser Tyr Phe Phe Asn Val
                115                 120                 125

Leu Leu Pro Pro Ile Ile Leu Asn Ser Gly Tyr Glu Leu Asn Gln Val
145                 150                 155                 160
```
Asn Phe Phe Asn Asn Met Leu Ser Ile Leu Ile Phe Ala Ile Pro Gly
145                 150                 155                 160

Thr Phe Ile Ser Ala Val Val Ile Gly Ile Ile Leu Tyr Ile Trp Thr
                165                 170                 175

Phe Leu Gly Leu Glu Ser Ile Asp Ile Ser Phe Ala Asp Ala Met Ser
            180                 185                 190

Val Gly Ala Thr Leu Ser Ala Thr Asp Pro Val Thr Ile Leu Ser Ile
                195                 200                 205

Phe Asn Ala Tyr Lys Val Asp Pro Lys Leu Tyr Thr Ile Ile Phe Gly
            210                 215                 220

Glu Ser Leu Leu Asn Asp Ala Ile Ser Ile Val Met Phe Glu Thr Cys
225                 230                 235                 240

-continued

```
Gln Lys Phe His Gly Gln Pro Ala Thr Phe Ser Ser Val Phe Glu Gly
                245                 250                 255

Ala Gly Leu Phe Leu Met Thr Phe Ser Val Ser Leu Leu Ile Gly Val
            260                 265                 270

Leu Ile Gly Ile Leu Val Ala Leu Leu Lys His Thr His Ile Arg
        275                 280                 285

Arg Tyr Pro Gln Ile Glu Ser Cys Leu Ile Leu Leu Ile Ala Tyr Glu
290                 295                 300

Ser Tyr Phe Phe Ser Asn Gly Cys His Met Ser Gly Ile Val Ser Leu
305                 310                 315                 320

Leu Phe Cys Gly Ile Thr Leu Lys His Tyr Ala Tyr Asn Met Ser
                325                 330                 335

Arg Arg Ser Gln Ile Thr Ile Lys Tyr Ile Phe Gln Leu Leu Ala Arg
                340                 345                 350

Leu Ser Glu Asn Phe Ile Phe Ile Tyr Leu Gly Leu Glu Leu Phe Thr
            355                 360                 365

Glu Val Glu Leu Val Tyr Lys Pro Leu Leu Ile Ile Val Ala Ala Ile
        370                 375                 380

Ser Ile Cys Val Ala Arg Trp Cys Ala Val Phe Pro Leu Ser Gln Phe
385                 390                 395                 400

Val Asn Trp Ile Tyr Arg Val Lys Thr Ile Arg Ser Met Ser Gly Ile
                405                 410                 415

Thr Gly Glu Asn Ile Ser Val Pro Asp Glu Ile Pro Tyr Asn Tyr Gln
            420                 425                 430

Met Met Thr Phe Trp Ala Gly Leu Arg Gly Ala Val Gly Val Ala Leu
        435                 440                 445

Ala Leu Gly Ile Gln Gly Glu Tyr Lys Phe Thr Leu Leu Ala Thr Val
    450                 455                 460

Leu Val Val Val Leu Thr Val Ile Ile Phe Gly Gly Thr Ala
465                 470                 475                 480

Gly Met Leu Glu Val Leu Asn Ile Lys Thr Gly Cys Ile Ser Glu Glu
                485                 490                 495

Asp Thr Ser Asp Asp Glu Phe Asp Ile Glu Ala Pro Arg Ala Ile Asn
            500                 505                 510

Leu Leu Asn Gly Ser Ser Ile Gln Thr Asp Leu Gly Pro Tyr Ser Asp
        515                 520                 525

Asn Asn Ser Pro Asp Ile Ser Ile Asp Gln Phe Ala Val Ser Ser Asn
    530                 535                 540

Lys Asn Leu Pro Asn Asn Ile Ser Thr Thr Gly Gly Asn Thr Phe Gly
545                 550                 555                 560

Gly Leu Asn Glu Thr Glu Asn Thr Ser Pro Asn Pro Ala Arg Ser Ser
                565                 570                 575

Met Asp Lys Arg Asn Leu Arg Asp Lys Leu Gly Thr Ile Phe Asn Ser
            580                 585                 590

Asp Ser Gln Trp Phe Gln Asn Phe Asp Glu Gln Val Leu Lys Pro Val
        595                 600                 605

Phe Leu Asp Asn Val Ser Pro Ser Leu Gln Asp Ser Ala Thr Gln Ser
    610                 615                 620

Pro Ala Asp Phe Ser Ser Gln Asn His
625                 630

<210> SEQ ID NO 4
<211> LENGTH: 11
<212> TYPE: PRT
```

-continued

```
<213> ORGANISM: Unknown
<220> FEATURE:
<223> OTHER INFORMATION: Putative Amiloride Binding Site From Human Nhe1

<400> SEQUENCE: 4

Asp Val Phe Phe Leu Phe Leu Leu Pro Pro Ile
 1               5                  10

<210> SEQ ID NO 5
<211> LENGTH: 38
<212> TYPE: DNA
<213> ORGANISM: Artificial Sequence
<220> FEATURE:
<223> OTHER INFORMATION: PCR primer used to amplify AtNHX1 ORF

<400> SEQUENCE: 5
ggcccgggat ggattctcta gtgtcgaaac tgccttcg                                38

<210> SEQ ID NO 6
<211> LENGTH: 2813
<212> TYPE: DNA
<213> ORGANISM: Arabidopsis thaliana
<220> FEATURE:
<223> OTHER INFORMATION: Arabidopsis thaliana

<400> SEQUENCE: 6
cttagattta tctttgagtc ccgaaacatc gaggaacgcc ttcgaatccc tctctctctg        60
tgtgtgttct ctgtgttctc tctctcgcgc gaagcggttc tctttctttt gtttatttgt       120
ttttatttgt ttttctctta tacggaggag agaagatggt ggcgcctgct tgttaccgg         180 agctctggac ggagatcctt gtaccgattt gtgcggtgat tggtatcgcc ttttcgcttt       240
tccaatggta cgttgtatct cgcgtgaaac tcacctctga cctcggcgca tcgtcttccg       300
gtggagctaa caatgggaag aatggatacg gtgattatct aatcgaggaa gaggaaggtg       360
ttaatgacca gagtgttgtc gctaagtgcg ctgagattca gactgctatt ccgaaggtg        420 caacttcatt cctattcacg gagtacaaat atgttggtgt cttcatgatt ttctttgctg       480
ctgttatctt tgttttcctc ggctctgttg agggattcag cactgataac aagccttgta       540
cttacgacac caccagaacc tgcaagcctg cattggctac tgcagctttc agtaccattg       600
ctttcgtgct tggtgctgtt acctctgttc tatctggttt ccttgggatg aagattgcta       660
catacgctaa tgctaggacc actttggagg cgaggaaagg tgttggaaag gcgttcattg       720
ttgcattcag gtctggtgct gtgatgggtt tccttcttgc agcgagtggt ctattggtgc       780
tttacattac tatcaatgtg ttcaagatct attacgagag tgactgggaa ggtctttttg       840
aggctattac tggttatggt cttggtgggt cttccatggc tctctttggc cgtgttggtg       900
gtgggatcta cactaaggct gctgatgtcg gcgctgacct tgtcggtaaa attgagagga       960
atattccaga ggatgatcca agaaacccag ctgtcattgc tgataatgtc ggtgacaatg      1020
ttggtgacat tgctggtatg ggatctgatc tctttggatc atatgctgaa gcatcatgcg      1080
ctgctcttgt tgttgcctcg atctcatctt tcggaatcaa ccacgacttc actgccatgt      1140
gctacccatt gctcatcagt tcaatgggaa tcttggtttg tttgatcaca actctctttg      1200
ccactgactt ctttgagatt aagcttgtca aggagattga accagcattg aagaaccagc      1260
tcattatctc aactgttatt atgactgttg gtattgctat tgtgtcatgg ttggcttac       1320 cgacctcctt taccatcttc aactttggaa cacaaaaagt tgtcaagaac tggcagctat      1380
tccttttgtg ttgtgttggt cttgggctg actcattat tggtttcgtc actgagtact       1440
acactagtaa cgcctacagc cctgtgcaag atgttgcaga ttcatgcaga actggtgcag      1500
```

-continued

```
ctaccaatgt tatcttcggc cttgctcttg gttacaaatc cgtcattatt ccaatctttg   1560
ctattgctat cagtatattc gttagcttca gctttgctgc tatgtatggt gttgctgttg   1620
ctgctcttgg tatgctcagt accattgcca ctggtttggc aattgatgct tatggtccca   1680
tcagtgacaa tgctggtggt attgctgaaa tggctggaat gagccaccgc atccgtgaaa   1740
gaactgatgc tcttgatgcc gctggaaaca ccactgctgc tattggaaag ggatttgcca   1800
ttggctctgc tgccctagtc tccttggctc tctttggtgc ctttgtgagc cgtgcaggga   1860
tccacaccgt agatgttttg acccctaaag ttatcattgg gctccttgtt ggtgccatgc   1920
ttccttactg gttctctgcc atgacaatga agagtgtggg aagtgcagct cttaagatgg   1980
ttgaagaagt tcgcaggcag ttcaacacca tccctggact tatggaagga accgcaaaac   2040
cagactacgc cacatgtgtc aagatctcca ccgatgcttc catcaaggaa atgataccctc  2100 ctggttgcct tgtcatgctc acacctctca ttgttggttt cttctttgga gttgagaccc   2160
tctctggtgt cctcgccgga tctcttgtat ccggtgttca gatcgccata tcagcatcta   2220
acactggtgg tgcctgggac aacgccaaga aatacatcga ggctggtgta tcagagcacg   2280
caaagagcct tggaccaaag ggttcagagc acacaaggc agctgtgatt ggagacacaa    2340
ttggagaccc attgaaggat acttcaggac cttcattgaa catcctcatc aagctcatgg   2400
ctgttgagtc tcttgtcttt gctcccttct tcgccactca cggtggtatc cttttcaagt   2460
acttctaaac tcaatccgag ggaagaagat gacgatgatg aagaagaaga agatgatgat   2520
ggcgatcgat tctaaacttt ctttttttacc attcttattt tcgtttaccg taggtggtta   2580 aaaaacctttt tgttgatga ggctcattta agaaccaac caatgatgt ttctttctct     2640 cactctctgt ctttctgttt tctttttgtt ctgtttagaa tttagaaatc caccaagtat   2700
tcggtcgaga cttgttttag ccgttacttt ctgctgctta tatttcctaa attggttgtc   2760
ttcttcgaaa cataattgga atttattgtt actgttagtc taaaaaaaaa aaa           2813
```

<210> SEQ ID NO 7
<211> LENGTH: 770
<212> TYPE: PRT
<213> ORGANISM: Arabidopsis thaliana
<220> FEATURE:
<223> OTHER INFORMATION: Arabidopsis thaliana

<400> SEQUENCE: 7

```
Met Val Ala Pro Ala Leu Leu Pro Glu Leu Trp Thr Glu Ile Leu Val
 1               5                  10                  15

Pro Ile Cys Ala Val Ile Gly Ile Ala Phe Ser Leu Phe Gln Trp Tyr
                20                  25                  30

Val Val Ser Arg Val Lys Leu Thr Ser Asp Leu Gly Ala Ser Ser Ser
            35                  40                  45

Gly Gly Ala Asn Asn Gly Lys Asn Gly Tyr Gly Asp Tyr Leu Ile Glu
        50                  55                  60

Glu Glu Glu Gly Val Asn Asp Gln Ser Val Val Ala Lys Cys Ala Glu
     65                  70                  75                  80

Ile Gln Thr Ala Ile Ser Glu Gly Ala Thr Ser Phe Leu Phe Thr Glu
                 85                  90                  95

Tyr Lys Tyr Val Gly Val Phe Met Ile Phe Phe Ala Ala Val Ile Phe
                100                 105                 110

Val Phe Leu Gly Ser Val Glu Gly Phe Ser Thr Asp Asn Lys Pro Cys
            115                 120                 125

Thr Tyr Asp Thr Thr Arg Thr Cys Lys Pro Ala Leu Ala Thr Ala Ala
```

-continued

```
             130                 135                 140
Phe Ser Thr Ile Ala Phe Val Leu Gly Ala Val Thr Ser Val Leu Ser
145                 150                 155                 160

Gly Phe Leu Gly Met Lys Ile Ala Thr Tyr Ala Asn Ala Arg Thr Thr
                165                 170                 175

Leu Glu Ala Arg Lys Gly Val Gly Lys Ala Phe Ile Val Ala Phe Arg
            180                 185                 190

Ser Gly Ala Val Met Gly Phe Leu Leu Ala Ala Ser Gly Leu Leu Val
        195                 200                 205

Leu Tyr Ile Thr Ile Asn Val Phe Lys Ile Tyr Tyr Gly Asp Asp Trp
    210                 215                 220

Glu Gly Leu Phe Glu Ala Ile Thr Gly Tyr Gly Leu Gly Gly Ser Ser
225                 230                 235                 240

Met Ala Leu Phe Gly Arg Val Gly Gly Ile Tyr Thr Lys Ala Ala
                245                 250                 255

Asp Val Gly Ala Asp Leu Val Gly Lys Ile Glu Arg Asn Ile Pro Glu
            260                 265                 270

Asp Asp Pro Arg Asn Pro Ala Val Ile Ala Asp Asn Val Gly Asp Asn
        275                 280                 285

Val Gly Asp Ile Ala Gly Met Gly Ser Asp Leu Phe Gly Ser Tyr Ala
    290                 295                 300

Glu Ala Ser Cys Ala Ala Leu Val Val Ala Ser Ile Ser Ser Phe Gly
305                 310                 315                 320

Ile Asn His Asp Phe Thr Ala Met Cys Tyr Pro Leu Leu Ile Ser Ser
                325                 330                 335

Met Gly Ile Leu Val Cys Leu Ile Thr Thr Leu Phe Ala Thr Asp Phe
            340                 345                 350

Phe Glu Ile Lys Leu Val Lys Glu Ile Glu Pro Ala Leu Lys Asn Gln
        355                 360                 365

Leu Ile Ile Ser Thr Val Ile Met Thr Val Gly Ile Ala Ile Val Ser
    370                 375                 380

Trp Val Gly Leu Pro Thr Ser Phe Thr Ile Phe Asn Phe Gly Thr Gln
385                 390                 395                 400

Lys Val Val Lys Asn Trp Gln Leu Phe Leu Cys Val Cys Val Gly Leu
                405                 410                 415

Trp Ala Gly Leu Ile Ile Gly Phe Val Thr Glu Tyr Tyr Thr Ser Asn
            420                 425                 430

Ala Tyr Ser Pro Val Gln Asp Val Ala Asp Ser Cys Arg Thr Gly Ala
        435                 440                 445

Ala Thr Asn Val Ile Phe Gly Leu Ala Leu Gly Tyr Lys Ser Val Ile
    450                 455                 460

Ile Pro Ile Phe Ala Ile Ala Ile Ser Ile Phe Val Ser Phe Ser Phe
465                 470                 475                 480

Ala Ala Met Tyr Gly Val Ala Val Ala Ala Leu Gly Met Leu Ser Thr
                485                 490                 495

Ile Ala Thr Gly Leu Ala Ile Asp Ala Tyr Gly Pro Ile Ser Asp Asn
            500                 505                 510

Ala Gly Gly Ile Ala Glu Met Ala Gly Met Ser His Arg Ile Arg Glu
        515                 520                 525

Arg Thr Asp Ala Leu Asp Ala Ala Gly Asn Thr Thr Ala Ala Ile Gly
    530                 535                 540

Lys Gly Phe Ala Ile Gly Ser Ala Ala Leu Val Ser Leu Ala Leu Phe
545                 550                 555                 560
```

```
Gly Ala Phe Val Ser Arg Ala Gly Ile His Thr Val Asp Val Leu Thr
            565                 570                 575

Pro Lys Val Ile Ile Gly Leu Leu Val Gly Ala Met Leu Pro Tyr Trp
        580                 585                 590

Phe Ser Ala Met Thr Met Lys Ser Val Gly Ser Ala Ala Leu Lys Met
    595                 600                 605

Val Glu Glu Val Arg Arg Gln Phe Asn Thr Ile Pro Gly Leu Met Glu
610                 615                 620

Gly Thr Ala Lys Pro Asp Tyr Ala Thr Cys Val Lys Ile Ser Thr Asp
625                 630                 635                 640

Ala Ser Ile Lys Glu Met Ile Pro Pro Gly Cys Leu Val Met Leu Thr
                645                 650                 655

Pro Leu Ile Val Gly Phe Phe Phe Gly Val Glu Thr Leu Ser Gly Val
            660                 665                 670

Leu Ala Gly Ser Leu Val Ser Gly Val Gln Ile Ala Ile Ser Ala Ser
        675                 680                 685

Asn Thr Gly Gly Ala Trp Asp Asn Ala Lys Lys Tyr Ile Glu Ala Gly
    690                 695                 700

Val Ser Glu His Ala Lys Ser Leu Gly Pro Lys Gly Ser Glu Pro His
705                 710                 715                 720

Lys Ala Ala Val Ile Gly Asp Thr Ile Gly Asp Pro Leu Lys Asp Thr
                725                 730                 735

Ser Gly Pro Ser Leu Asn Ile Leu Ile Lys Leu Met Ala Val Glu Ser
            740                 745                 750

Leu Val Phe Ala Pro Phe Phe Ala Thr His Gly Gly Ile Leu Phe Lys
        755                 760                 765

Tyr Phe
    770

<210> SEQ ID NO 8
<211> LENGTH: 17
<212> TYPE: DNA
<213> ORGANISM: Artificial Sequence
<220> FEATURE:
<223> OTHER INFORMATION: PCR primer used to amplify ACT2

<400> SEQUENCE: 8
cccgctatgt atgtcgc                                                    17

<210> SEQ ID NO 9
<211> LENGTH: 18
<212> TYPE: DNA
<213> ORGANISM: Artificial Sequence
<220> FEATURE:
<223> OTHER INFORMATION: PCR primer used to amplify ACT2

<400> SEQUENCE: 9
tccagcaagg tcaagacg                                                   18

<210> SEQ ID NO 10
<211> LENGTH: 21
<212> TYPE: DNA
<213> ORGANISM: Artificial Sequence
<220> FEATURE:
<223> OTHER INFORMATION: PCR primer used to amplify AtPT1

<400> SEQUENCE: 10
cctcctcaag ttgactacat t                                               21

<210> SEQ ID NO 11
```

```
<211> LENGTH: 23
<212> TYPE: DNA
<213> ORGANISM: Artificial Sequence
<220> FEATURE:
<223> OTHER INFORMATION: PCR primer used to amplify AtPT1

<400> SEQUENCE: 11
ctcgatatct gtttgtaaga cct                                              23

<210> SEQ ID NO 12
<211> LENGTH: 22
<212> TYPE: DNA
<213> ORGANISM: Artificial Sequence
<220> FEATURE:
<223> OTHER INFORMATION: PCR primer used to amplify AVP1

<400> SEQUENCE: 12
gtttcgtcac tgagtactac ac                                               22

<210> SEQ ID NO 13
<211> LENGTH: 26
<212> TYPE: DNA
<213> ORGANISM: Artificial Sequence
<220> FEATURE:
<223> OTHER INFORMATION: PCR primer used to amplify AVP1

<400> SEQUENCE: 13
tcatgatagc aatagcaaag attgga                                           26

<210> SEQ ID NO 14
<211> LENGTH: 19
<212> TYPE: DNA
<213> ORGANISM: Artificial Sequence
<220> FEATURE:
<223> OTHER INFORMATION: PCR primer used to amplify AHA1

<400> SEQUENCE: 14
tccatccctg ttgaggagt                                                   19

<210> SEQ ID NO 15
<211> LENGTH: 22
<212> TYPE: DNA
<213> ORGANISM: Artificial Sequence
<220> FEATURE:
<223> OTHER INFORMATION: PCR primer used to amplify AHA1

<400> SEQUENCE: 15
atatctgctt tcttcaaagc gg                                               22

<210> SEQ ID NO 16
<211> LENGTH: 18
<212> TYPE: DNA
<213> ORGANISM: Artificial Sequence
<220> FEATURE:
<223> OTHER INFORMATION: PCR primer used to amplify AHA2

<400> SEQUENCE: 16
attgacggca gtggtaac                                                    18

<210> SEQ ID NO 17
<211> LENGTH: 17
<212> TYPE: DNA
<213> ORGANISM: Artificial Sequence
<220> FEATURE:
<223> OTHER INFORMATION: PCR primer used to amplify AHA2

<400> SEQUENCE: 17
```

-continued

```
cgagcaacag ccaacga                                              17

<210> SEQ ID NO 18
<211> LENGTH: 25
<212> TYPE: DNA
<213> ORGANISM: Artificial Sequence
<220> FEATURE:
<223> OTHER INFORMATION: PCR primer used to amplify AHA6

<400> SEQUENCE: 18
agatgagata attgacaagt ttgct                                     25

<210> SEQ ID NO 19
<211> LENGTH: 21
<212> TYPE: DNA
<213> ORGANISM: Artificial Sequence
<220> FEATURE:
<223> OTHER INFORMATION: PCR primer used to amplify AHA6

<400> SEQUENCE: 19
tctgcactgt catgtcttgg a                                         21

<210> SEQ ID NO 20
<211> LENGTH: 30
<212> TYPE: DNA
<213> ORGANISM: Artificial Sequence
<220> FEATURE:
<223> OTHER INFORMATION: PCR primer used to amplify AVP1 promoter

<400> SEQUENCE: 20
gctctagacg tttaccacac cagtcaccac                                30

<210> SEQ ID NO 21
<211> LENGTH: 30
<212> TYPE: DNA
<213> ORGANISM: Artificial Sequence
<220> FEATURE:
<223> OTHER INFORMATION: PCR primer used to amplify AVP1 promoter

<400> SEQUENCE: 21
cgggatccct tctctcctcc gtataagaga                                30
```

VACUOLAR PYROPHOSPHATASES AND USES IN PLANTS

RELATED APPLICATIONS

This application is a continuation-in-part of U.S. application Ser. No. 11/119,683, filed May 2, 2005, which is a continuation of U.S. application Ser. No. 09/834,998, filed Apr. 13, 2001, which is a continuation of U.S. application Ser. No. 09/644,039, filed Aug. 22, 2000, which claims the benefit of U.S. Provisional Application No. 60/164,808, filed Nov. 10, 1999.

The entire teachings of the above applications are incorporated herein by reference.

GOVERNMENT SUPPORT

This invention was made with government support under grants GM52414, DK54214, DK43495, DK51509, DK34854 and GM35010 awarded by National Institutes of Health, under grant MCB9317175 awarded by the National Science Foundation, under grants awarded by the National Research Initiative, U.S. Department of Agriculture, Cooperative State Research, Education, and Extension Service no. 2006-35304-17339, and under grants awarded by Storrs Agricultural Experimental Station Hatch. The Government has certain rights in the invention.

BACKGROUND OF THE INVENTION

The prospects for feeding humanity as we enter the new millennium are formidable. The progressive salinization of irrigated land compromises the future of agriculture in the most productive areas of our planet (Serrano et al., 1994). Arid regions offer optimal photoperiod and temperature conditions for the growth of most crops, but suboptimal rainfall. Artificial irrigation has solved the problem in the short term. However, water supplies always contain some dissolved salt, which upon evaporation gradually accumulates on the soils. To grow in saline environments, plants must maintain a much lower ratio of $Na^+/K^+$ in their cytoplasm than that present in the soil. Thus, a need exists for crops having increased tolerance to salt.

In worldwide agricultural production, phosphorus is second only to nitrogen as the most limiting macronutrient. In soils, orthophosphate (Pi), the assimilated form of phosphorus, exists primarily as insoluble calcium salts or iron-aluminium oxide complexes that are inaccessible to plants (Holford, 1997). When aggressive fertilization is employed to alleviate available Pi deficiency, runoff from agricultural land represents a serious threat to aquatic and marine environments (Hammond et al., 2004). Thus, a need exists for crops having increased Pi uptake.

SUMMARY OF THE INVENTION

The present invention discloses transgenic plant cells and transgenic plants comprising transgenic plant cells, wherein the transgenic plant cells comprise an exogenous nucleic acid that causes overexpression of a plant vacuolar pyrophosphatase in the one or more transgenic plant cells, wherein the exogenous nucleic acid comprises a nucleic acid sequence encoding the plant vacuolar pyrophosphatase. The transgenic plants can have one or more enhanced phenotypic traits relative to non-transgenic wild-type plants of the same species. The present invention also discloses methods of making the transgenic plants.

According to one embodiment of the present invention, one or more transgenic plant cells comprise an exogenous nucleic acid that causes overexpression of a plant vacuolar pyrophosphatase in the one or more transgenic plant cells, wherein the exogenous nucleic acid comprises a nucleic acid sequence encoding the plant vacuolar pyrophosphatase. The transgenic plant cells can be from a plant selected from the group consisting of tomato, rice, tobacco, sorghum, cucumber, lettuce, turf grass, *Arabidopsis* and corn. They can be obtained from a tissue selected from the group consisting of roots, stems, leaves, flowers, fruits and seeds. The nucleic acid sequence encoding the plant vacuolar pyrophosphatase can be from a non-transgenic wild-type plant of the same species as the transgenic plant or from a non-transgenic wild-type plant of a species different from the transgenic plant. It can be obtained from a plant selected from the group consisting of *Arabidopsis*, tobacco, tomato and corn. It can be operably linked to at least one regulatory element that results in overexpression of the plant vacuolar pyrophosphatase. The plant vacuolar pyrophosphatase can be AVP1 or a homolog thereof.

According to another embodiment of the present invention, a transgenic plant comprises one or more transgenic plant cells comprising an exogenous nucleic acid that causes overexpression of a plant vacuolar pyrophosphatase in the one or more transgenic plant cells, wherein the exogenous nucleic acid comprises a nucleic acid sequence encoding the plant vacuolar pyrophosphatase. The transgenic plant can be selected from the group consisting of tomato, rice, tobacco, sorghum, cucumber, lettuce, turf grass, *Arabidopsis* and corn. The nucleic acid sequence encoding the plant vacuolar pyrophosphatase can be from a non-transgenic wild-type plant of the same species as the transgenic plant or from a non-transgenic wild-type plant of a species different from the transgenic plant. It can be obtained from a plant selected from the group consisting of *Arabidopsis*, tobacco, tomato and corn. It can be operably linked to at least one regulatory element that results in overexpression of the plant vacuolar pyrophosphatase. The plant vacuolar pyrophosphatase can be AVP1 or a homolog thereof. Transgenic progeny of the transgenic plant can comprise the exogenous nucleic acid. Transgenic seeds produced by the transgenic plant can comprise the exogenous nucleic acid. Transgenic progeny grown from the transgenic seeds can also comprise the exogenous nucleic acid. The transgenic plant can have one or more enhanced phenotypic traits relative to non-transgenic wild-type plants of the same species, and the enhanced phenotypic traits are selected from the group consisting of increased tolerance to one or more salts, increased yield, larger plant size and increased Pi uptake under Pi-sufficient growth conditions. It can also have one or more enhanced phenotypic traits relative to non-transgenic wild-type plants of the same species under Pi-deficient growth conditions, and the enhanced phenotypic traits are selected from the group consisting of increased root structure, increased root and shoot biomass, increased yield, increased biomass, delayed curtail of cell proliferation, increased Pi uptake, increased rhizosphere acidification, resistance to Al toxicity, increased organic acid exudates from root under Al stress, and increased root $K^+$ contents with or without Al stress.

According to yet another embodiment of the present invention, a method of making a transgenic plant with one or more enhanced phenotypic traits relative to non-transgenic wild-type plants of the same species comprises:

a) introducing an exogenous nucleic acid comprising a nucleic acid sequence encoding a plant vacuolar pyrophosphatase into one or more cells of a plant to generate transformed cells;

b) regenerating transgenic plants from the transformed cells;

c) selecting a transgenic plant with one or more enhanced phenotypic traits relative to non-transgenic wild-type plants of the same species, thereby producing the transgenic plant.

The one or more enhanced phenotypic traits can be selected from the group consisting of increased tolerance to one or more salts, increased yield, larger plant size and increased Pi uptake under Pi-sufficient growth conditions. They can also be selected from the group under Pi-deficient growth conditions consisting of increased root structure, increased root and shoot biomass, increased yield, increased biomass, delayed curtail of cell proliferation, increased Pi uptake, increased rhizosphere acidification, resistance to Al toxicity, increased organic acid exudates from root under Al stress, and increased root $K^+$ contents with or without Al stress. The transgenic plant can be selected from the group consisting of tomato, rice, tobacco, sorghum, cucumber, lettuce, turf grass, *Arabidopsis* and corn. The one or more cells of a plant can be obtained from a tissue selected from the group consisting of roots, stems, leaves, flowers, fruits and seeds. The nucleic acid sequence encoding the plant vacuolar pyrophosphatase can be from a non-transgenic wild-type plant of the same species as the transgenic plant or from a non-transgenic wild-type plant of a species different from the transgenic plant. It can be obtained from a plant selected from the group consisting of *Arabidopsis*, tobacco, tomato and corn. It can be operably linked to at least one regulatory element that results in overexpression of the plant vacuolar pyrophosphatase. The plant vacuolar pyrophosphatase can be AVP1 or a homolog thereof. The one or more salts can be selected from the group consisting of NaCl, KCl and $CaCl_2$. They can have a concentration of about 0.2 M to about 0.3 M in water.

According to still another embodiment of the present invention, a transgenic rice plant comprises one or more transgenic rice plant cells comprising an exogenous nucleic acid that causes overexpression of a plant vacuolar pyrophosphatase in the one or more transgenic rice plant cells, wherein the exogenous nucleic acid comprises a nucleic acid sequence encoding the plant vacuolar pyrophosphatase, and the transgenic rice plant has one or more enhanced phenotypic traits relative to non-transgenic wild-type rice plants, said enhanced phenotypic traits selected from the group consisting of more tillers, more panicles and increased P, Fe and Zn contents. The nucleic acid sequence encoding the plant vacuolar pyrophosphatase can be from a non-transgenic wild-type plant of the same species as the transgenic plant or from a non-transgenic wild-type plant of a species different from the transgenic plant. It can be obtained from a plant selected from the group consisting of *Arabidopsis*, tobacco, tomato and corn. It can be operably linked to at least one regulatory element that results in overexpression of the plant vacuolar pyrophosphatase. The plant vacuolar pyrophosphatase can be AVP1 or a homolog thereof. Transgenic progeny of the transgenic rice plant can comprise the exogenous nucleic acid. Transgenic seeds produced by the transgenic rice plant can comprise the exogenous nucleic acid. Transgenic progeny grown from the transgenic seeds can also comprise the exogenous nucleic acid.

According to yet another embodiment of the present invention, a method of making a transgenic rice plant with one or more enhanced phenotypic traits relative to non-transgenic wild-type rice plants comprises:

a) introducing an exogenous nucleic acid comprising a nucleic acid sequence encoding a plant vacuolar pyrophosphatase into one or more cells of a rice plant to generate transformed cells;

b) regenerating transgenic plants from the transformed cells;

c) selecting a transgenic rice plant with one or more enhanced phenotypic traits relative to non-transgenic wild-type plants of the same species, thereby producing the transgenic rice plant.

The one or more enhanced phenotypic traits can be selected from the group consisting of more tillers, more panicles and increased P, Fe and Zn contents. The one or more cells of a plant can be obtained from a tissue selected from the group consisting of roots, stems, leaves, flowers, fruits and seeds. The nucleic acid sequence encoding the plant vacuolar pyrophosphatase can be from a non-transgenic wild-type plant of the same species as the transgenic plant or from a non-transgenic wild-type plant of a species different from the transgenic plant. It can be obtained from a plant selected from the group consisting of *Arabidopsis*, tobacco, tomato and corn. It can be operably linked to at least one regulatory element that results in overexpression of the plant vacuolar pyrophosphatase. The plant vacuolar pyrophosphatase can be AVP1 or a homolog thereof.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2 is alignment of the deduced amino acid sequences of NhX1 homologue from *Arabidopsis* AtNHX1 (SEQ ID NO: 1), human HsNHE-6 (SEQ ID NO: 2) and yeast ScNHX1 (SEQ ID NO:3); identical residues are in black boxes, and dashes indicate gaps in the sequence, * above alignment denote putative amiloride binding site from human NHE1 ($^{163}$DVF-FLFLLPPI$^{173}$) (SEQ ID NO: 4).

FIG. 4 depicts a nucleotide sequence of *Arabidopsis thaliana* cDNA encoding vacuolar pyrophosphatase (AVP1) (SEQ ID NO: 6) and the predicted amino acid sequence of polypeptide (SEQ ID NO: 7) encoded by the nucleotide sequence.

DETAILED DESCRIPTION OF THE INVENTION

Figure 1A:
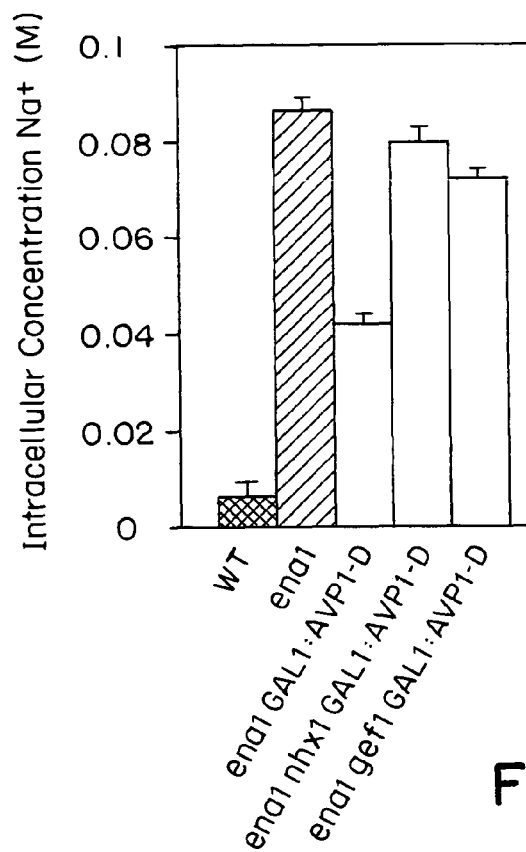
FIGS. 1A and 1B are bar graphs showing the intracellular $Na^+$ and $K^+$ contents of wild-type yeast strains and of yeast strains carrying various mutations affecting sodium tolerance; values are the mean of two determinations, and bars represent the standard deviations.

A description of example embodiments of the invention follows.

The teachings of all patents, published applications and references cited herein are incorporated by reference herein in their entirety.

Producing salt-tolerant plants using genetic engineering requires the identification of the relevant genes. Physiological studies suggest that salt exclusion in the root and/or salt sequestration in the leaf cell vacuoles are critical determinants for salt tolerance (Kirsch et al., 1996). Toxic concentrations of NaCl build up first in the fully expanded leaves where NaCl is compartmentalized in the vacuoles. Only after their loading capacity is surpassed, do the cytosolic and apoplasmic concentrations reach toxic levels, ultimately leading to loss of turgor, ergo plant death. It has been suggested that hyperacidification of the vacuolar lumen via the vacuolar $H^+$-ATPase (V-ATPase) provides the extra protons required for a $Na^+/H^+$ exchange-activity leading to the detoxification of the cytosol (Tsiantis et al., 1996). Salt stress increases both ATP- and pyrophosphate (PPi)-dependent $H^+$ transport in tonoplast vesicles from sunflower seedling roots. Salt treatments also induce an amiloride-sensitive $Na^+/H^+$ exchange activity (Ballesteros et al., 1997). In the halophyte *Mesembryanthemum crystallinum*, high NaCl stimulates the activities of both the vacuolar V-ATPase and a vacuolar $Na^+/H^+$ antiporter in leaf cells. As described herein, the plant components involved in the intracellular detoxification system have been identified by complementing salt-sensitive mutants of the budding yeast *Saccharomyces cerevisiae*. As also described herein, *Arabidopsis thaliana* (*A. thaliana*; Arabidopsis) has been used as a host model plant to demonstrate that overexpression of these genes results in salt tolerance in the plant.

Accordingly, the present invention is directed to transgenic plants which are tolerant to one or more salts. As used herein, the term "salt" refers to any salt, such as NaCl, KCl, and/or $CaCl_2$. In one embodiment, the transgenic plants of the present invention comprise one or more plant cells transformed with exogenous nucleic acid which alters expression of vacuolar pyrophosphatase in the plant. Any suitable vacuolar pyrophosphatase, several of which have been cloned, can be used in the compositions and methods of the present invention (e.g., Sarafian et al., 1992; Lerchl et al., 1995; Kim et al., 1994). *A. thaliana* vacuolar pyrophosphatase (AVP1) cDNA sequence and its encoded protein sequence (Sarafian et al., 1992) are shown in FIG. 4. As used herein, nucleic acid which "alters expression of vacuolar pyrophosphatase" includes nucleic acid which enhances (promotes) or inhibits expression of vacuolar pyrophosphatase in the transgenic plant. In a particular embodiment, the present invention relates to a transgenic plant which is tolerant to salt comprising an exogenous nucleic acid construct which is designed to overexpress AVP1 or designed to downregulate endogenous vacuolar pyrophosphatase. The present invention also encompasses transgenic plants which grow in a concentration of salt that inhibits growth of a corresponding non-transgenic plant. Transgenic progeny of the transgenic plants, seeds produced by the transgenic plant and progeny transgenic plants grown from the transgenic seed are also the subject of the present invention. Also described herein are plant cells comprising exogenous nucleic acid which alters expression of vacuolar pyrophosphatase in the plant cell.

Producing plants with increased Pi uptake using genetic engineering also requires the identification of the relevant genes. In response to limiting Pi availability, plant metabolic and developmental processes are altered to enhance Pi uptake. For example, in *Arabidopsis*, the coordinated induction of more than 600 genes is seen under conditions of Pi deprivation (Misson et al., 2005). Perhaps the most obvious consequence of altered gene expression in Pi-deprived plants is the expansion of their root architecture and resultant increases in absorptive surface area (Lopez-Bucio et al., 2002; Gahoonia and Nielsen, 2004). Pi-deprived roots exhibit transition of the primary root to determinate growth, greater frequency of lateral root formation and increased recruitment of trichoblasts to form root hairs (Abel et al., 2002; Poirier and Bucher, 2002; Sanchez-Calderon et al., 2006). In some species, Pi-deprived roots form specialized structures to enhance nutrient uptake, as is seen in white lupin (*Lupinus albus*), which forms clusters of short, hairy lateral roots (proteoid roots) that are specialized for Pi uptake (Yan et al., 2002). Another adaptation to low soil Pi is rhizosphere acidification, resulting from enhanced plasma membrane $H^+$-ATPase activity in roots (Yan et al., 2002; Zhu et al., 2005; Shen et al., 2006). Increased $H^+$ extrusion results in increased displacement of Pi from insoluble soil complexes (Vance et al., 2003). The advantage of these adaptations to low-Pi conditions is evident in the apparent universality of such responses in plants that prosper in low-Pi soils. As described herein, the plant components involved in the adaptations to low-Pi conditions have been identified by quantitative real-time fluorescence-polymerase chain reaction (RTF-PCR) and western blot analysis. As also described herein, *A. thaliana*, tomato and rice have been used as host model plants to demonstrate that overexpression of these genes results in increased Pi uptake in the plant.

Accordingly, the present invention is also directed to transgenic plants which have increased Pi uptake. As used herein, the term "Pi uptake" refers to total Pi content per plant, irrespective of the growth conditions. In one embodiment, the transgenic plants of the present invention comprise one or more plant cells transformed with exogenous nucleic acid which alters expression of vacuolar pyrophosphatase in the plant. Any suitable vacuolar pyrophosphatase, several of which have been cloned, can be used in the compositions and methods of the present invention (e.g., Sarafian et al., 1992; Lerchl et al., 1995; Kim et al., 1994). *A. thaliana* vacuolar pyrophosphatase (AVP1) cDNA sequence and its encoded protein sequence (Sarafian et al., 1992) are shown in FIG. 4. As used herein, nucleic acid which "alters expression of vacuolar pyrophosphatase" includes nucleic acid which enhances (promotes) or inhibits expression of vacuolar pyrophosphatase in the transgenic plant. In a particular embodiment, the present invention relates to a transgenic plant which has increased Pi uptake comprising an exogenous nucleic acid construct which is designed to overexpress AVP1 or designed to downregulate endogenous vacuolar pyrophosphatase. The present invention also encompasses transgenic plants which grow in a deficiency of Pi that inhibits growth of a corresponding non-transgenic plant. Transgenic progeny of the transgenic plants, seeds produced by the transgenic plant and progeny transgenic plants grown from the transgenic seed are also the subject of the present invention. Also described herein are plant cells comprising exogenous nucleic acid which alters expression of vacuolar pyrophosphatase in the plant cell.

Any suitable nucleic acid molecule which alters expression of vacuolar pyrophosphatase in the plant can be used to transform the transgenic plants in accordance with the present invention. Exogenous nucleic acid is a nucleic acid from a source other than the plant cell into which it is introduced or into a plant or plant part from which the tansgenic part was produced. The exogenous nucleic acid used for transformation can be RNA or DNA (e.g., cDNA and genomic DNA). In addition, the exogenous nucleic acid can be circular or linear, double-stranded or single-stranded molecules. Single-stranded nucleic acid can be the sense strand or the anti-sense strand.

The exogenous nucleic acid can comprise nucleic acid that encodes a vacuolar pyrophosphatase protein (an exogenous vacuolar pyrophosphatase), such as AVP1, a functional portion thereof (peptide, polypeptide), or a homolog thereof, and/or nucleic acid that alters (enhances or inhibits) expression of the endogenous vacuolar pyrophosphatase of the plant into which the exogenous nucleic acid is introduced. As used herein a "functional portion" of a nucleic acid that encodes a vacuolar pyrophosphatase protein is a portion of the nucleic acid that encodes a protein or polypeptide which retains a function characteristic of a vacuolar pyrophosphatase protein. In a particular embodiment, the nucleic acid encodes AVP1, a functional portion or a homolog thereof. As used herein "a homolog" of AVP1 refers to a homologous protein of AVP1 wherein the homologous protein performs the same function as AVP1 does in *Arabidopsis* but is from a different plant species, i.e. a homolog of AVP1 is a vacuolar pyrophosphatase of a plant species other than *Arabidopsis*. There is a high degree of identity at the amino acid level between vacuolar pyrophosphatases across the plant kingdom (Maeshima, 2000; Drozdowicz and Rea, 2001), suggesting that vacuolar pyrophosphatase from one species would be functional in another species. As described herein, this is indeed the case.

Nucleic acid that alters (enhances or inhibits) expression of the endogenous vacuolar pyrophosphatase of the plant into which the exogenous nucleic acid is introduced includes regulatory sequences (e.g., inducible or constitutive) which function in plants and antisense nucleic acid. Examples of regulatory sequences include promoters, enhancers and/or suppressors of vacuolar pyrophosphatase. The nucleic acid can also include, for example, polyadenylation site, reporter gene and/or intron sequences and the like whose presence may not be necessary for function or expression of the nucleic acid but can provide improved expression and/or function of the nucleic acid by affecting, for example, transcription and/or stability (e.g., of mRNA). Such elements can be included in the nucleic acid molecule to obtain optimal performance of the nucleic acid.

The nucleic acid for use in the present invention can be obtained from a variety sources using known methods. For example, the nucleic acid encoding a vacuolar pyrophosphatase (e.g., AVP1) for use in the present invention can be derived from a natural source, such as tobacco, bacteria, tomato or corn. In one embodiment, the nucleic acid encodes a vacuolar pyrophosphatase that corresponds to a wild type of the transgenic plant. In another embodiment, the nucleic acid encodes a vacuolar pyrophosphatase that does not correspond to a wild type of the transgenic plant. Nucleic acid that alters (enhances or inhibits) expression of the endogenous vacuolar pyrophosphatase of the plant into which the exogenous nucleic acid is introduced (e.g., regulatory sequences) can also be chemically synthesized, recombinantly produced and/or obtained from commercial sources.

A variety of methods for introducing the nucleic acid of the present invention into plants are known to those of skill in the art. For example, *Agrobacterium*-mediated plant transformation, particle bombardment, microparticle bombardment (e.g., U.S. Pat. No. 4,945,050; U.S. Pat. No. 5,100,792) protoplast transformation, gene transfer into pollen, injection into reproductive organs and injection into immature embryos can be used. The exogenous nucleic acid can be introduced into any suitable cell(s) of the plant, such a root cell(s), stem cell(s), leaf cell(s), flower cell(s), fruit cell(s) and/or seed cell(s) of the plant.

In one embodiment, a construct comprising a vacuolar pyrophosphatase gene operably linked to a promoter designed to overexpress the vacuolar pyrophosphatase (e.g., an expression cassette) or a construct designed to downregulate endogenous pyrophosphatase is used to produce the transgenic plants of the present invention. As used herein the term "overexpression" refers to greater expression/activity than occurs in the absence of the construct. In a particular embodiment, a construct comprising an AVP1 gene operably linked to a chimeric promoter designed to overexpress the AVP1 or designed to downregulate endogenous pyrophosphatase is used to produce the transgenic plants of the present invention. More particularly, the present invention relates to a construct wherein the AVP1 gene is operably linked to a double tandem enhancer of a 35S promoter.

Any suitable plant can be used to produce the transgenic plants of the present invention. For example, tomato, corn, tobacco, rice, sorghum, cucumber, lettuce, turf grass, ornamental (e.g., larger flowers, larger leaves) and legume plants can be transformed as described herein to produce the transgenic plants of the present invention. In addition, the transgenic plants of the present invention can be grown in any medium which supports plant growth such as soil or water (hydroponically).

The present invention also encompasses methods of making a transgenic plant which is tolerant to salt. In one embodiment, the method comprises introducing into one or more cells of a plant exogenous nucleic acid which alters expression of vacuolar pyrophosphatase in the plant to yield transformed cells in the plant, thereby producing a transgenic plant which is tolerant to salt. In another embodiment, the method comprises introducing into one or more cells of a plant a nucleic acid construct which is designed to overexpress AVP1 to yield transformed cells, thereby producing a transgenic plant which is tolerant to salt. The methods of making a transgenic plant can further comprise regenerating plants from the transformed cells to yield transgenic plants and selecting a transgenic plant which is tolerant to salt. The transgenic plants produced by these methods are also encompassed by the present invention.

The present invention also encompasses methods of making a transgenic plant with increased Pi uptake. In one embodiment, the method comprises introducing into one or more cells of a plant exogenous nucleic acid which alters expression of vacuolar pyrophosphatase in the plant to yield transformed cells in the plant, thereby producing a transgenic plant with increased Pi uptake. In another embodiment, the method comprises introducing into one or more cells of a plant a nucleic acid construct which is designed to overexpress AVP1 to yield transformed cells, thereby producing a transgenic plant with increased Pi uptake. The methods of making a transgenic plant can further comprise regenerating plants from the transformed cells to yield transgenic plants and selecting a transgenic plant which with increased Pi uptake. The transgenic plants produced by these methods are also encompassed by the present invention.

The transgenic plants of the present invention are useful for a variety of purposes. As described herein, the plant components involved in an intracellular cation detoxification system have been identified by complementing salt-sensitive mutants of the budding yeast *Saccharomyces cerevisiae*. As also described herein, the plant components involved in the adaptations to low Pi conditions have been identified by quantitative RTF-PCR and western blot analysis. The present invention relates to a method of bioremediating soil comprising growing one or more transgenic plants and/or progeny thereof in the soil, wherein the transgenic plants and/or progeny thereof comprise exogenous nucleic acid which alters expression of vacuolar pyrophosphatase in the plant. In another embodiment, the present invention relates to a method of removing cations (e.g., monvalent and/or divalent cations) from a medium which can support plant growth (e.g., soil, water) comprising growing one or more transgenic plants and/or progeny thereof in the medium, wherein the transgenic plants and/or progeny thereof comprise exogenous nucleic acid which alters expression of vacuolar pyrophosphatase in the plant. For example, the method can be used to remove sodium (Na), lead (Pb), manganese (Mn) and/or calcium (Ca) ions from a medium which supports plant growth. In another embodiment, the present invention relates to a method of scavenging Pi from a medium which can support plant growth (e.g., soil, water) comprising growing one or more transgenic plants and/or progeny thereof in the medium, wherein the transgenic plants and/or progeny thereof comprise exogenous nucleic acid which alters expression of vacuolar pyrophosphatase in the plant. For example, the method can be used to prevent Pi runoff from agricultural land.

Furthermore, it has been shown herein that the transgenic plants of the present invention are larger than the corresponding wild type plants (Example 3). Thus, the present invention provides for a method of increasing the yield of a plant comprising introducing into one or more cells of a plant nucleic acid which alters expression of vacuolar pyrophosphatase in the plant to yield transformed cells, thereby increasing the yield of the plant. The present invention also relates to a method of making a plant which is larger than its corresponding wild type plant comprising introducing into one or more cells of a plant nucleic acid which alters expression of vacuolar pyrophosphatase in the plant to yield transformed cells, thereby producing a transgenic plant which is larger than its corresponding wild type plant. The method can further comprise regenerating plants from the transformed cells to yield transgenic plants and selecting a transgenic plant which is larger than its corresponding wild type plant, thereby producing a transgenic plant which is larger than its corresponding wild type plant. Also encompassed by the present invention is a method of making a transgenic plant (e.g., an ornamental plant) having increased flower size compared to its corresponding wild type plant comprising introducing into one or more cells of a plant nucleic acid which alters expression of vacuolar pyrophosphatase in the plant to yield transformed cells, thereby producing a transgenic plant having increased flower size compared to its corresponding wild type plant.

The present invention also provides for a method of producing a transgenic plant which grows in salt water comprising introducing into one or more cells of a plant nucleic acid which alters expression of vacuolar pyrophosphatase in the plant to yield transformed cells, thereby producing a transgenic plant which grows in salt water. As used herein, "salt water" includes water characterized by the presence of salt, and preferably wherein the concentration of salt in the water is from about 0.2M to about 0.4M. In one embodiment, salt water refers to sea water.

The present invention also provide for a method of producing a transgenic plant which grows better than wild-type in Pi deficiency comprising introducing into one or more cells of a plant nucleic acid which alters expression of vacuolar pyrophosphatase in the plant to yield transformed cells, thereby producing a transgenic plant which grows better than wild-type in Pi deficiency. As used herein, "Pi deficiency" refers to a growth medium, either natural or artificial, containing lower Pi than what is required to support full growth of a wild-type plant, i.e. under Pi deficiency, growth of a wild-type plant is limited. Because different plants require different levels of Pi to fully grow, Pi deficiency, as used herein, is a plant-specific term.

The transgenic plants of the present invention can also be used to produce double transgenic plants which are tolerant to salt wherein a plant is transformed with exogenous nucleic acid which alters expression of a vacuolar phosphatase and exogenous nucleic acid which alters expression of another protein involved in sequestration of cations and/or detoxification in plants. In one embodiment, the present invention relates to a double transgenic plant which is tolerant to salt comprising one or more plant cells transformed with exogenous nucleic acid which alters expression of a vacuolar pyrophosphatase and an $Na^+/H^+$ antiporter in the plant. In one embodiment, the vacuolar pyrophosphatase is AVP1 or a homologue thereof and the $Na^+/H^+$ antiporter is AtNHX1 or a homologue thereof. The present invention further relates to a transgenic progeny of the double transgenic plant, as well as seeds produced by the transgenic plant and a progeny transgenic plant grown from the seed.

The transgenic plants of the present invention can also be used to produce double transgenic plants with increased Pi uptake wherein a plant is transformed with exogenous nucleic acid which alters expression of a vacuolar phosphatase and exogenous nucleic acid which alters expression of another protein involved in the adaptations to low-Pi conditions. In one embodiment, the present invention relates to a double transgenic plant with increased Pi uptake comprising one or more plant cells transformed with exogenous nucleic acid which alters expression of a vacuolar pyrophosphatase and a plasma membrane $H^+$-ATPase in the plant. In one embodiment, the vacuolar pyrophosphatase is AVP1 or a homologue thereof and the plasma membrane $H^+$-ATPase is AHA2 or AHA6 or a homologue thereof. The present invention further relates to a transgenic progeny of the double transgenic plant, as well as seeds produced by the transgenic plant and a progeny transgenic plant grown from the seed.

Figure 3A:
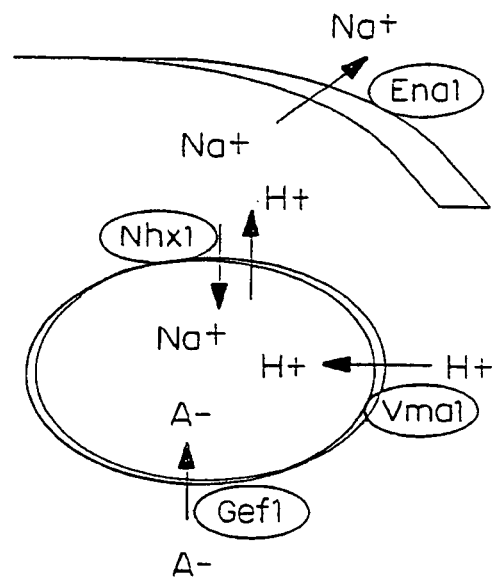
FIG. 3A is a schematic representation of a working model of the transporters involved in sodium sequestration at the yeast prevacuolar compartment; Nhx1 ($Na^+/H^+$ antiporter), Vma1 (vacuolar membrane $H^+$-adenosine triphosphatase ($H^+$-ATPase)), Gef1 (yeast CLC chloride channel), Ena1 (plasma membrane $Na^+$-ATPase).
Figure 3B:
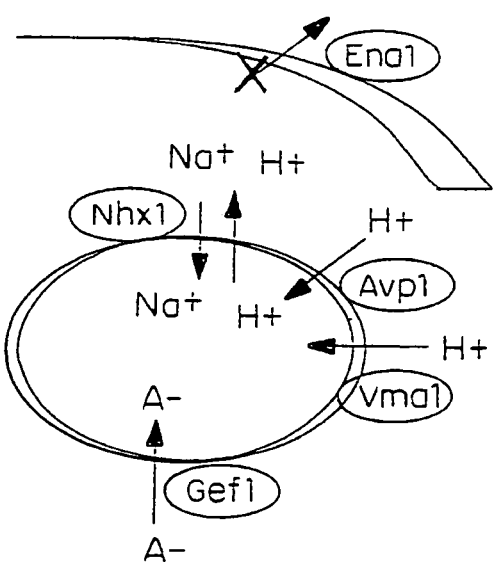
FIG. 3B is a schematic representation of a working model of the transporters involved in sodium sequestration at the yeast prevacuolar compartment shown in FIG. 3A, which also includes AVP1 (*Arabidopsis thaliana* vacuolar pyrophosphate-energized proton pump).

Investigation of the role of intracellular organelles in cation homeostasis via the identification and manipulation of key transporters is described herein. Most of these intracellular organelles, including clathrin-coated vesicles, endosomes, Golgi membranes and vacuoles have acidic interiors (Xie et al., 1989). This acidification is mediated by a proton-translocating electrogenic ATPase and in plant vacuoles also via a pyrophosphate-driven proton pump V-PPase (Davies et al., 1997; Zhen et al., 1997). There exists a requirement of anion transport to maintain net electroneutrality (al-Awqati, 1995). The yeast member of the CLC voltage-gated chloride channel superfamily, Gef1, is required for copper loading in late-Golgi vesicles and for cation sequestration in the prevacuolar compartment in yeast (Gaxiola et al., 1998; Gaxiola et al., 1999; Example 1). Furthermore, it has been shown that the defects of gef1 mutants can be suppressed by the introduction of the prototype member of the CLC superfamily, the Torpedo marmorata CLC-0 or by the introduction of *Arabidobsis thaliana* CLC-c and CLC-d chloride channel genes (Hechenberger et al., 1996; Gaxiola et al., 1998). While not wishing to be bound by theory, two observations led to the proposal of a model for $Na^+$ sequestration in yeast described herein (FIGS. 3A and 3B). First, gef1 mutants are sensitive to high NaCl concentrations. Second, the $Na^+/H^+$ exchanger Nhx1 localized to the prevacuolar compartment (Nass and Rao, 1998). This model posits that $Na^+$ sequestration by Nhx1 depends on the vacuolar $H^+$-ATPase and Gef1, the chloride channel. Gef1-mediated anion influx allows the establishment by the vacuolar $H^+$-ATPase of a proton gradient sufficient in magnitude to drive the uphill accumulation of $Na^+$ via $Na^+/H^+$ exchange.

This model is entirely consistent with the physiological data on the role of the vacuole in cation detoxification in higher plants. As described in Example 1, to test this sequestration model, mutant yeast strains (ena1) lacking the plasma membrane sodium efflux pump, which therefore must rely on the internal detoxification system in order to grow on high salt, were constructed. In theory, increasing the influx of protons into the postulated endosomal compartment should improve $Na^+$ sequestration via the Nhx1 exchanger. In order to increase the $H^+$ availability the *A. thaliana* gain-of-function mutant gene AVP1-D that codes for the vacuolar pyrophosphate-energized proton pump was expressed (FIG. 3B) (Zhen, Kim and Rea, 1997). This plant pump expressed in yeast restored the $Na^+$ resistance of the test strain, but only if the strain had functional NHX1 and GEF1 genes. Furthermore, Gef1p and Nhx1p colocalize within a common organelle, the prevacuolar compartment (Gaxiola et al., 1999). These results strongly support the model in FIGS. 3A and 3B and indicate that the yeast prevacuolar compartment can be used to identify the elusive plant transporters involved intracellular sodium detoxification.

Yeast and plant cells share pathways and signals for the trafficking of vesicles from the Golgi network to the vacuole (Neuhaus et al., 1998; Paris et al., 1997; Sato et al., 1997; Vitale et al., 1999). As shown herein, intracellular $Na^+$ detoxification in yeast requires functional $Na^+/H^+$ exchanger (Nhx1) and chloride channel (Gef1), and they colocalize to a prevacuolar compartment (Gaxiola et al., 1999). As described in Example 1, to further test the utility of this system, an *Arabidopsis thaliana* homologue of the yeast NHX1 gene (AtNHX1) was cloned and its function in the nhx 1 yeast mutant was tested. The AtNHX1 gene was able to suppress partially the cation sensitivity phenotypes of nhx 1 mutants. Further support for the role of the *Arabidopsis* AtNHX1 gene in salt homeostasis came from the observation that its expression is induced in salt-stressed plants (Gaxiola et al., 1999). A recent report shows that the overexpression of AtNHX1 gene in transgenic *Arabidopsis thaliana* promotes sustained growth in soil watered with 200 mM NaCl plus ⅛ M.S. salts under short-day cycle conditions (Apse et al., 1999). It is worth noting that every addition of ⅛ M.S. salts provides 2.5 mM potassium reducing the stringency of the NaCl stress, and that a short-day cycle reduces oxidative stress. As described in Example 2, transgenic plants that overexpress the AtNHX1 were generated (35SAtNHX1 transgenics).

In plants, most of the transport processes are energized by the primary translocation of protons. $H^+$-translocating pumps located at the plasma membrane and tonoplast translocated $H^+$ from the cytosol to extracellular and vacuolar compartments, respectively (Rea et al., 1990). The plant tonoplast contains two $H^+$-translocating pumps; the V-ATPase and the inorganic pyrophosphatase or V-PPase. Their action results in luminal acidification and the establishment of a $H^+$ electrochemical potential gradient across the tonoplast (Davies et al., 1997). The vacuolar membrane is implicated in a broad spectrum of physiological processes that include cytosolic pH stasis, compartmentation of regulatory $Ca^{2+}$, sequestration of toxic ions such as $Na^+$, turgor regulation, and nutrient storage and retrieval. The vacuole constitute 40 to 99% of the total intracellular volume of a mature plant cell. The vacuolar proton pumping pyrophosphatase is a universal and abundant component of plant tonoplast capable of generating a steady-state transtonoplast $H^+$ electrochemical potential similar or greater than the one generated by the V-ATPase (Rea et al., 1990). PPi is a by-product in the activation or polymerization steps of a wide range of biosynthetic pathways and in plants serves as an alternative energy donor to ATP for sucrose mobilization via sucrose synthase, for glycolysis via PPi: fructose-6-phosphate phosphotransferase and for tonoplast energisation via the vacuolar proton pumping pyrophosphatase (Stitt, 1998).

As described in Example 1, the overexpression of the *A. Thaliana* gain-of-function mutant gene AVP1-D increases the intracellular detoxification capability in yeast (Gaxiola et al., 1999). The rationale behind this approach is that an increased influx of $H^+$ into the vacuolar compartment should improve $Na^+$ sequestration via the Nhx1 exchanger. As described in Example 3, in order to test this hypothesis in plants, a transgenic *Arabidopsis thaliana* plant was engineered to overexpress the AVP1 wild-type gene using the double tandem enhancer of the 35S promoter (Topfer et al., 1987). AVP1 encodes the pyrophosphate-energized vacuolar membrane proton pump from *Arabidopsis* (Sarafian et al., 1992). Previous investigations suggest that the AVP1 gene is present in a single copy in the genome of *Arabidopsis* (Kim et al., 1994), however, a sequence homologous, but not identical, to AVP1 on chromosome one has been tentatively designated as ORF F9K20.2 on BAC F9K20 by the *Arabidopsis* Genome Initiative (AGI).

Five different lines of 35SAVP1 plants showed an enhanced salt tolerance as compared to wild-type plants in the T2 stage. However, the most dramatic phenotype was apparent in the homozygous T3 plants. These transgenic plants are larger than wild-type plants. Furthermore, homozygous 35SAVP1 plants show sustained growth in the presence of 250 mM NaCl plus ⅛ M.S. salts when grown in a 24 hours light regimen. Interestingly, when 35SAVP1 plants were grown under short-day cycle conditions sustained growth in the presence of 300 mM NaCl plus ⅛ M.S. salts was observed.

Hydroponic culture increases plant growth and provides stress-free root and shoot material (Gibeaut et al., 1997). Another important advantage of hydrophonic culture is that we can alter the ionic composition in a more accurate manner than in soil. These advantages could be important for the physiological studies of salt stress. As described in Example 4, wild type and 35SAVP1 transgenic plants were grown hydroponically. Under such conditions the size differences in root, leaves and stems among wild type and 35SAVP1 transgenic plants are dramatic. To learn about the salt tolerance of these plants under hydroponic conditions, NaCl concentration were increased stepwise by 50 mM every 4 days (Apse et al., 1999). 35SAVP1 transgenic plants appear healthy in the presence of 200 mM NaCl while wild type controls show severe deleterious effects in their leaves and stems.

Figure 5:
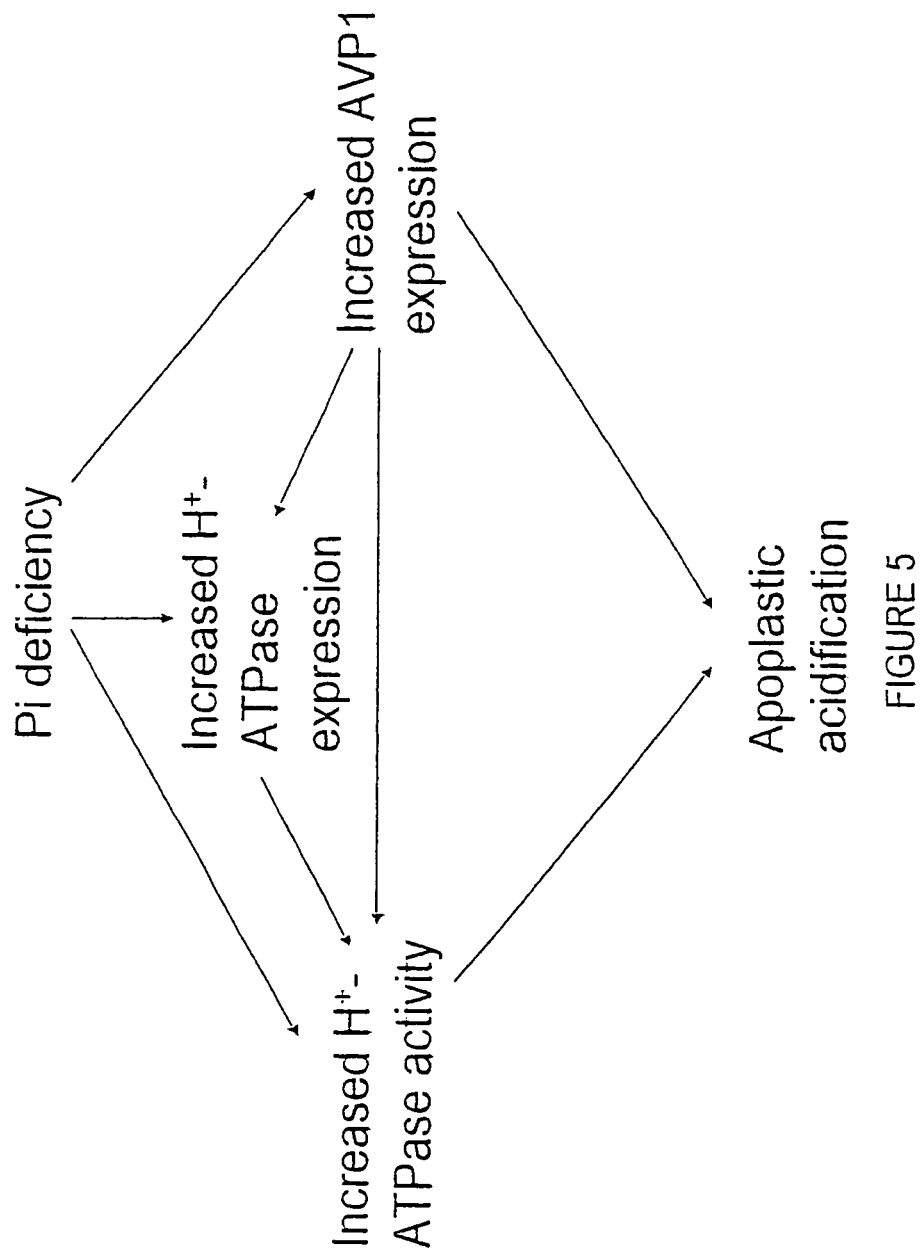
FIG. 5 is a diagram of a working model of some of the genes involved in apoplastic acidification of *Arabidopsis thaliana* during Pi deficiency.

Investigation of the plant components involved in the adaptations to low-Pi conditions via quantitative RTF-PCR and western blot analysis is described herein. Previous genome-wide transcriptional analysis using *Arabidopsis thaliana* Affymetrix gene chips identified a number of genes related to phosphate deprivation (Misson et al., 2005). However, the baseline on the gene chips could prevent the detection of relatively minor changes, resulting in false negatives. As described in Example 5, low Pi can increase transcript and protein abundance of AVP1 and $H^+$-ATPases in *A. thaliana*, whose induction has never been previously observed in *A. thaliana* following phosphate deprivation. While not wishing to be bound by theory, two observations led to the proposal of a model for apoplastic acidification in *A. thaliana* in Pi deficiency described herein (FIG. 5). First, microsomal fractions from AVP1 transgenic *Arabidopsis* plants (AtAVP1 OX) exhibited increased plasma membrane (PM) P-type $H^+$-ATPase (P-ATPase) protein abundance and activity (Li et al., 2005). Second, the apoplastic pH was significantly more acidic in AtAVP1OX than in wild-type plants (Li et al., 2005). This model posits that apoplastic acidification during Pi deficiency, which is the result of increased PM P-ATPase activity, at least partially depends on increased expression of AVP1 during Pi defiency. Increased AVP1 expression can lead to increased PM P-ATPase expression and activity, suggesting a mechanism that can be manipulated to produce plants that exhibit increased resilience to Pi deficiency.

This model is entirely consistent with the experimental data on the role of AVP1 in rhizosphere acidification in *Arabidopsis* under Pi deficiency. As described in Example 7, increased rhizosphere acidification in AtAVPOX1 under Pi deficiency was completely inhibited by 1 mM vanadate, an inhibitor of PM $H^+$-ATPase activity, as was rhizosphere acidification in wild-type plants. This result strongly supports the model in FIG. 5 and indicate that the previously observed increased apoplastic acidification in AtAVP1OX plants was to a large part, if not entirely, via increased PM $H^+$-ATPase activity.

Under nutrient-sufficient conditions, AVP1 transgenic plants exhibit certain enhanced phenotypic traits such as increased root structure, increased root and shoot biomass, increased yield, increased biomass and increased seed production (U.S. Patent Application Publication No. 2003-0213015 A1; U.S. Patent Application Publication No. US 2005-0278808 A1; Example 3). These enhanced phenotypic traits are also observed in AtAVP1OX as described herein. As described in Example 7, AtAVP1OX plants also exhibited enhanced growth and Pi uptake when grown in either Pi-sufficient or Pi-deficient conditions. The rationale behind this is that increased $H^+$ extrusion results in increased displacement of Pi from insoluble soil complexes, resulting in more efficient Pi scavenging.

Other AVP1 transgenic species, including AVP1 transgenic tomato (LeAVP1 OX) and AVP1 transgenic rice (OsAVP1 OX), also exhibited the aforementioned enhanced phenotypic traits under nutrient-sufficient conditions and enhanced growth and Pi uptake when grown in either Pi-sufficient or Pi-deficient conditions. Other phenotypic traits observed for AVP1 transgenic plants under Pi deficiency included, but were not limited to, increased root structure, increased root and shoot biomass, increased yield, increased biomass, delayed curtail of cell proliferation, faster and total Pi depletion, resistance to aluminum (Al) toxicity, increased organic acid exudates from root under Al stress, and increased root $K^+$ contents with or without Al stress. Mobilized Al is known as being toxic to plants. Pi deficiency is often a problem in tropical soils in which marginal Al toxicity limits agricultural production (Kochian et al., 2004).

Importantly, AVP1 transgenic rice was found to exhibit increased biomass and seed yields when grown under nutrient-sufficient conditions. Other enhanced phenotypic traits observed for AVP1 transgenic rice include, but are not limited to, more tillers, more panicles and increased phosphorus (P), iron (Fe) and zinc (Zn) contents.

Genetic engineering promises to transform modern agriculture. Salinization of soil due to irrigation has rendered much land unusable for crop production. Low level of P in tropical/subtropical soils result in agricultural losses. Fertilizer application results in P runoff pollution of aquatic and marine environments. Described herein is a strategy using genetic and molecular biological approaches to improve the intracellular $Na^+$ detoxification and the Pi uptake capabilities of crops. The fact that genetically engineered *Arabidopsis thaliana* plants that overexpress either AVP1 (the pyrophosphate-energized vacuolar membrane proton pump, this work) or AtNHX1 (the $Na^+/H^+$ antiporter (Apse et al., 1999, and this work) are capable of growing in the presence of 200 mM NaCl strongly supports the strategy described herein. The fact that genetically engineered *Arabidopsis*, tomato and rice plants have increased Pi uptake and enhanced growth in both Pi-sufficient and Pi-deficient conditions also strongly supports the strategy described herein. It is likely that a double transgenic plant will show a further enhanced salt-tolerant phenotype or an increased Pi uptake phenotype or both phenotypes. Moreover, the discovery that *Arabidopsis* and tomato plants over-expressing AVP1 are resistant to water deficit stress (Gaxiola et al., 2001, 2007; Park et al., 2005) further enhances the potential value of this approach, as low-Pi soils are common in developing nations where water deficits are not easily ameliorated by irrigation. Furthermore, it is shown herein that the *Arabidopsis thaliana* transporter AVP1 is able to perform similar function in important agricultural crops, such as tomato and rice. It is expected that AVP1 homologs from other species will be able to perform similar functions when transformed into plants. The increased size of AVP1 transgenic plants also contribute to future food security, namely potential yield increases in genetically engineered crops.

EXEMPLIFICATION

Example 1

The *Arabidopsis Thaliana* Proton Transporters, AtNhx1 and AVP1, can Function in Cation Detoxification in Yeast Materials and Methods Yeast strains and Plasmids. All strains used are isogenic to W303 (ura3-1.can1-100 leu2-3, 112trp1-1 his3-11, (Gaxiola et al., 1992). Plasmids pRG52 (Δgef1::HIS3) (Gaxiola et al., 1998) and pRG197 (Anhx1::HIS3) were used to construct the deletions of GEF1 and NHX1 genes, yielding strains RGY85 and RGY296, respectively. The ena1::HIS3 mutant was obtained from Fink Lab collection (L5709). Transformation was performed by using the lithium acetate method (Gietz et al., 1992). Double mutants RGY324 (gef1::HIS3 ena1::HIS3), RGY326 (nhx1::HIS3 ena1::HIS3), and RGY343 (gef1::HIS3 nhx1::HIS3) were obtained by crossing the single-mutant strains. Double mutants were identified among the meiotic progeny by scoring for the phenotypes associated with each of the single mutants. Sporulation, tetrad dissection, and mating types were scored as described (Guthrie and Fink, 1991). Cells were grown in YPD (1% yeast/2% peptone/2% dextrose; Difco), YPGAL (1% yeast/2% peptone/2% galactose; Difco), SD (Difco; Synthetic medium with 2% Dextrose), or APG (APG is a synthetic minimal medium containing 10 mM arginine, 8 mM phosphoric acid, 2% glucose, 2 mM $MgSO_4$, 1 mM KCl, 0.2 mM $CaCl_2$, and trace minerals and vitamins) (Rodriguez-Navarro and Ramos, 1984). $MnCl_2$ (Sigma), tetramethylammonium chloride (Sigma), NaCl (Sigma), or hygromycin-B (Sigma) were added as indicated.

Wild type, L5709 (ena1::HIS3), RGY324 (gef1::HIS3 ena1::HIS3), and RGY326 (nhx1::HIS3 ena1::HIS3) strains were transformed with pYES2 vector (Invitrogen) and plasmid pYES2-AVP1-E229D described in ref. Zhen, Kim and Rea, 1997. The strain RGY343 (gef1::HIS3 nhx1::HIS3), used for histochemical analysis, was transformed with pRG151 (GEF1-GFP) (Gaxiola et al., 1998) and with pRIN73 [NHX1-$(HA)_3$] (Nass and Rao, 1998).

Wild-type and RGY296 (nhx1::HIS3) strains were transformed with vector pAD4 (Ballester et al., 1989). RGY296 (nhx1::HIS3) was transformed with pRG308 (ADH1::AtNHX1) (see Cloning of AtNHX1).

Determination of Intracellular Sodium and Potassium content. Cells were grown overnight in SD-ura medium (Difco; synthetic medium with 2% dextrose without uracil). YPGAL (1% yeast extract/2% peptone/2% galactose; Difco) media was inoculated with the overnight stocks and grow to an $A_{600}$ of 0.6. At this optical density (OD), NaCl was added to a final concentration of 0.7 M. The cells incubated for 6 h, harvested by centrifugation, washed two times with 1.1 M sorbitol and 20 mM $MgCl_2$, and entracted with water for 30 min at 95° C. The amount of $Na^+$ and $K^+$ in cells was determined at the University of Georgia Chemical Analysis Laboratory by an Inductively Coupled Plasina-MS. Intracellular cation concentrations were estimated as described (Gaxiola et al., 1992) by using the intracellular water value calculated for cells grown in 1 M NaCl.

Immunofluorescence. The strain RGY343 (gef1::HIS3 nhx1::HIS3) was grown in SD-ura, -leu medium (Difco; synthetic medium with 2% dextrose without uracil and leucin) to mid-logarithmic phase, 0.1 mg/ml hygromycin B was added, and the culture was incubated for 1 h at 30° C. Cells were fixed with 3.7% formaldehyde (Sigma) for 45 min at room temperature without agitation. Spheroplast formation, permeabilization, washing, and antibody incubation was performed as described (Pringle et al., 1991). MAB HA11 used as first antibody was from Babco (Richmond, Calif.). Cy3-conjugated goat antimouse IgG was from Jackson Immunoresearch. 4',6-Diamidino-2-phenylindole (Sigma) was added to mounting medium to stain mitochondrial and nuclear DNA.

Subcellular Fractionation and Western Analysis. The strain RGY343 (gef1::HIS3 nhx1::HIS3) was grown in APG medium (pH 7.0), and lysates fractioned on a 10-step sucrose density gradient as described (Nass and Rao, 1998). Aliquots of individual fractions (100 μg) were subjected to SDS/PAGE and transferred to nitrocellulose as described (Nass and Rao, 1998). Western blots were probed with monoclonal anti-GFP (green fluorescent protein) antibody (1:10,000 dilution; CLONTECH), anti-hemagglutinin antibody (1:10,000 dilution: Boehringer Mannheim), and peroxidase-coupled goat anti-mouse antibody (1:5,000;) and developed by using the ECL enhanced chemiluminescence system (Amersham Pharmacia).

Plant Strains, Growth conditions and RNA Preparation. *A. thaliana* plants (ecotype Columbia) were grown aseptically on unsupplemented plant nutrient agar without sucrose (Haughn and Somerville, 1986) for 15 days at 19° C. and under continuous illumination. NaCl or KCl was added to a final concentration of 250 mM, and the plants were incubated for 6 h. Total RNA from tissue of salt-treated and untreated plants was isolated (Niyogi and Fink, 1992). Hybond-N (Amersham) membranes were hybridized with a $^{32}P$-Labeled DNA probe from plasmid pRG308. Hybridization was performed at 65° C. overnight. Washes were performed at 65° C. with 0.2% standard saline citrate (SSC)/0.1% SDS. 18S probe was used as loading control. MACBAS 2.4 program was used to quantify the relative amount of RNA.

Cloning of AtNHX1. AtNHX1 was cloned from a phage cDNA library of *A. thaliana* (Kieber et al., 1993) (obtained from the *Arabidopsis* Biological Resource Center) by probing with an expressed sequence tag (Arabidopsis Biological Resources Center, DNA Stock Center) containing a partial clone. A full-length clone (2.1 kilobase; kb) was ligated into vector pSK2 (Stratagene) at the NotI site, generating plasmid pRG293. The AtNHX1 open reading frame (ORF) was amplified via PCR by using pRG293 as template and GGC-CCGGGATGGATTCTCTAGTGTCGAAACTGCCTTCG (SEQ ID NO: 5) and T7 oligonucleotides. The PCR product was then digested with XbaI and SalI and ligated into pAD4 vector generating plasmid pRG308. The AtNHX1 ORF was sequenced to verify the fidelity of the PCR product. The full-length sequence is longer than the ORF reported by the *Arabidopsis* Genome Initiative (A TM021B04.4), and has been deposited in GenBank (accession no. AF106324).

Results

The *Arabidopsis* Vacuolar $H^+$-Pyrophosphatase (AVP1) Confers Salt Tolerance to Yeast ena1 Mutants. To determine the components of the intracellular system required for sodium detoxification, an ena1 mutant that lacks the plasma membrane sodium efflux pump and therefore must rely on the internal detoxification system to overcome sodium toxicity was used. Growth of the ena1 strain is sensitive to low concentrations of sodium (200 mM), concentrations that do not inhibit the growth of wild-type strains. The sequestration model (Nass and Rao, 1998; Gaxiola et al., 1998) predicts that the ena1 strain would become salt tolerant if one could enhance the availability of protons in the postulated endosomal compartment. With increased influx of protons, cytoplasmic $Na^+$ would be sequestered via the Nhx1 exchanger. The yeast vacuolar ATPase is a multisubunit protein, so it is difficult to increase its activity by overexpressing any one of its subunits. However, it is possible to increase the influx of protons by expressing the *A. thaliana* AVP1 gene in yeast. This gene encodes a single polypeptide that, when expressed in yeast, is capable of pumping protons into the lumen of the vacuole (Kim et al., 1994). To ensure maximum activity of this proton pump, the E229D gain-of-function mutant of the AVP1 gene (AVP1-D) that has enhanced $H^+$ pumping capability was expressed (Zhen, Kim and Rea., 1997).

Overexpression of AVP1-D restored salt tolerance to salt-sensitive ena1 mutants. The restoration of salt tolerance to an ena1 strain by AVP1-D requires functional NHX1 and GEF1 genes: ena1nhx1 AVP1-D and ena1 gef1 AVP1-D strains are salt sensitive.

Figure 1B:
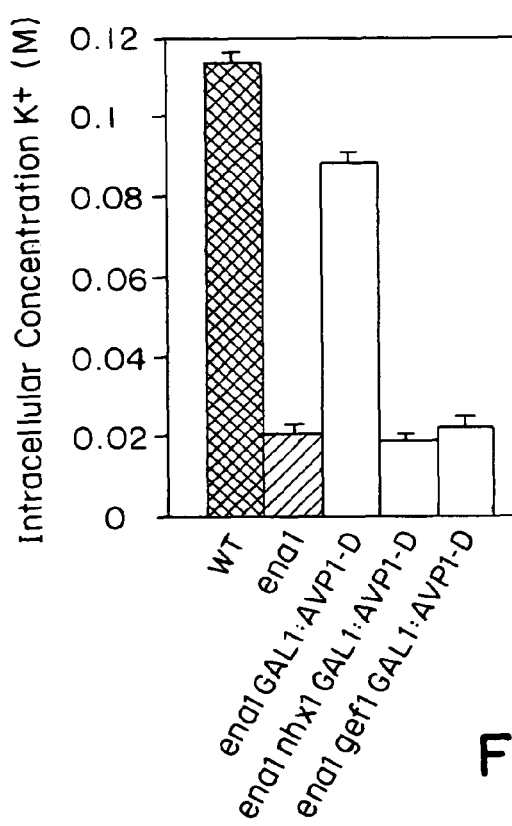

Expression of *Arabidopsis* vacuolar pyrophosphatase AVP1 in ena1 mutants: Vector pYES2 (Invitrogen) was introduced into wild-type, ena1, ena1 nhx1, and ena1 gef1 mutants. Plasmid pYes2-AVP1-D (Zhen, Kim and Rea, 1997) was introduced into ena1, ena1 nhx1, and ena1 gef1 mutants. Five-fold serial dilutions (starting at $10^5$ cells) of each strain were plated on YPGAL (1% yeast extract/2% peptone/2% galactose) with or without 0.5 M NaCl and incubated at 30° C. for 2 days. FIGS. 1A and 1B show intracellular concentrations of $Na^+$ and $K^+$. Exponentially growing cells (wild-type and ena1 transformed with pYES2 vector and ena1, ena1 nhx1, and ena1 gef1 mutants carrying pYes2-AVP1-D) were exposed to 0.7 M NaCl for 6 hours. Total cell extracts were prepared (see Materials and Methods), and $Na^+$ and $K^+$ concentrations were determined. There is a consistent reduction in total cell $Na^+$ in the ena1 AVP-D strain. The reason for this reduction is unknown.

The intracellular $Na^+$ and $K^+$ contents of wild-type strains and of strains carrying various mutations affecting sodium tolerance were determined after 6 h of exposure to media supplemented with 0.7 M NaCl (FIGS. 1A and 1B). The intracellular $Na^+$ content in the ena1 mutant is 8-fold higher than in the wild-type strain. The ena1 AVP-D strain is salt-resistant, even though its intracellular $Na^+$ content is 4-fold higher than that of the wild type. In ena1AVP1-D strains lacking either gef1 or nhx1 (i.e., ena1 gef1 or ena1 nhx 1), the $Na^+$ content is not reduced to the extent that it is in GEF1 NHX1 strain. Taken together, the genetic and physiological data are consistent with the model that Nhx1, Gef1 and Avp1 cooperate to sequester sodium internally.

The intracellular $K^+$ content correlates with salt tolerance and is inversely correlated with the $Na^+$ content of our strains (FIG. 1B). The wild-type $K^+$ concentration is ≈100 mM but is reduced to 20 mM in the ena1 mutant. Interestingly, in an ena1 strain that overexpresses the AVP1-D gene, the intracellular concentration of $K^+$ is restored almost to wild-type levels (FIG. 1B). However, AVP1-D overexpression fails to restore wild-type levels of intracellular potassium unless both NHx1 and GEF1 are functional (see the double mutants ena1 nhx1 or ena1 gef1 in FIG. 1B).

The NHX1 and GEF1 genes, which have been identified as important in sodium detoxification, are also required for the detoxification of other cations. Growth of gef1 and nhx1 mutants in the presence of toxic cations: Five-fold serial dilutions (starting at $10^5$ cells) of the indicated strains were grown at 30° C. for 2 days on YPD (1% yeast extract/2% peptone/2% dextrose) with the addition of either 3 mM $MnCl_2$, 0.45 M tetramethylammonium (TMA), or 0.05 mg/ml hygromycin B (HYG) as indicated.

For example, gef1 mutants are sensitive to 3 mM $MnCl_2$, 0.45 M tetramethylammonium chloride and to 0.05 µg/ml hygromycin-B. The nhx1 mutant is also sensitive to tetramethylammonium chloride and hygromycin. The extreme sensitivity of the nhx1 mutant to hygromycin provides an important tool for assaying nhx1 function.

Gef1p and Nhx1p Colocalize. The sequestration model postulates not only a functional connection between the anion channel Gef1 and sodium exchanger Nhx1 but also predicts that these two proteins colocalize within a common compartment. Because previous studies indicated that Nhx1 localizes to a prevacuolar compartment (Nass and Rao, 1998), two types of experiments were performed to determine whether Gef1 and Nhx1 proteins colocalize to this compartment.

Distribution of fluorescence and immunodetection of subcellular fractions in gef1 nhx1 cells transformed with two constructs: a GEF1-GFP fusion and a NHX1-(HA)$_3$-tagged fusion were determined. The strain RGY419 (gef1 nhx1) was transformed with plasmids pRG151; GEF1-GFP and pRIN73; NHX1-(HA)$_3$. Transformants were grown in SD (Difco; synthetic medium with 2% dextrose). When the cells reached $OD_{600}$=0.5, hygromycin B (Sigma) was added to a final concentration of 0.1 mg/ml and the cells were incubated for 40 min at 30° C. Cells were fixed and stained with antibodies to HA epitope and 4',6-diamidino-2-phenylindole (DAPI). Cells were viewed by charge-coupled device microscopy and optically sectioned by using a deconvolution algorithm (Scanalytics, Billerica, Mass.) (Kennedy et al., 1997); (Bar=1 µm).

It was found that hemagglutinin (HA)-tagged Nhx1 and Gef1-GFP fusion protein colocalize as shown via epifluorescence deconvolution microscopy (FIG. 3A). Persistence of signal coincidence on 90° rotation of the image further supports colocalization of the two transporter proteins in these cells.

The colocalization of Nhx1 (HA)$_3$ and GEF1-GFP is also supported by the comigration of the two proteins in sucrose density gradients of membrane preparations obtained from cells expressing the tagged proteins. The strain RGY419 (gef1 nhx1) transformed with plasmids pRG151; GEF1-GFP and pRIN73; NHX1-(HA)$_3$ was grown in APG medium (Rodriguez-Navarro and Rea, 1984), converted to spheroplasts, lysed, and fractionated on a 10-step sucrose gradient (18-54%) as described (Sorin et al, 1997; Antebi and Fink, 1992). Western blots showed the distribution of Gef1-GFP and Nhx1-HA (see Example 1, Materials and Methods).

The sedimentation behavior of the membrane fraction containing both proteins is consistent with that of a prevacuolar compartment (Nass and Rao, 1998). Gef1-GFP (but not Nhx1) is also present in Golgi fractions, consistent with previous studies (Gaxiola et al., 1998; Schwappach et al., 1998).

Figure 2:
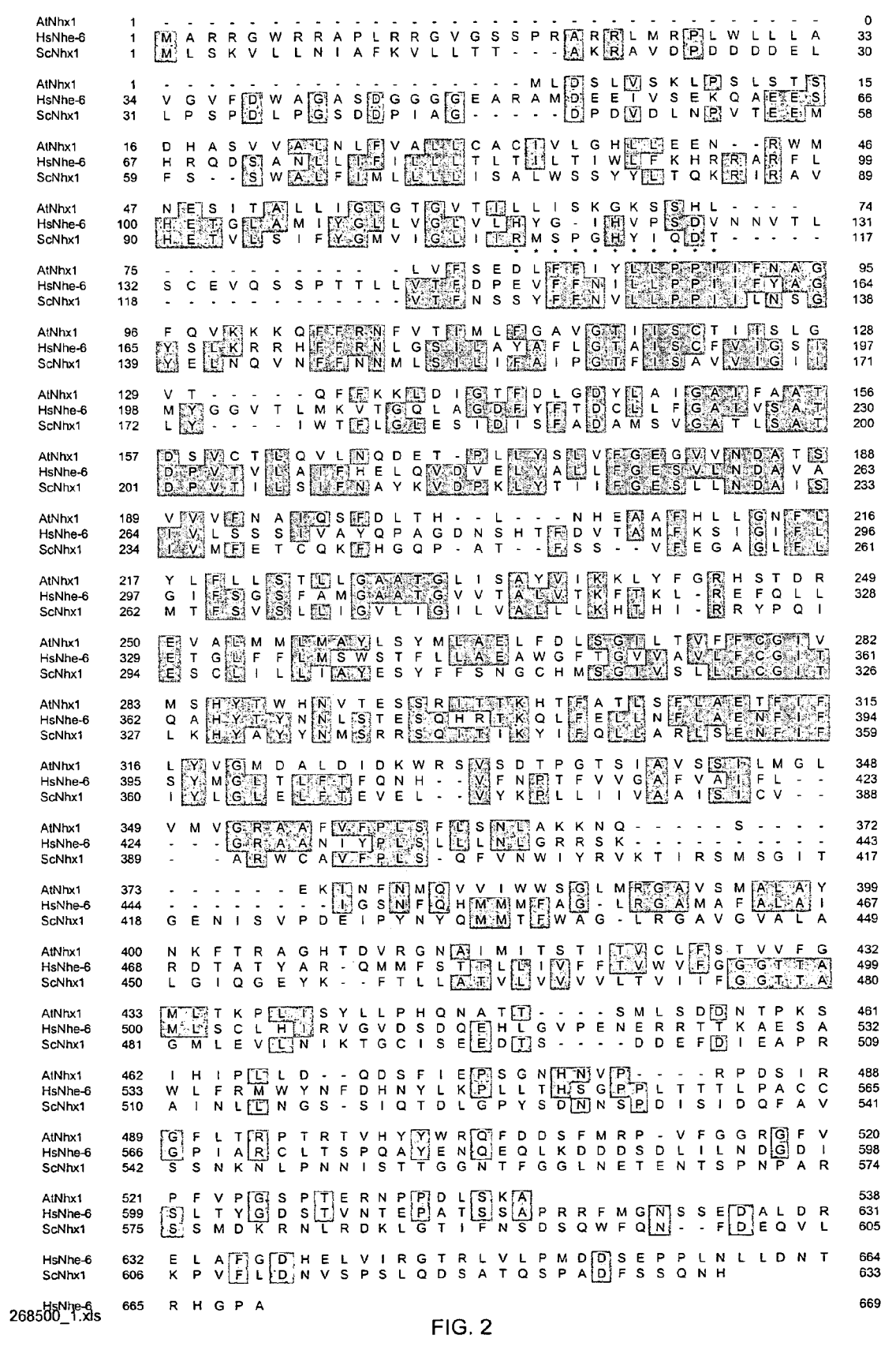

An *A. thaliana* Homologue of NHX1 Functions in Yeast. The yeast strain described herein provides an important tool for identifying genes that mediate salt tolerance in other organisms. To test the utility of this system, a sequence from *Arabidopsis* (See Materials and Methods) with very high homology to the *S. cerevisiae* NHX1 ORF was identified and used an expressed sequence tag (see Materials and Methods) to obtain a full-length clone of this *Arabidopsis* gene. An alignment of the amino acid sequences of Nhx1 homologues from *Arabidopsis* (AtNhx1), human (HsNhe6), and yeast (ScNhx1) reveals segments of amino acid identity and similarity within predicted transmembrane domains (FIG. 2). However, it is important to note that despite these relationships, neither the N-terminal nor the C-terminal regions of AtNhx1 and ScNhx1 show a high degree of homology (FIG. 2). A characteristic of mammalian $Na^+/H^+$ antiporters is their inhibition by amiloride. A putative amiloride binding site ($^{163}$DVFFLFLLPPI$^{173}$) (SEQ ID NO: 4) has been defined via point mutants in the human NHE1 antiporter gene (Counillon et al., 1993). AtNhx1, HsNhe-6 and ScNhx1 have an almost identical sequence (FIG. 2). However, our attempts to inhibit the activity of either Nhx1 or AtNhx1 in yeast cultures with amiloride were unsuccessful.

The extreme sensitivity of yeast nhx1 mutants to hygromycin permitted the testing of whether the cloned *Arabidopsis* AtNHX1 ORF could provide $Na^+/H^+$ exchange function in yeast. Vector pAD4 (Ballester et al., 1989) was introduced into wild-type and nhx1 strains. Plasmid pRG308; ADH; AtNHX1 was introduced into nhx1 mutants as indicated. Five-fold serial dilutions (starting at $10^5$ cells) of the indicated strains were grown at 30° C. for 2 days on YPD (−) or on YPD supplemented with 0.05 mg/ml hygromycin (+). Serial dilutions of the same strains were grown on APG medium (see Materials and Methods) (−) or on APG supplemented with 0.4 M NaCl (Rodriguez-Navarro and Ramos, 1984).

The At NHX1 gene is capable of suppressing the hygromycin sensitivity of the nhx1 mutant. The AtNHX1 gene also suppressed the NaCl sensitivity of nhx1 mutant but only under conditions in which the $K^+$ availability was reduced. However, AtAHX1 was not capable of rescuing the $Na^+$-sensitive growth phenotype of the double mutant ena1 nhx1 overexpressing the AVP1-D gene.

Further support for the role of the *Arabidopsis* AtNHX1 gene in salt homeostasis came from an analysis of its expression in salt-stressed plants. Plants were grown for 15 days under standard conditions and then exposed for 6 h to either 250 mM NaCl or KCl. The NaCl stress increased AtNHX1 mRNA levels 4.2-fold, whereas KCl promoted only a 2.8-fold increase. This increase in mRNA level produced by sodium resembles that described for the yeast NHX1 gene (Nass and Rao, 1998). RNA tissue blot hybridized with AtNHX1. Ten micrograms of total RNA from 15-day old plants exposed to 250 mM NaCl or Kcl for 6 h and a control grown without salt was subjected to electrophoresis on a denaturing formaldehyde gel. The blot was hybridized with a probe internal to AtNHX1 ORF. An 18S ribosomal probe was used as a loading control.

Discussion

The studies described herein provide evidence for the importance of the prevacuolar pH for intracellular $Na^+$ sequestration in yeast. Overexpression of the plant $H^+$-pyrophosphatase (AVP1) confers salt tolerance to yeast only in those strains containing a functional chloride channel (Gef1) and the $Na^+/H^+$ exchanger (Nhx1).

These data support a model in which the Nhx1 $Na^+/H^+$ exchanger acts in concert with the vacuolar ATPase and the GEF1 anion channel to sequester cations in a prevacuolar compartment. Several studies suggest that the prevacuolar compartment may be derived both from the plasma membrane and the late Golgi. These vesicles are likely involved in the assembly of the vacuole or delivery of cargo to this organelle. It is reasonable to expect that these prevacuolar vesicles detoxify cations by sequestration, thereby lowering their concentrations in the cytoplasm and in other organelles.

The yeast system described herein permits the functional assessment of diverse heterologous proteins in salt tolerance: chloride channels, $H^+$ pumps, and $Na^+/H^+$ exchangers and other cation/$H^+$ exchangers or cation/bicarbonate symporters. The system is robust and flexible. The function of the *Arabidopsis* chloride channels (Gaxiola et al., 1998; Hechenberger et al., 1996), $H^+$ pump, and $Na^+/H^+$ exchanger can be assayed in the corresponding yeast mutant. Despite the inability of At NHX1 to suppress all the phenotypes of the yeast nhx1 mutant, the fact that it suppresses some phenotypes, coupled with the DNA homology between AtNHX1 and yeast NHX1, indicates that the plant gene carries out a similar function to that of the yeast homologue. The observation that the AtNHX1 gene suppresses the sensitivity of the nhx1 mutant to hygromycin but provides only a weak $Na^+$ detoxification phenotype could be a consequence either of differential regulation of the transporters in the two organisms or of distinct cation transport selectivities.

The regulation of AtNHX1 by salt and the ability of the plant gene to suppress the yeast nhx1 mutant suggest that the mechanism by which cations are detoxified in yeast and plants may be similar. Indeed, previous work suggested that vacuolar sodium accumulation in salt-tolerant plants may be mediated by a tonoplast $Na^+/H^+$ antiporter that utilizes the proton-motive force generated by the vacuolar $H^+$-ATPase (V-ATPase) and/or $H^+$-translocating pyrophosphatase (V-PPase; refs. Barkla et al., 1994; Zhen, et al., 1997; Kirsch et al., 1996).

The finding described herein that both gef1 and nhx 1 mutants are hypersensitive to hygromycin indicate that the level of resistance to hygromycin depends on the function of the vacuolar and prevacuolar organelles. Yeast mutants impaired in $K^+$ uptake (trk1) are hypersensitive to hygromycin (Madrid et al., 1998); reduced $K^+$ uptake hyperpolarizes the plasma membrane potential and drives the uptake of alkali cations such as hygromycin. Mutations that reduce the $H^+$ pumping activity of the plasma membrane $H^+$-ATPase, Pma1, depolarize the plasma membrane potential and confer resistance to hygromycin (McCusker et al., 1987). Thus, mutants such as gef1 or nhx1 that affect the pH or membrane potential of the vacuolar and prevacuolar compartments may be expected to affect hygromycin compartmentation.

Example 2

Transgenic Plants that Overexpress the AtNHX1

Transgenic plants that overexpress the AtNHX1 were generated using *Agrobacterium*-mediated plant transformation. The transgenic AtNHX1 was expressed using a double tandem enhancer of the 35S promoter of CaMV (Topfer et al., 1987). T3 transgenic plants are less affected than wild type controls when watered with 300 mM NaCl.

15 wild-type plants and 15 35SAtNHX1 transgenic were grown on a 12 hours-day cycle for 20 days. During this period plants were watered every 5 days with a diluted nutrient solution (⅛ M.S. salts). 200 mM NaCl was added to the watering solution at day 21 and at day 33 plants were watered with a nutrient solution containing 300 mM NaCl. Plants were photographed 10 days after the last NaCl treatment.

Example 3

Salt-Stressed Wild Type Plants and 35SAVP1 Transgenics

Transgenic plants that overexpress AVP1 were generated using *Agrobacterium*-mediated plant transformation. The transgenic AVP1 was expressed using a double tandem enhancer of the 35S promoter of CaMV (Topfer et al., 1987). 15 wild-type plants and 15 35SAVP1 transgenics were grown on a 24 hours-day cycle for 16 days. During this period plants were watered every 4 days with a diluted nutrient solution (⅛ M.S. salts). 200 mM NaCl was added to the watering solution at day 17 and at day 27 plants were watered with nutrient solution containing 250 mM NaCl. Plants were photographed 10 days after the last NaCl treatment. Identical conditions and treatment as described in Example 2 were used.

These transgenic plants are larger than wild-type plants. Furthermore, homozygous 35SAVP1 plants show sustained growth in the presence of 250 mM NaCl plus ⅛ M.S. salts when grown in a 24 hours light regimen. Interestingly, when 35SAVP1 plants were grown under short-day cycle conditions (12 hour day/light cycle) sustained growth in the presence of 300 mM NaCl plus ⅛ M.S. salts was observed.

Example 4

Hydroponically Grown Wild Type and 35SAVP1 Transgenic Plants

Hydroponically grown wild type and 35SAVP1 transgenic plants were generated. 65 days old wild type and 35SAVP1 transgenic plants grown in solution culture on a 12 hour light cycle.

Wild type and 35SAVP1 transgenic plants were also grown in solution culture on a 12 hours light cycle for 20 days.

Starting at day 21, NaCl concentration was increased in a stepwise fashion by 50 mM increments every 4 days. Plants were photographed after 4 days in the presence of 200 mM NaCl.

Example 5

Low Pi increases transcript and protein abundance of AVP1 and P-ATPase in *Arabidopsis*

Materials and Methods

Quantitative RTF-PCR. *Arabidopsis thaliana* plants were germinated in half-strength MS medium for 2 weeks, and then transferred to 10 µM Pi plates for 0-48 h. Total RNA was isolated from seedlings (10-15 seedlings per sample) with TRI-reagent (Molecular Research Center, Cincinnati, Ohio, USA), according to the manufacturer's manual. After being treated with DNase I (DNA-free Kit, Ambion, Austin, Tex., USA), 1 µg of each RNA sample was used to synthesize cDNA with an iSript cDNA Synthesis Kit (Bio-Rad Laboratories, Hercules, Calif., USA) in a total volume of 20 µL at 41° C. for 1 h.

RTF-PCR was performed in a LightCycler 2.0 (Roche Applied Science, Mannheim, Germany), in a total volume of 25 µL containing 0.1 mL RT reaction (diluted into 5 µL) as template, using a LightCycler FastStart DNA MasterPLUS SYBR Green I Kit, according to the manufacturer's manual (Roche Applied Science). The transcription levels of AtPT1, AVP1 and AHAs genes were normalized to ACT2. The following are the specific primer pairs for the different genes designed with LightCycler Probe Design2 software (Roche Applied Science): ACT2, 5'CCCGCTATGTATGTCGC3' (SEQ ID NO: 8) and 5'TCCAGCAAGGTCAAGACG3' (SEQ ID NO: 9); AtPT1, 5'CCTCCTCAAGTTGACTA-CATT3' (SEQ ID NO: 10) and 5'CTCGATATCTGTTTG-TAAGACCT3' (SEQ ID NO: 11); AVP1, 5'GTTTCGT-CACTGAGTACTACAC3' (SEQ ID NO: 12) and 5'TCATGATAGCAATAGCAAAGATTGGA3' (SEQ ID NO: 13); AHA1, 5'TCCATCCCTGTTGAGGAGT3' (SEQ ID NO: 14) and 5'ATATCTGCTTTCTTCAAAGCGG3' (SEQ ID NO: 15); AHA2, 5'ATTGACGGCAGTGGTAAC3' (SEQ ID NO: 16) and 5'CGAGCAACAGCCAACGA3' (SEQ ID NO: 17); AHA6, 5'AGATGAGATAATTGA-CAAGTTTGCT3' (SEQ ID NO: 18) and 5'TCTGCACTGT-CATGTCTTGGA3' (SEQ ID NO: 19). Their specificity was confirmed by BLASTN in the National Center for Biotechnology Information (NCBI).

Western blot analysis. Seeds of *A. thaliana* plants were germinated in half-strength MS medium for 2 weeks, and then transferred to 10 µM Pi plates. Samples of seedlings (1-3 g) were taken at different time points (0, 2, 4 and 6 days), and membrane protein was extracted as described elsewhere (Schumaker and Sze, 1985). The protein concentration was determined using the bicinchoninic acid (BCA) protein assay reagent (Pierce, Rockford, Ill., USA); 15 mg per sample was electrophoretically resolved in 12% Tris-HCl-sodium dodecylsulphate (SDS) gel (Bio-Rad Laboratories) and transferred to Immobilon-P transfer membrane (Millipore, Bedford, Mass., USA). Membranes were incubated for 1.5 h with an antiserum raised against a synthetic peptide corresponding to the putative hydrophilic loop IV of the AVP1 protein (Rea et al., 1992) or with a polyclonal antiserum raised against *Arabidopsis* P-ATPase (Bouche-Pillon et al., 1994). After 1.5 h of incubation with a secondary antibody conjugated with alkaline phosphatase, the membranes were treated with a nitroblue tetrazolium-5-bromo-4-chloroindol-3-yl phosphate (NBT/BCIP) substrate solution (Roche, Indianapolis, Ind., USA) for staining.

pAVP1:GUS construct. DNA from Bac (F7H2) containing the AVP1 promoter region was employed to amplify a 1.7-kb fragment upstream to the ATG codon using the following primers: sense, 5'GCTCTAGACGTTTACCACACCAGT-CACCAC3' (SEQ ID NO: 20) with an XbaI restriction site at the 5' end; antisense, 5'CGGGATCCCTTCTCTCCTCCG-TATAAGAGA3' (SEQ ID NO: 21) with a BamHI restriction site at the 5' end. The amplified ~1.7-kb AVP1 promoter was ligated to the pGEM-T vector (Promega, Madison, Wis., USA), sequenced, and then subcloned into the XbaI/BamHI site of the pBC308 vector in front of the GUS open reading frame (Xiang et al., 1999). The vector pBC308 contains the Bar gene (phosphinothricin acetyltransferase) for selection with the herbicide phosphinothricin (BASTA).

Transformation and selection. The construct was transformed into *Agrobacterium tumefaciens* strain GV3101, and then introduced into *A. thaliana* Col-0 ecotype via the floral dip method (Clough and Bent, 1998). Plants transformed with the pAVP1:GUS cassette were seeded in soil and selected by spraying with BASTA (T1). Seeds obtained from self-pollinated transformants (T2) were scored again for herbicide resistance on soil. Complete BASTA resistance identified homozygous pAVP1::GUS plants of the T3 progeny.

Results and Discussion

Figure 6:
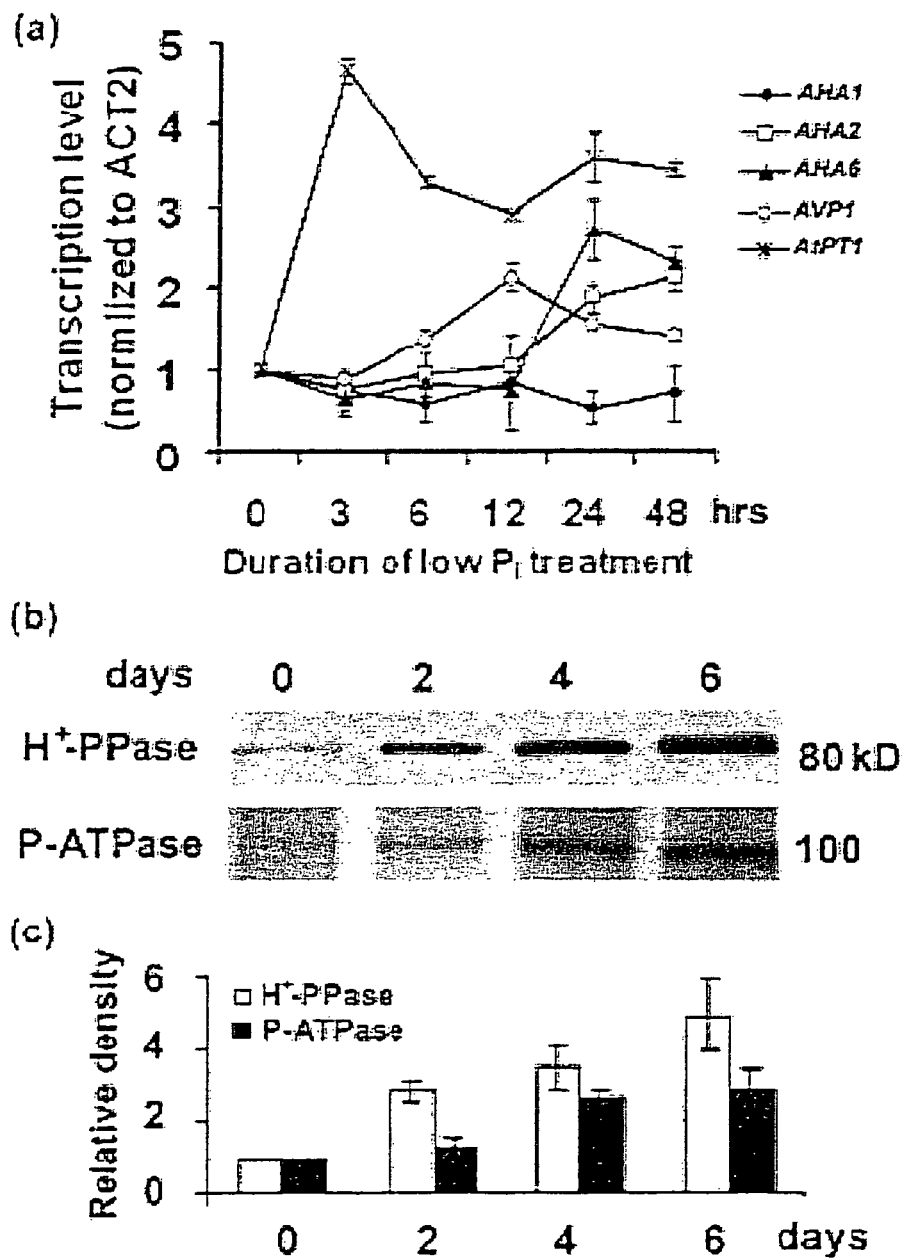
FIG. 6A is a graph showing quantitative RTF-PCR time points of AHA1, AHA2, AHA6, AVP1 and AtPT1 from wild-type (WT) plants grown under low Pi for 0-48 h. The relative mRNA levels were normalized to ACT2. Values are the means±standard deviation, n=3.
FIG. 6B is a image showing immunoblot time points of membrane proteins isolated from WT plants grown under low Pi for 0-6 days and probed with antisera to $H^+$-pyrophosphatase and P-ATPase.
FIG. 6C is a bar graph showing the relative densities of $H^+$-pyrophosphatase and P-ATPase in FIG. 6B quantified with Bio-Rad Quantity One software. Values are the means±standard deviation of three independent experiments.

The transcription and translation of AVP1 and P-ATPases (also known as "Autoinhibited $H^+$-ATPases," or AHAs), normally expressed in roots (Arango et al., 2003; Gaxiola et al., 2007) under limiting Pi conditions, were monitored. AVP1 and representative AHA mRNA abundance was assessed in wild-type *Arabidopsis* plants transferred to limiting Pi conditions by quantitative RTF-PCR. AVP1 mRNA induction peaked 12 h after the transfer of the seedlings to limiting Pi, AHA1 showed no change, and both AHA2 and AHA6 expression peaked 12 h after AVP1 (FIG. 6A). Transcription of the phosphate transporter AtPT1, which is induced under low-phosphate conditions (Muchhal et al., 1996), was up-regulated within 3 h of limiting Pi conditions (FIG. 6A). The induction of AVP1 expression by limiting Pi was confirmed with an AVP1 promoter-β-glucuronidase (AVP1::GUS) reporter transformant. This behavior is consistent with the presence of potential cis regulatory Pi response elements in the 1.7-kb promoter region used to generate the AVP1::GUS reporter (i.e. one PRH1 element at position −540; two TC elements at positions −79 and −103). These elements are present in genes whose expression has been shown to be up-regulated under limiting Pi conditions (reviewed in Hammond et al., 2004). Western blots of microsomal fractions probed with polyclonal antibodies raised against AVP1 and $H^+$-ATPase (FIG. 6B), and the relative densities of each confirmed expression (FIG. 6C), showed that the abundance of both $H^+$ pumps was increased fourfold and twofold, respectively, by Pi starvation. These results suggest that increased AVP1 expression precedes an increase in the abundance of AHA2 and AHA6$H^+$-ATPases.

Example 6

AtAVP1Ox Root Systems Respond More Vigorously than Controls when Exposed to Limiting Pi Conditions Materials and Methods

*Arabidopsis* growing conditions. The control *Arabidopsis* plants and AVP1OX plants (Gaxiola et al., 2001) used in this work were of the Col-0 ecotype. Seeds were surface sterilized and imbibed overnight at 4° C. before being sown on agar medium, or soil, or rock wool for hydroponic growth. For plants grown on agar, half-strength Murashige and Skoog (MS) medium (Murashige and Skoog, 1962) and Pi-free medium (Estelle and Somerville, 1987; Hartel et al., 2000) were used with 1% sucrose and 0.8% or 1% agar (Micropropagation/Plant Tissue Culture Grade, PhytoTechnology Laboratories, Shawnee Mission, Kans., USA). Pi-free medium contains 20 mM 2-(N-morpholino) ethanesulphonic acid (MES) (pH 5.8), 5.0 mM $KNO_3$, 2.0 mM $MgSO_4$, 2.0 mM $Ca(NO_3)_2$, 50 µM iron ethylenediaminetetraacetate (Fe-EDTA), 70 µM $H_3BO_3$, 14 µM $MnCl_2$, 0.5 µM $CuSO_4$, 1.0 µM $ZnSO_4$, 0.2 µM $NaMoO_4$, 10 µM NaCl and 0.01 µM $CoCl_2$. The Pi concentration was adjusted with $KH_2PO_4$. All experiments were performed with agar (PhytoTechnology Laboratories) that had no detectable trace Pi contamination, as determined by the method of Murphy and Riley (1962).

Lateral root, root length and root hair measurements. Root lengths were measured directly with a ruler. The lateral root number and the root hair number were counted under an Olympus SZ40 stereomicroscope (Tokyo, Japan). Root hair photographs were taken and printed, and the root hair lengths on the photographs were measured with a ruler. The final values were converted to the actual size of the root hair.

Results and Discussion

To examine whether the root systems of AtAVP1 OX plants were capable of responding to low Pi, control and AtAVP1 OX seeds were germinated under Pi-deficient (10 µM) conditions and their root development was analyzed. AtAVP1 OX seedlings developed more robust root systems than wildtype controls under Pi limitation. At 20 days, AtAVP1 OX roots were longer and had developed an average of seven more lateral roots than controls (P<0.01). Root hairs were also 2.5-fold larger and 1.5-fold denser than those of controls under Pi-deficient conditions (P<0.01), increasing the absorptive area of the roots. Primary root apical cell proliferation was monitored in control and AtAVP1 OX plants germinated under Pi-deficient and Pi-sufficient conditions using a CycB1::CDBGUS reporter associated with meristem activity/indeterminacy (Li et al., 2005). Cell proliferation, a result of meristem activity, in both AtAVP1OX and wild-type plants was curtailed in Pi-deficient conditions, but the switch to determinate growth, indicated by a loss of CycB1::CDB-GUS activity, was delayed for 3-4 days in AtAVP1 OX plants.

Example 7

AtAVP1OX Plants Exhibit Enhanced Pi Uptake and Enhanced Rhizosphere Acidification Under Pi Deficiency Materials and Methods

*Arabidopsis* growing conditions. *Arabidopsis* was grown as described in Example 6. For hydroponically grown plants, the conditions described by Gibeaut et al. (1997) were followed.

Root acidification. Plants were germinated in half-strength MS medium for 7 days, transferred to low-Pi medium as described above with 1 mM MES, pH 6.8 and 0.04 g/L bromocresol purple, and incubated for 10 days. The pH change was visualized via changes in medium color. Comparisons were made with a colour bar generated by documenting the color change of bromocresol purple in the same medium at specific pH values.

Pi uptake determination. Pi uptake experiments were performed in 125-mL flasks wrapped with aluminium foil. Plants grown hydroponically were used 2 weeks after bolting. After 2 days of incubation in distilled water, the plants were transferred to the flasks filled with 120 mL of medium supplemented with 50 µM Pi. The solution volume was maintained by adding distilled water every 4 h. The Pi concentrations in the medium were determined at 8-h increments for 96 h using the method of Murphy and Riley (1962). This method can determine Pi concentrations as low as 1 µM in seawater, and the salt error is less than 1%.

Pi determination. Plant samples were placed in glass scintillation vials and dried at 70° C. for 72 h. The fresh and dry weights were determined on an analytical balance. The samples were ashed at 500° C. for 6 h. The ash samples were dissolved in 1 N HCl, and the Pi contents were determined using a colorimetric method (Murphy and Riley, 1962).

Results and Discussion

The more robust root systems developed by AtAVP1 OX plants would be expected to increase the acidification of Pi-deficient medium, resulting in more efficient scavenging of Pi. To test this hypothesis, wild-type and AtAVP1 OX plants were transferred from Pi-sufficient to Pi-deficient medium. A visual examination of the plates showed that AtAVP1OX plants had a greater capacity than wild-type controls to acidify the medium, as indicated by the intense yellow color of the pH indicator dye. Rhizosphere acidification was completely inhibited in wild-type and AtAVP1OX plants by 1 mM vanadate, consistent with the inhibition of plasma membrane $H^+$-ATPase activity (Yan et al., 2002). Enhanced Pi uptake, measured as Pi depletion from defined hydroponic medium, was visible in both AtAVP1-1 and AtAVP1-2 overexpression transformants within 8 h of incubation, with AtAVP1-1 exhausting the available Pi almost 30 h earlier than AtAVP1-2. Total depletion of Pi by control plants was not observed at any time point.

AtAVP1OX plants also exhibited enhanced growth and Pi uptake when grown on solid Pi-deficient medium (Table I). AtAVP1OX seedlings germinated and grown in Pi-deficient medium for 20 days exhibited 1.6-fold more root and 1.3-fold more shoot biomass than controls (P<0.01). The Pi content (per plant) was 1.4-fold higher in AtAVP1OX plants than in controls (P<0.01), suggesting that AtAVP1OX plants acquire more Pi and grow accordingly (Gilooly et al., 2005; Hermans et al., 2006). Consistent with the Pi limitation of organismal growth, the Pi content (mmol/g dry weight) of AtAVP1 OX plants grown either at normal or restrictive Pi conditions was no different from controls (Table I).

Example 8

AtAVP1Ox Plants Develop Larger Shoots when Grown in Low-Pi Soil

Materials and Methods

*Arabidopsis* growing conditions. *Arabidopsis* was grown as described in Example 6. The composition and pH of the natural low-Pi soil used were analyzed by the Soil Nutrient Analysis Laboratory of the University of Connecticut (pH 6.1; P, 0.5 p.p.m.; K, 123 p.p.m.; Ca, 467 p.p.m.; Mg, 74 p.p.m.; soil texture classification, sandy loam). Pi-free medium with different $KH_2PO_4$ concentrations was used to water plants grown in low-Pi soil. Plants were grown in growth chambers with a 16-h light/8-h dark cycle at 21° C. For rock phosphate experiments, plants were grown in sand with a 1:1000 w/w $P_2O_5$/sand ratio as the only source of Pi, and flooded regularly with Pi-free medium.

Leaf area. The rosette leaves were carefully excised with a scalpel blade, and the leaf areas were measured with a Li-Cor 4100 area meter (Lincoln, Nebr., USA).

Results and Discussion

To determine whether the enhanced root systems seen in AVP1 OX plants confer

TABLE I

Effect of Pi availability on growth and Pi content of AtVVP1OX transgenic and Col-0 plants[a]

| Genotype & conditions | Root FW (mg) | Shoot FW (mg) | Root:shoot | Total P (content (μg/plant) | Total P content (mmol/g DW) |
|---|---|---|---|---|---|
| 1 mM P | | | | | |
| Col-0 | 0.79 ± 0.27 | 3.77 ± 0.72 | 0.21 ± 0.043 | 3.75 ± 0.41 | 0.071 ± 0.013 |
| AVP1-1 | 1.25 ± 0.46** | 4.38 ± 0.92* | 0.28 ± 0.066** | 4.60 ± 0.12** | 0.065 ± 0.004 |
| AVP1-2 | 1.33 ± 0.58** | 4.46 ± 115* | 0.29 ± 0.076** | 5.26 ± 0.10** | 0.076 ± 0.001 |
| 10 μM P | | | | | |
| Col-0 | 0.83 ± 0.20 | 2.42 ± 0.59 | 0.33 ± 0.072 | 0.30 ± 0.04 | 0.008 ± 0.004 |
| AVP1-1 | 1.30 ± 0.33** | 2.81 ± 0.25* | 0.47 ± 0.131** | 0.37 ± 0.05** | 0.007 ± 0.003 |
| AVP1-2 | 1.39 ± 0.40** | 3.63 ± 0.45** | 0.42 ± 0.111* | 0.44 ± 0.04** | 0.008 ± 0.002 |

[a]Plants were grown on vertical agar plates containing nutrient medium with either normal Pi (1 mM) or low Pi (10 μM) for 20 days. Root and shoot fresh weight (FW) were determined. Values shown represent the mean of 16 seedlings ± sd. 20 days old plants were harvested to determine dry weights and Pi contents. Values shown represent the mean ± sd of three independent experiments with 50 plants per line per experiment.
*indicates P < 0.05,
**indicates P < 0.01.

an advantage to plants grown in natural soils, control and AtAVP1OX lines were germinated and grown in natural low-Pi (~15 μM) soil. The growth of all plants was delayed compared with normal conditions (data not shown). However, as shown previously under Pi-sufficient conditions (Li et al., 2005), AtAVP1 OX plants developed more leaves with greater surface areas than their wild-type counterparts at all stages of growth and, when scored at 50 days post-germination, AtAVP1-1 and AtAVP1-2 had six- and twofold greater leaf areas than controls, respectively (P<0.01). This suggests that the over-expression of AVP1 results in enhanced Pi scavenging from natural low-Pi soils. Similarly, AtAVP1OX plants outperformed controls in a sandy medium supplemented with insoluble rock phosphate ($P_2O_5$) as the only source of Pi, and developed an average of 2.3-fold more shoot biomass (P=0.01).

Example 9

Double Transgenic Plant with 35S AVP1 and 35S AtNHX1

Overexpression of the pyrophosphate-energized vacuolar membrane proton pump AVP1 likely increases the availability of $H^+$ in the lumen of the vacuole, and the AtNHX1 $Na^+/H^+$ antiporter uses these $H^+$ to sequester $Na^+$ cations into the vacuole. Therefore, higher expression of these transporters likely maximizes the sequestration capability of the vacuole. To generate transgenic Arabidopsis plants that overexpress both genes AVP1 and AtNHX1, T3 35S AVP1 plants are used as females and T3 35S AtNHX1 plants are used as males. Female plants are hand-emasculated and anthers from freshly opened flowers of donor plants are harvested. With these anthers the emasculated plants are pollinated by touching the anthers onto the stigmas. The pollinated flowers are labeled and any remaining opened or unopened flowers from the same female plant are removed to avoid any confusion at harvest. The harvested seeds are sterilized using a 50% sodium hypochloride solution and mixed vigorously for 5 minutes and rinsed with water thoroughly. The sterilized seeds are stored in soft agar over night at 4° C. Then they are sprinkled onto solidified kanamycin-hygromycin selective medium. The 35S AVP1 construct has the neomycin phosphotransferase II gene that confers kanamycin tolerance in plants while the 35S AtNHX1 construct has a modified hygromycin B phosphotransferase that confers hygromycin tolerance in plants. The resistant seedlings are transplanted into soil and to the hydroponic media to be tested for their salt-tolerant phenotype. A transgenic Arabidopsis thaliana plant to overexpress the A. thaliana gain-of-function mutant gene AVP1-D (Zhen, Kim and Rea, 1997) is engineered using the same double tandem enhancer of the 35S promoter described above (Topfer et al., 1987). Plants overexpressing the gain of function mutant gene will likely show an enhanced phenotype. These plants are characterized in parallel with the 35SAVP1, 35S AtNHX singles and doubles transgenics. The A. thaliana gain-of-function mutant gene AVP1-D is subcloned into plasmid pRT103 carrying the 35 S promoter and the polyadenylation signal of CaMV (Topfer et al., 1987). A HindIII fragment containing the chimeric 35SAVP-D gene is subcloned into pBIBhyg (Becker, 1990). The resulting T-DNA vector is transformed into Agrobacterium tumefaciens strain GV3101 via electroporation, and used for subsequent vacuum infiltration of Arabidopsis thaliana ecotype Columbia (Bechtold et al., 1993). Integration is confirmed on Southern blots of T3 plants and expression monitored on Northern blots of positive T3 plants.

Example 10

Comparative Transport Study with Vacuoles from the Roots of Wild-Type and 35S AVP1 Transgenic Plants The purpose of this study is to determine if the vacuoles of 35S AVP1 transgenic plants show a higher proton transport activity dependent on pyrophosphate. These determinations are done with root and shoot tissues separately from plants grown hydroponically. The transgene could show a tissue-specific regulation despite the 35S promoter.

In order to compare the PPi-dependent $H^+$ translocation activities of wild-type and 35S AVP1 transgenic plants sealed tonoplast-enriched vesicles from roots and leaves of the above plants are prepared. The homogenization and differential centrifugation procedure described by Rea and Turner (Rea et al., 1990) is followed. $H^+$ translocation is assayed fluorimetrically using acridine orange (2.5 μM) as transmembrane pH difference indicator in assay media containing vacuole membrane-enriched vesicles as described by Rea and coworkers (Zhen, Kim and Rea, 1997). The assay media contains 300 µM Tris-PPi, 50 mK KCl, 2.5 µM acridine orange, 5 mM Tris-Mes (pH 8.0). Intravesicular acidification is triggered with the addition of 1.3 mM $MgSO_4$ and terminated with the addition of the protonophore FCCP at 2.5 µM. Fluorescence is measured at excitation emission wavelengths of 495 and 540 nM, respectively, at a slit width of 5 nM (Zhen et al., 1994). A further test to support that the $H^+$ translocation is AVP1 driven is the addition of the specific inhibitor aminomethyledediphosphonate (Zhen et al., 1994).

Example 11

Determination of the $Na^+/K^+$ Ratios in Leaves and Stems of the Transgenic Plants These measurements indicate to whether or not the transgenic plants described herein have an increased vacuolar capacity to sequester $Na^+$ in their leaves cells or elsewhere. Toxic concentrations of NaCl build up first in the fully expanded leaves where NaCl is compartmentalized in the vacuoles. Exposure to NaCl can disrupt or reduce $K^+$ uptake leading to $K^+$ deficiency and growth inhibition (Wu et al., 1996). A cytosolic consequence of reduced $K^+$ content and high $Na^+$ is the inhibition of important enzymes. An example of such enzymes is the 3'(2'), 5'-bisphosphate nucleotidase of yeast whose activity is more sensitive to $Na^+$ when $K^+$ content is low (Murguia et al., 1995). To determine the $Na^+/K^+$ ratios in leaves and stems wild-type and 35S AVP1/35S AtNHX1 double and single transgenics in hydroponic conditions (Gibeaut et al., 1997) are grown. NaCl is added to the growth media in a stepwise fashion starting with 50 mM up to 250 mM. At every point the rosette and the stems of the treated plants are collected and their weight is determined. The samples are dried out in an oven at 80° C. and their dry weight is determined. The dry samples are boiled in a determined volume of water and their $Na^+$ and $K^+$ contents determined via atomic absorption spectrophotometry (Apse et al., 1999; Gaxiola et al., 1992).

Example 12

Determination of Whether 35S AVP1 Transgenic Plants are Larger Because their Cells are Larger or Because they have More Cells, or Both The shoot meristems labeling index is compared with one of the wild-type plants. Morphological and anatomical observations measuring and counting cells of leaves, roots and stems are performed. To determine if 35S AVP1 transgenic plants are larger because they have more cells, their shoot meristems labeling index is compared with the one of wild-type plants. To measure the DNA synthesis or cell proliferation 5-Bromo-2'-deoxy-uridine (BrdU) that can be incorporated into DNA in place of thymidine is used. Cells that have incorporated BrdU into DNA are detected using a monoclonal antibody against BrdU monoclonal antibody and an anti-mouse Ig-alkaline phosphatase as a second antibody. The bound anti-BrdU monoclonal antibody is visualized by light microscopy and the ratio between DAPI stained and BrdU positives established. The protocol is a modification of the one published by Chiatante and coworkers (Levi et al., 1987) and the BrdU labeling and detection kit II from Boehringer Mannheim. The plants are exposed for different times to the BrdU labeling medium and then fixation, paraffin embedding and sectioning is performed as described by Meyerowtz and coworkers (Drews et al., 1988). For observation of leaf tissue, fresh tissues are embedded in 5% agarose and slice them with a microslicer. For primary root observation, seedlings are fixed for 4 hr in 50% ethanol, 5% acetic acid, and 3.7% formaldehyde at room temperature, dehydrate them in graded ethanol series, permeate them with xylene, and infiltrate them with paraffin. Eight-micrometer sections are stained with 0.05% toluidine blue and cells are counted under a microscope. As an alternative for the visualization and determination of cell size the method described by Greenberg and coworkers (Rate et al., 1999) is followed.

Example 13

Isolation of Mutants in the Transporters

Genetic Approaches are Very Powerful in Analyzing Complex Biological Traits (Serrano, 1994) Reverse genetics is a very important new tool for plant biologists. The generation of a good collection of tagged knockouts by Sussman and coworkers (Krysan et al., 1996) has opened a very important avenue for the analysis of gene disruptions in *Arabidopsis*. The *Arabidopsis* Knock-out Facility of the University of Wisconsin Madison is used to search among the 60, 480 *Arabidopsis* (ecotype WS) lines that have been transformed with the T-DNA vector pD991 for the presence of T-DNA inserts within AtCLC-c, AtCLC-d, AVP1, AtNHX1 and their homologues. The phenotypes of the above knock-outs will shed light towards the understanding of the physiological roles of these transporters in normal and stress conditions. An initial characterization of the knockout plants includes testing for their salt tolerance and their $Na^+/K^+$ ratios. The generation of double knock-outs via crosses help to further understand the interaction among the transporters as well as the crosses with the 35S AVP1 and the 35S AtNHX1 transgenic plants.

To search for *Arabidopsis* knock-out PCR primers are designed following the guidelines detailed in the University of Wisconsin web site. Tested primers are sent to UW-Madison, where 62 PCR reactions that are sent to us for Southern blot analysis are performed. Positive PCR products are sequenced. If the sequence reveals that there is a T-DNA inserted within the gene the gene specific primers are sent for another set of PCR reactions in order to determine which of the 9 possible pools of 225 contains the knockout. After identifying the pool of interest, 25 tubes of seeds are screened for the individual plant carrying the T-DNA knock-out.

Example 14

Cation Detoxification in Plant Cells

The studies described herein together with other evidence strongly indicate that yeast and plants share pathways and signals for the trafficking of vesicles from Golgi network to the vacuole (Gaxiola et al., 1999; Marty, 1997; Bassham et al., 1998). Without wishing to be bound by theory, it is likely that in both systems a prevacuolar compartment is a dynamic entity that detoxifies the cytoplasm from toxic cations and delivers its cargo either to the vacuole, or directly to the cell exterior. Both the Gef1 chloride channel and Nhx1 $Na^+/H^+$ exchanger have been localized to the yeast prevacuolar compartment (Gaxiola et al., 1999). The behavior of the Gef1-GFP chimera in yeast cells in vivo have been monitored indicating that its localization varies depending the environmental conditions. Furthermore, it has been shown that two of the four *A. thaliana* CLC chloride channel genes CLC-c and -d are capable of suppressing gef1 mutant phenotypes implying a similar localization (Gaxiola et al., 1998). In order to understand how and where this cation detoxification takes place in plant cells the intracellular localization of GFP chimeras of AVP1, AtNHX1 and AtCLC-c and -d (Hong et al., 1999) is monitored in vivo. Confocal microscopy is also used to address colocalization of the different transporters. For this purpose HA-tagged versions or antibodies of the transporters under study are required (Guiltinan et al., 1995; Jauh et al., 1999; Mullen et al., 1997).

For the constructions of the GFP-chimeras the soluble versions of GFP with improved fluorescence in *A. thaliana* reported by Davis and Viestra (Davies, S. J. and Viestra, R. D., "Soluble derivatives of green fluorescent protein (GFP) for use in *Arabidopsis thaliana* (1998)) are used. Two types of GFP-chimeras are made, namely a set under the regulation of the native promoter and another set under the regulation of the 35S promoter. The resulting T-DNA vectors containing the GFP-chimeras are transformed into *Agrobacterium tumefaciens* strain GV3101 via electroporation, and used for subsequent vacuum infiltration of *Arabidopsis thaliana* ecotype Columbia (Bechtold et al., 1993). For the hemagglutinin (HA) epitope tagging a PCR strategy designed for yeast but modified to tag plant genes expressed in yeast vectors is used. Futcher and coworkers designed vectors containing the URA3 yeast gene flanked by direct repeats of epitope tags (HA) (Schneider et al., 1995). Via PCR the tag-URA3-tag cassette is amplified such that the resulting PCR fragment possess homology at each end to the gene of interest. In vivo recombination in yeast is then used to direct the integration of the PCR-chimera to the plasmid carrying the plant ORF of interest, transformants are selected by the URA$^+$ phenotype. The URA3 gene is "popped out" when positive transformants are grown in the presence of 5-fluoro-orotic acid. The vector carrying the plant gene has a selection marker different than the URA3 gene.

Example 15

Further Applications of the Yeast Model

Gain of function mutants of the AtNHX that enhance salt tolerance of transgenic plants are generated using the yeast system. This is accomplished by mutagenizing the cloned gene to make a mutant library. This library is used to transform the salt sensitive yeast mutant ena1 and clones with an enhanced salt tolerant phenotype will be identified and retested. The other genes that show similarity to the AtNHX1 gene reported by the *Arabidopsis* Genome Initiative (AGI) are expressed in yeast. It is likely that some of these AtNHX1 homologues are plasma membrane transporters, so their function in yeast should be pH dependent. Thus the precise composition and pH of the medium used for screening is crucial for success. Identification of plasma membrane transporters helps to engineer plants with an enhanced salt tolerance due to a reduced sodium uptake. In addition, plant cDNA expression libraries in yeast are used to identify other families of transporters involved in NaCl detoxification.

To generate gain of function mutants of the AtNHX a method for introducing random mutations developed by Stratgene (Epicurian Coli XL1-Red competent Cells Cat#200129) is used. The method involves the propagation of a cloned gene into a strain deficient in the three primary DNA repair pathways. The random mutation rate in this strain is about 5000-fold higher than that of wild-type. A library of the mutated AtNHX gene is transformed into the ena1 yeast mutant and screened for salt tolerance. Yeast transformation is performed as described by Schiestl and coworkers (Gietz et al., 1992). An alternative to the XL1-Red random mutagenesis strategy is a PCR approach described by Fink and coworkers (Madhani et al., 1997). To test ATNHX1 homologs the same strains and conditions used for AtNHX1 (Gaxiola et al., 1999) are used initially. However, if these screening strains and/or conditions do not work new ones are worked out. It is likely that when dealing with plasma-membrane AtNHX1 homologues pH conditions of the assay media are crucial.

Example 16

Hydroponic Culture of Transgenic Plants

The reduced availability of fresh water for standard agriculture may force the use of alternative agricultural arts. It is conceivable that with salt tolerant crops the use of hydroponics with seawater will create a new era in crop production. As described herein, conditions for hydroponics culture of *Arabidopsis* plants have been established and their performance in increasing concentrations of NaCl in their media have been tested. Transgenic plants are challenged with a commercial seawater formula that contains the complete ionic composition present in the oceans.

35SAVP1, 35 SAtNHX1 single and double transgenics are grown together with wildtype *Arabidopsis thaliana* plants under hydroponic conditions for four weeks in a short day illumination cycle (Gibeaut et al., 1997). Then every four days an equivalent to 50 mM NaCl of Tropic Marin sea salt is added. This artificial sea water mix includes all of the other major and trace elements present in real sea water. Growth is monitored and physiological parameters, such as sodium content and distribution is determined as described in previous sections.

Example 17

Tomato Plants Over-Expressing the *Arabidopsis* Type I H$^+$-pyrophosphatase Outperform Controls Under Pi-Limiting Conditions Materials and Methods Tomato transformation. The tomato homologues of AVP1 and AtNHX1 are isolated and the corresponding chimeras to overexpress them are constructed (Bidone et al., 1998; Burbidge et al, 1997). The genes are introduced via *Agrobacterium*-mediated infection of calli. Tissue culture methods are used to regenerate transformed plants. The plants are assayed for salt tolerance as well as physiological parameters, such as sodium content and distribution. Increasing the salt-tolerance of tomato and rice plants will likely have important economic repercussions. A positive result indicates that the sequestration model described herein is also applicable to an important crop. Tomato transformation with 35S AVP1 and with 35S AtNHX1 constructs is performed as described by McCormick (McCormick, 1991). T0 and T1 transgenics are analyzed by polymerase chain reaction and DNA gel blotting for the presence and copy number of AVP1 and AtNHX1 transgenes. Heterozygous and homozygous plants are identified after segregation analysis of each transcend within T1 seeds. Homozygous plants are assayed for salt tolerance and as well as physiological parameters, such as sodium content and distribution. Degenerated oligos based on conserved sequences present in AVP1 and AtNHX1 homologues are designed. These degenerated primers are used in RT-PCR reactions with cDNAs made from poly(A) RNA from tomato. The resulting PCR fragments are used as probes to isolate the full length cDNA clones from commercial libraries (i.e. Stratagene Cat#936004). A similar strategy was described by Caboche and coworkers (Quesada et al., 1997). Detailed method to transform AVP1D (the E229D gain-of-function mutant of the AVP1 gene that has a coordinated increase of both PPi hydrolytic activity and PPi-dependent $H^+$-translocation; Zhen, Kim and Rea, 1997) into tomato plant was described in Park et al., 2005, and incorporated herein by reference.

Tomato growing conditions. Tomato (*Lycopersicon esculentum* Mill. cultivar Money Maker) control and AVP1D over-expressing plants have been described elsewhere (Park et al., 2005). Seeds were surface sterilized and imbibed overnight at 4° C. before being sown on half-strength MS medium. Ten-day-old seedlings were transferred to pots containing 1 kg of natural low-Pi soil (see above) mixed with 44, 100 or 400 mg $NaH_2PO_4$. Tomato pots were kept in plastic bags to prevent loss of Pi. Plants were randomly placed in the glasshouse. Pi-free medium, described above, was used to water the plants every 2 weeks.

Results and Discussion

The effects of the overexpression of *Arabidopsis thaliana* proton transporters (AVP1 and AtNHX1) in more agriculturally important plants such as tomato are examined. There is a high degree of identity at the amino acid level between the type I $H^+$-pyrophosphatases across the plant kingdom (Maeshima, 2000; Drozdowicz and Rea, 2001), suggesting that AVP1 from one species would be functional in another species. Transgenic tomatoes over-expressing the E229D gain-of-function mutant (AVP1D) of the *Arabidopsis* $H^+$-pyrophosphatase (LeAVP1DOX) develop more robust root systems and are resistant to imposed soil water deficits (Park et al., 2005). As was seen with AtAVP1OX, both LeAVP1D-1 and LeAVP1D-2 over-expression lines developed larger shoots, root systems and fruits than controls when grown under Pi-deficient conditions. Although, at 44 p.p.m. $NaH_2PO_4$, neither controls nor LeAVP1DOX lines developed fruits, at 100 p.p.m. $NaH_2PO_4$, both LeAVP1D-1 and LeAVP1D-2 lines developed a larger quantity of bigger fruits than controls. The root and shoot dry weights of plants grown in the presence of 100 p.p.m. $NaH_2PO_4$ were, on average, 13% and 16% higher (P<0.01), respectively, in LeAVP1DOX plants than in controls. Furthermore, under the same low-Pi conditions, fruit dry weight data and Pi content per plant were 82% and 30% higher (P<0.01), respectively, than in controls (Table II). Here again, there was no statistically significant difference in the normalized Pi content (mmol/g dry weight) of control and LeAVP1DOX roots or shoots grown under three limiting Pi conditions (Table II).

TABLE II

Effect of Pi availability on growth and Pi content of LeAVP1DOX and control plants[a]

| Genotype & conditions | Root DW (g) | Shoot DW (g) | Fruit DW (g) | Root:shoot | Total P content (mg/plant) |
|---|---|---|---|---|---|
| 400 ppm | | | | | |
| LeWT | 1.16 ± 0.07 | 13.07 ± 0.76 | 4.87 ± 0.36 | 0.08 ± 0.01 | 11.33 ± 1.08 |
| LeAVP1D-1 | 1.26 ± 0.08* | 14.50 ± 0.40** | 4.81 ± 0.21 | 0.09 ± 0.02 | 11.60 ± 1.11 |
| LeAVP1D-2 | 1.34 ± 0.15* | 14.70 ± 0.80** | 5.23 ± 0.15* | 0.09 ± 0.02 | 13.12 ± 1.16* |
| 100 ppm | | | | | |
| LeWT | 1.17 ± 0.07 | 8.45 ± 0.39 | 0.39 ± 0.15 | 0.14 ± 0.02 | 7.76 ± 0.92 |
| LeAVP1D-1 | 1.31 ± 0.06** | 9.89 ± 0.53** | 2.34 ± 0.23** | 0.13 ± 0.02 | 9.63 ± 1.15** |
| LeAVP1D-2 | 1.39 ± 0.12** | 10.22 ± 0.71** | 1.94 ± 0.28** | 0.14 ± 0.02 | 10.54 ± 1.21** |
| 44 ppm | | | | | |
| LeWT | 0.22 ± 0.02 | 0.70 ± 0.08 | — | 0.36 ± 0.04 | 0.76 ± 0.08 |
| LeAVP1D-1 | 0.33 ± 0.05** | 0.75 ± 0.06 | — | 0.47 ± 0.10 | 0.97 ± 0.06** |
| LeAVP1D-2 | 0.42 ± 0.03** | 1.18 ± 0.16** | — | 0.39 ± 0.05 | 1.46 ± 0.12** |

| Genotype & conditions | Total P content (mmol/g DW) | Root P content (mmol/g DW) | Shoot P content (mmol/g DW) |
|---|---|---|---|
| 400 ppm | | | |
| LeWT | 0.023 ± 0.002 | 0.021 ± 0.002 | 0.023 ± 0.002 |
| LeAVP1D-1 | 0.024 ± 0.002 | 0.021 ± 0.002 | 0.024 ± 0.002 |
| LeAVP1D-2 | 0.026 ± 0.003 | 0.024 ± 0.003 | 0.026 ± 0.003 |
| 100 ppm | | | |
| LeWT | 0.026 ± 0.002 | 0.025 ± 0.002 | 0.026 ± 0.002 |
| LeAVP1D-1 | 0.028 ± 0.005 | 0.028 ± 0.005 | 0.028 ± 0.005 |
| LeAVP1D-2 | 0.028 ± 0.005 | 0.026 ± 0.004 | 0.028 ± 0.005 |
| 44 ppm | | | |
| LeWT | 0.025 ± 0.003 | 0.023 ± 0.004 | 0.029 ± 0.01 |
| LeAVP1D-1 | 0.029 ± 0.002 | 0.031 ± 0.004 | 0.027 ± 0.01 |
| LeAVP1D-2 | 0.030 ± 0.004 | 0.028 ± 0.006 | 0.034 ± 0.009 |

[a]Dry weights and Pi contents of plants (shoots and roots) grown in natural low-Pi (~0.5 ppm P, ~15 µM P) soil amended to 400, 100 and 44 ppm $NaH_2PO_4$ were evaluated after 120 days of growth under greenhouse conditions. Values are means ± s.d., n = 8 plants per line per experiment.
— plants did not set fruit.
*P < 0.05,
**P < 0.01.

Example 18

**Over-Expression of *Arabidopsis* AVP1D Results in Enhanced Pi Nutrition in Rice**

Materials and Methods

Rice growing conditions. Rice control *Oryza sativa* var. *japonica* 'Taipei 309' and AVP1D overexpressing plants (see 'Rice transformation') were grown in sand under normal and low-Pi conditions. Rice seeds were surface sterilized and germinated in agar plates containing medium supplemented with either 1 mM or 10 µM Pi, as described above (Estelle and Somerville, 1987; Hartel et al., 2000). Ten-day-old seedlings were then transferred to pots with sand. These pots were placed in a plastic tray filled with 2 L of rice Pi-free liquid medium (modified from Yoshida et al., 1976) supplemented with either 1 mM or 10 µM Pi. Rice Pi-free liquid medium contains 1.43 mM $NH_4NO_3$, 0.51 mM $K_2SO_4$, 1 mM $CaCl_2$, 1.64 mM $MgSO_4.7H_2O$, 9.5 µM $MnCl_2.4H_2O$, 0.048 µM $(NH_4)_6Mo_7O_{24}.4H_2O$, 19 µM $H_3BO_3$, 0.15 µM $ZnSO_4.7H_2O$, 0.155 µM $CuSO_4.5H_2O$, 35.6 µM $FeCl_3.6H_2O$, 71 µM citric acid monohydrate and 1.1 mM sulphuric acid, pH 5.0. The Pi concentration was adjusted with $KH_2PO_4$. Plants grown under Pi-sufficient conditions were watered with 1 mM Pi medium, and plants grown under Pi-deficient conditions were watered with rice Pi-free medium, every 2 weeks. Plants were incubated in growth chambers with a 16-h light/8-h dark cycle at 25° C.

Hydroponic conditions. Rice plants were germinated and grown on agar plates supplemented with half-strength MS medium for 10 days, transferred into pots with sand and watered with one-eighth-strength MS medium. After 15 days of growth in sand, plants were transferred to the hydroponic system (General Hydroponics, Sebastopol, Calif., USA). The nutrients added were from General Hydroponics following their directions for 'general purpose' growth conditions. The medium was supplemented once with 10 mL of Iron Max Ac 6% (15-0-0) (Growth Products, White Plains N.Y., USA) per 120 L of hydroponic medium solution.

Rice transformation. To generate AVP1DOX rice plants, seeds from *O. sativa* var. *japonica* 'Taipei 309' were surface sterilized and germinated on LS 2.5 medium [MS medium supplemented with 2.5 mg/L 2,4-dichlorophenoxyacetic acid (2,4-D), 2 g/L casein hydrolysate and 3% sucrose, solidified with 7 g/L agar] (Abdullah et al., 1986) to initiate calli. After 2 weeks of incubation in the dark at 25° C., scutella were isolated from the starchy endosperm, transferred to fresh LS 2.5 medium and returned to the dark. Calli that formed yellowish, globular clusters were proliferated on the same medium to be used for microprojectile bombardment experiments on a Particle Delivery System (Model PDS-1000/He Biolistic, Bio-Rad Laboratories).

DNA of the following plasmids [pDM302 (Cao et al., 1992)+pRG389=pRT103 (Topfer et al., 1987) with AVP1D cDNA (Zhen, Kim and Rea, 1997)] was precipitated onto 1-µm gold particles, as described previously (Kausch et al., 1995). The DNA-coated particles were pelleted by centrifugation at 500 rpm for 5 min, washed with 100% ethanol and resuspended in a final volume of 55 µL of 100% ethanol (anhydrous). The suspension was sonicated for 10 s immediately before dispensing. Ten microliters of the DNA suspension were aliquoted onto each macrocarrier and allowed to air dry. The bombardment parameters were as follows: 7584-kPa rupture discs (Bio-Rad); rupture disc to macrocarrier gap distance, 5 mm; macrocarrier fly distance, 10 mm; stopping screen to target distance, 5 cm; partial vacuum, 94.82 kPa.

Three-week-old rice scutella bombarded with pDM302+ pRG389, or pDM302, were transferred to LS 2.5 medium supplemented with 3 mg/L glufosinate at 3 days post-bombardment, and incubated in the dark at 25° C. Calli were subcultured to fresh LS 2.5 medium supplemented with 3 mg/L glufosinate at 4-week intervals and incubation was continued as described. Glufosinate-resistant calli were transferred to rice shoot regeneration medium (4.4 g/L MS salts, 2.0 mg/L 6-benzylaminopurine, 30 g/L sucrose, 7 g/L TC agar), and regenerated shoots were transferred to full-strength MS medium with 2% sucrose and 0.7% agar. Positive candidates were confirmed by Southern blot analysis.

Western blot analysis. Western blot analysis was done as described in Example 5. For rice plants, seeds of control and T2 OsAVP1 DOX plants were germinated in half-strength MS medium. Microsomal fractions were isolated from 10-day-old seedlings, as described elsewhere (Schumaker and Sze, 1985). Membranes were incubated for 1.5 h with the 2E7 monoclonal antibody against V-ATPase (Ward et al., 1992).

Results and Discussion

Rice (*Oryza sativa*) is the principal staple crop for more than one-half of the world's population. It has been estimated that the world's annual rice production must increase from 618 million tons in 2005 to 771 million tons by 2030 in order to keep pace with population growth. To determine whether increased $H^+$-pyrophosphatase activity improves plant performance under Pi-deficient conditions in monocots, rice (*O. sativa* var. *japonica* 'Taipei 309') was engineered with a 35S::AVP1D cassette. AVP1 over-expression was confirmed by Western blot and relative density; vacuolar-type ATPase (V-ATPase) was not altered. The OsAVP1DOX line exhibited sustained shoot growth under Pi-deficient (10 µM) conditions, whereas the controls grew poorly. The OsAVP1DOX line tested developed more robust root systems than controls in both Pi-sufficient and Pi-deficient conditions. The dry plant biomass data confirmed that the OsAVP1DOX line grown under limiting Pi conditions developed larger roots (90%, P<0.01) and shoots (50%, P=0.01) than controls (Table III). Therefore, AVP1 over-expression in monocots and dicots results in enhanced root systems under low-Pi conditions. However, in contrast with the results of over-expression of AVP1 in *Arabidopsis* and tomato, OsAVP1DOX rice seedlings grown under Pi-sufficient conditions accumulated 18% higher Pi content (mmol/g dry weight) than controls (Table III), suggesting a different mechanism between monocots and eudicots under Pi sufficiency.

Example 19

Roots from AtAVP1OX, LeAVP1DOX and OsAVP1 DOX Lines Have Higher $K^+$ Contents and Exude Greater Amounts of Organic Acids than Controls

Materials and Methods

Aluminum treatments. For *Arabidopsis* plants, *Arabidopsis* plants were germinated in half-strength MS medium for 5 days, and then transferred to plates containing 40 µM AlPO3 as the only source of Pi; the medium pH was buffered to pH

TABLE III

Effect of Pi availability on growth and Pi content of OsAVP1DOX and control plants[a]

| Genotype & conditions | Root DW (g) | Shoot DW (g) | Root:shoot | Total P content (mg/plant) | Total P content (mmol/g DW) |
|---|---|---|---|---|---|
| 1 mM P | | | | | |
| Control | 0.059 ± 0.008 | 0.162 ± 0.017 | 0.366 ± 0.042 | 0.72 ± 0.09 | 0.105 ± 0.01 |
| OsAVP1D-2 | 0.083 ± 0.020** | 0.178 ± 0.024 | 0.469 ± 0.063* | 1.03 ± 0.11** | 0.128 ± 0.01* |
| 10 μM P | | | | | |
| Control | 0.033 ± 0.009 | 0.083 ± 0.021 | 0.389 ± 0.023 | 0.051 ± 0.009 | 0.014 ± 0.002 |
| OsAVP1D-2 | 0.063 ± 0.012** | 0.124 ± 0.017** | 0.509 ± 0.079** | 0.089 ± 0.019** | 0.015 ± 0.003 |

[a]Seeds were germinated in plates with either 1 mM or 10 !M Pi for 10 days. Plants were transferred to sand with either 1 mM or 10 !M Pi for 25 days. Dry weights and Pi contents were evaluated. Values are means ± s.d., n = 12 plants per line per experiment.
*P < 0.05 and
**P < 0.01.

4.5 with 1 mM N-2-hydroxyethylpiperazine-N'-2-ethanesulphonic acid (HEPES).

For tomato plants, tomato plants were germinated in half-strength MS medium for 10 days, and then transferred to sand supplemented with 20 μM AlPO$_3$ as the only source of Pi; the pH was buffered to pH 5.0 with 1 mM HEPES. For rice plants, rice plants were germinated in half-strength MS medium for 10 days, transferred to pots with sand and flooded with Pi-free medium+10 μM AlPO$_3$ as the only source of Pi. The pH of the medium was buffered to pH 5.0 with 1 mM HEPES.

Quantification of organic acids. The determination of organic acids was performed as described previously (Murphy et al., 1999). Plants were grown axenically in one-fifth Hoaglands medium, pH 4.85 with a 16-h day (140 μE/mls light). Rice and tomato plants were grown at 23° C. and Arabidopsis seedlings were grown at 20° C. For assays of tomato and rice plants, 20-day-old seedlings were used. Seedlings were transferred to treatment medium (control, 10 μM Pi and 10 μM Pi+20 μM Al) for 12 h. Roots were washed once in a sterile hood for 5 min with distilled water, followed by washing with the medium to which they were to be transferred. Twenty seedlings were measured for each experiment. The experiments were repeated three times. The organic acid content was normalized to the fresh weight, and then expressed as a percentage of control levels with the percentage sum standard deviations.

$K^+$ content determination. Plants were treated in the same way as in the organic acid exudation experiment. Root $K^+$ contents were quantified using flame atomic absorption spectroscopy, as described by Murphy et al. (1999), and confirmed by inductively coupled plasma mass spectroscopy.

Results and Discussion

Pi deficiency is often a problem in tropical soils in which marginal aluminium toxicity limits agricultural production (Kochian et al., 2004). In such soils, although AVP1-dependent rhizosphere acidification can enhance Pi efficiency, it may also be expected to enhance aluminium mobilization and toxicity. Surprisingly, this is not the case. The growth of AtAVP1OX, LeAVP1 DOX and OsAVP1 DOX was assayed in medium in which AlPO$_4$ functioned as the only source of Pi. AVP1 over-expression did not result in increased sensitivity to AlPO$_4$. Only AtAVP1-1 exhibited aluminium sensitivity similar to controls. LeAVP1DOX, OsAVP1DOX and, to a lesser extent, AtAVP1-2 exhibited greater tolerance to aluminium compared with controls.

Enhanced AVP1-dependent $H^+$ extrusion appears to be charge balanced, as demonstrated by enhanced $K^+$ retention and organic acid extrusion from roots, similar to that seen in copper-challenged Arabidopsis roots (Murphy et al., 1999). Under all conditions tested, root $K^+$ contents were significantly higher (P<0.05), and approximately twice those of controls, in all AVP1OX crops. Furthermore, quantification of root organic acid exudates (citrate and malate) in AVP1OX plants grown under AlPO$_4$ stress showed higher levels of organic acid exudation in LeAVP1 DOX and OsAVP1 DOX than in controls. Organic acid extrusion has been correlated with enhanced resistance to aluminium toxicity (reviewed in Kochian et al., 2004), suggesting that the enhanced rhizosphere acidification triggered by AVP1 over-expression would not result in increased aluminium toxicity in marginal tropical soils.

Example 20

Figure 7:
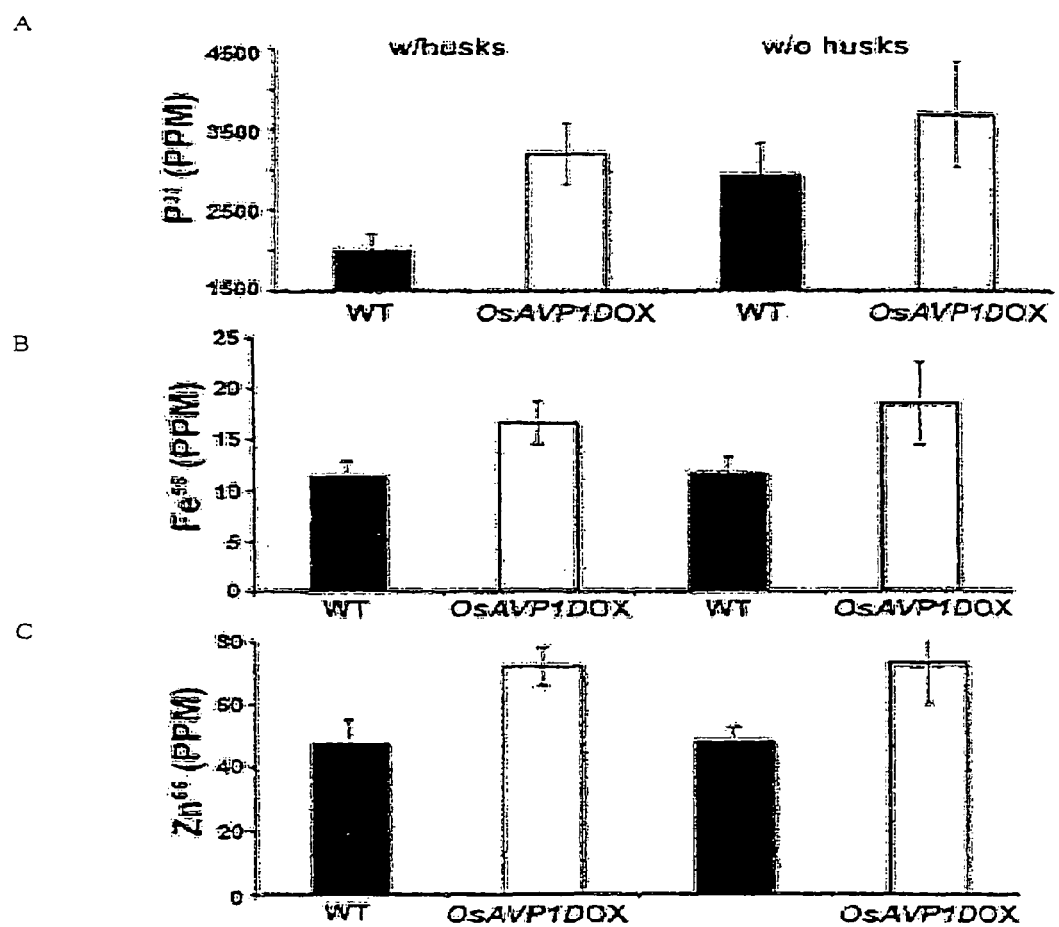
FIG. 7A-C are bar graphs showing results of ionomic analysis of rice grains from wild-type and OsAVP1DOX plants. Rice was grown under phosphorus-sufficient conditions and harvested seeds were submitted for ICP-MS analysis of 20 elements by the Purdue-NSF Ionomics facility using their standard protocols. Shown are the profiles for phosphorus ($P^{31}$), iron ($Fe^{56}$), and zinc ($Zn^{66}$). Values are shown for grains with and without husks in parts per million.

Biomass and Seed Yields are Enhanced in Both Arabidopsis and Rice Plants when Grown Under Nutrient-Sufficient Conditions The over-expression of AVP1 in Arabidopsis results in plants with significantly larger root and shoot biomasses when grown under nutrient-sufficient conditions (Li et al., 2005). Hydroponically grown OsAVP1DOX plants also developed twofold larger shoots and roots, and twofold more tillers and panicles (inflorescences), than control plants (Table IV). Furthermore, AVP1 over-expression in rice resulted in a 50% increased seed yield (Table IV). We did not observe similar increases in fruit production in LeAVP1DOX plants grown under nutrient-sufficient conditions (Table II). The differences in crop performance could be a result of the different shoot branching patterns displayed by tomato and rice (reviewed in McSteen and Leyser, 2005). It should be noted that ionic analysis of rice grains of plants grown under nutrient sufficiency showed that phosphorus, iron and zinc contents were enhanced in OsAVP1DOX plants (FIG. 7A-C).

TABLE IV

Dry weights and tiller number of OsAVP1DOX and control plants grow in normal hydroponics[a]

| Line | Dry weight | | | Numbers | | Percentage Grain-filling rates |
|---|---|---|---|---|---|---|
| | Total seeds | Shoots | Roots | Tillers | Panicles | |
| WT | 38.5 ± 8.2 | 117 ± 22 | 34.2 ± 9.0 | 45 ± 15 | 23 ± 4.7 | 82 ± 4.3 |
| OsAVP1D-1 | 61.1 ± 6.4* | 213 ± 27** | 70.6 ± 9.6** | 83 ± 12** | 42 ± 4.5** | 61 ± 16.8** |

[a]Plants were germinated and grown in agar plates supplemented with ½ strength MS medium for 10 days, then transferred into pots with sand and watered with ⅛ strength MS medium. After 15 days of growth in sand, plants were transferred to the floodand drain system (General Hydroponics, Sebastopol, CA). After 180 days of growth seed, shoot and root dry weights were determined. Tiller numbers were counted. Values are means ± s.d., n = 6, for seed dry weight: n = 3.
*P < 0.05,
**P < 0.01.

While this invention has been particularly shown and described with references to example embodiments thereof, it will be understood by those skilled in the art that various changes in form and details may be made therein without departing from the scope of the invention encompassed by the appended claims.

LIST OF NON-PATENT REFERENCES CITED

Abdullah, R., Cocking, E. C. and Thompson, J. A. (1986) Efficient plant regeneration from rice protoplasts through somatic embryogenesis. *Bio/Technology*, 4, 1088-1090.
Abel, S., Ticconi, C. A. and Delatorre, C. A. (2002) Phosphate sensing in higher plants. *Physiol. Plant.* 115, 1-8.
al-Awqati, A., *Curr. Opin. Cell. Biol.,* 7:504-508 (1995).
Antebi, A. and Fink, G. R., *Mol. Biol. Cell,* 3:633-654 (1992).
Apse, M., et al., *Science,* 285:1256-1258 (1999).
Arango, M., Gevaudant, F., Oufattole, M. and Boutry, M. (2003) The plasma membrane proton pump ATPase: the significance of gene subfamilies. *Planta,* 216, 355-365.
Ballester, R., et al., *Cell,* 59:681-686 (1989).
Ballesteros, E., et al., *Physiologia Plantarum,* 99:328-334 (1997).
Barkla, B. J., et al., *Symp. Soc. Exp. Biol.,* 48:141-153 (1994).
Bassham, D. C., et al., *Plant Physiol,* 117:407-415 (1998).
Bechtold, N., et al., C. R. *Jeances Acad. Sci. Ser. III Sci. Vie,* 316:1194-1199 (1993).
Becker, D., *Nuc. Acid Res.,* 18:203 (1990).
Bidone, S., et al., *Eur. J. Biochem.,* 253: 20-26 (1998).
Bouche-Pillon, S., Fleurat-Lessard, P., Fromont, J. C., Serrano, R. and Bonnemain, J. L. (1994) Immunolocalization of the plasma membrane $H^+$-ATPase in minor veins of *Vicia faba* in relation to phloem loading. *Plant Physiol.* 105, 691-697.
Burbidge, A., et al, *J. Exper. Botany,* 48:2111-2112 (1997).
Cao, J., Duan, X., McElroy, D. and Wu, R. (1992) Regeneration of herbicide resistant transgenic rice plant following microprojectilemediated transformation of suspension culture cells. *Plant Cell Rep.* 11, 589-591.
Clough, S. J. and Bent, A. F. (1998) Floral dip: a simplified method for *Agrobacterium*-mediated transformation of *Arabidopsis thaliana. Plant J.* 16, 735-743.
Counillon, L., et al., *Proc. Natl. Acad. Sci. USA,* 90:4508-4512 (1993).
Davies, J. M., et al., The Bioenergetics of Vacuolar $H^+$ Pumps. In: Leigh R. A.,
Sanders, D., (eds) The Plant Vacuole, pp. 340-363, Academic Press, San Diego (1997).
Drews, G., et al., *Plant Mol. Biol. Rep.,* 5:242-250 (1988).
Drozdowicz, Y. M. and Rea, P. A. (2001) Vacuolar $H^+$-pyrophosphatases: from evolutionary backwaters into mainstream. *Trends Plant Sci.* 6, 206-211.
Estelle, M. and Somerville, C. (1987) Auxin-resistant mutants of *Arabidopsis thaliana* with an altered morphology. *Mol. Gen. Genet.* 206, 200-206.
Gahoonia, T. S. and Nielsen, N. E. (2004) Root traits as tools for creating phosphorus efficient crop varieties. *Plant Soil,* 260, 47-57.
Gaxiola, R. A., et al., *EMBO J.,* 11:3157-3164 (1992).
Gaxiola, R. A., et al., *Proc. Natl. Acad. Sci. USA,* 95:4046-4050 (1998).
Gaxiola, R. A., et al., *Proc. Natl. Acad. Sci. USA,* 96:1480-1485 (1999).
Gaxiola, R. A., Li, J., Undurraga, S., Dang, L. M., Allen, G. J., Alper, S. L. and Fink, G. R. (2001) Drought- and salt-tolerant plants result from overexpression of the AVP1$H^+$-pump. *Proc. Natl. Acad. Sci. USA,* 98, 11 444-11 449.
Gaxiola, R. A., Palmgren, M. G. and Schumacher, K. (2007) Plant proton pumps. *FEBS Lett.* 581, 2204-2214.
Gibeaut, D. M., Hulett, J., Cramer, G. R. and Seemann, J. R. (1997) Maximal biomass of *Arabidopsis thaliana* using a simple, lowmaintenance hydroponic method and favorable environmental conditions. *Plant Physiol.* 115, 317-319.
Gietz, D., et al., Nucleic Acids Res., 20:1425 (1992).
Gilooly, J. F., Allen, A. P., Brown, J. H., Elser, J. J., Martinez del Rio, C., Savage, V. M., West, G. B., Woodruff, W. H. and Woods, H. A. (2005) The metabolic basis of whole-organism RNA and phosphorus content. *Proc. Natl. Acad. Sci. USA,* 102, 11 923-11 927.
Guiltinan, M. J., et al., *Meth. Cell Biol.,* 49:143-151 (1995).
Guthrie C. and Fink, G. R., Guide to Yeast Genetics and Molecular Biology (Academic, San Diego (1991).
Hammond, J. P., Broadley, M. R. and White, P. J. (2004) Genetic responses to phosphorus deficiency. *Ann. Bot.* 94, 323-332.
Hartel, H., Dormann, P. and Benning, C. (2000) DGD1-independent biosynthesis of extraplastidic galactolipids after phosphate deprivation in *Arabidopsis ? Proc. Natl. Acad. Sci. USA,* 97, 10 649-10 654.
Haughn, G. W. and Somerville, C., Mol. Gen. Genet., 204: 430-434 (1986).
Hechenberger, M., et al., *J. Biol. Chem.,* 271:33632-33638 (1996).
Hermans, C., Hammond, J. P., White, P. J. and Verbruggen, N. (2006) How do plants respond to nutrient shortage by biomass allocation? *Trends Plant Sci.* 11, 610-617.
Holford, I. C. R. (1997) Soil phosphorus: its measurements and its uptake by plants. *J. Soil Res.* 35, 227-239.
Hong, B., et al., *Plant Physiol.,* 119:1165-1175 (1999).

Jauh, G.-Y., et al., *Plant Cell,* 11:1867-1882 (1999).

Kausch, A. P., Adams, T. R. and Haines, G. (1995) Effects of microprojectile bombardment on embryogenic suspension cell cultures of maize (*Zea mays* L.) used for genetic transformation. *Planta,* 196, 501-509.

Kennedy, B. K., et al., *Cell,* 89:381-391 (1997).

Kieber, J. J., et al., *Cell,* 72:427-441 (1993).

Kim, Y., et al., *Plant Physiol.,* 106:375-382 (1994).

Kirsch, M., et al., *Plant Mol. Biol.,* 32:543-547 (1996).

Kochian, L., Hoekenga, O. A. and Pineros, M. A. (2004) How do crop plants tolerate acid soils? Mechanisms of aluminium tolerance and phosphorus efficiency. *Annu. Rev. Plant Biol.* 55, 459-493.

Krysan, P., et al., *Proc. Natl. Acad. Sci. USA,* 93:8145-8150 (1996).

Levi, M., et al., *Physiol. Plant.* 71:68-72 (1987).

Li, J., Yang, H., Peer, W. A., Richter, G., Blakeslee, J. J., Bandyopadhyay, A., Titapiwantakun, B., Undurraga, S., Khodakovskaya, M., Richards, E. L., Krizek, B. A., Murphy, A. S., Gilroy, S, and Gaxiola, R. A. (2005) *Arabidopsis* $H^+$-PPase AVP1 regulates auxin mediated organ development. *Science,* 310, 121-125.

Lerchl, J., et al., *Plant Molec. Biol.,* 29: 833-840 (1995).

Lopez-Bucio, J., Hernandez-Abreu, E., Sanchez-Calderon, L., Nieto-Jacobo, M. F., Simpson, J. and Herrera-Estrella, L. (2002) Phosphate availability alters architecture and causes changes in hormone sensitivity in the *Arabidopsis* root system. *Plant Physiol.* 129, 244-256.

Madhani, H. D., et al., *Cell,* 91:673-684 (1997).

Madrid, R., et al., *J. Biol. Chem.,* 273:14838-14844 (1998).

Maeshima M. (2000) Vacuolar $H^+$-pyrophosphatase. *Biochimica et Biophysica Acta* 1465, 37-51.

Marty, F., "The Biogenesis of Vacuoles: Insights from Microscopy. In: The Plant Vacuole, 1-42, Leigh, R. A. and Sanders, D., Academic Press, San Diego (1997).

McCormick, S., Transformation of tomato with *Agrobacterium tumefaciens*. In: Plant Tissue Culture Manual, pp. 1-9, Lindsey, K. (ed.), Kluwer Academic Publishers, Dordrecht, The Netherlands (1991).

McCusker, J. H., et al., *Mol. Cell. Biol.,* 7:4082-4088 (1987).

McSteen, P. and Leyser, O. (2005) Shoot branching. *Annu. Rev. Plant Biol.* 56, 353-374.

Misson, J., Raghothama, K. G., Jain, A., Jouhet, J., Block, M. A., Bligny, R., Ortet, P., Creff, A., Somerville, S., Rolland, N., Doumas, P., Nacry, P., Herrera-Estrella, L., Nussaume, L. and Thibaud, M.-C. (2005) A genome-wide transcriptional analysis using *Arabidopsis thaliana* Affymetrix gene chips determined plant responses to phosphate deprivation. *Proc. Natl. Acad. Sci. USA,* 102, 11 934-11 939.

Muchhal, U.S., Pardo, J. M. and Raghothama, K. G. (1996) Phosphate transporters from the higher plant *Arabidopsis thaliana. Proc. Natl. Acad. Sci. USA,* 93, 10 519-10 523.

Mullen, R. T., et al., *Plant. J.,* 12:313-322 (1997).

Murashige, T. and Skoog, F. (1962) A revised medium for rapid growth and bioassays with tobacco tissue culture. *Physiol. Plant.* 15, 473-497.

Murguia, J R., et al., *Science,* 267:232-234 (1995).

Murphy, A., Eisinger, W., Schaff, J., Kochian, L. and Taiz, L. (1999) Early copper-induced leakage of $K^+$ from *Arabidopsis* seedlings is mediated by ion channels and coupled to citrate efflux. *Plant Physiol.* 121, 1375-1382.

Murphy, J. and Riley, J. P. (1962) A modified single solution method for the determination of phosphate in natural waters. *Anal. Chim. Acta,* 27, 31-36.

Nass, R. and Rao, R., *J. Biol. Chem.,* 273:21054-21060 (1998).

Neuhaus, J. M., et al., *Plant Mol. Biol.,* 38:127-144 (1998).

Niyogi, K. K. and Fink, G. R., *Plant Cell,* 4:721-733 (1992).

Paris, N., et al., *Plant Physiol.,* 115:29-39 (1997).

Park, S., Li, J., Pittman, J. K., Berkowitz, G. A., Yang, H., Undurraga, S., Morris, J., Hirschi, K. D. and Gaxiola, R. A. (2005) Up-regulation of a $H^+$-pyrophosphatase ($H^+$-PPase) as a strategy to engineer drought-resistant crop plants. *Proc. Natl. Acad. Sci. USA,* 102, 18 830-18 835.

Poirier, Y. and Bucher, M. (2002) Phosphate transport and homeostasis in *Arabidopsis*. In: *The Arabidopsis Book*, pp. 1-35. Town: American Society of Plant Biologists.

Pringle, J., et al., in Immunofluorescence Methods for Yeast, eds. Guthrie, C. And Fink, G. F. (Academic, Sand Diego), Vol. 194 pp. 565-602 (1991).

Quesada, A., et al., *Plant Mol. Biol.,* 34:265-274 (1997).

Raghothama, K. G. (1999) Phosphate acquisition. *Annu. Rev. Plant Physiol. Plant Mol. Biol.* 50, 665-693.

Rate, et al., *The Plant Cell,* 11: 1695-1708 (1999).

Rea, P. A., et al., Tonoplast Adenosine Triphosphate and inorganic Pyrophosphatase. In: Methods Plant Biochem., pp. 385-405, Academic Press Limited, London (1990).

Rea, P. A., Kim, Y., Sarafian, V., Poole, R. J. and Davies, J.M.D.S. (1992) Vacuolar $H(^+)$-translocating pyrophosphatases: a new category of ion translocase. *Trends Biochem. Sci.* 17, 348-353.

Rodriguez-Navarro, A. and Ramos, J., *J. Bacteriol.,* 159:940-945 (1984).

Sanchez-Calderon, L., Lopez-Bucio, J., Chacon-Lopez, A., Gutierrez-Ortega, A., Hernandez-Abreu, E. and Herrera-Estrella, L. (2006) Characterization of low phosphorus insensitive mutants reveals a crosstalk between low phosphorus-induced determinate root development and activation of genes involved in the adaptation of *Arabidopsis* to phosphorus deficiency. *Plant Physiol.* 140, 879-889.

Sarafian, V. et al., *Proc. Natl. Acad. Sci., USA,* 89:1775-1779 (1992).

Sato, M. H., et al., *J. Biol. Chem.,* 272:24530-24535 (1997).

Schneider, B. L., et al., *Yeast,* 11: 1265-1274 (1995).

Schumaker, K. S. and Sze, H. (1985) A $Ca^{2+}/H^+$ antiport system driven by the proton electrochemical gradient of a tonoplast $H^+$-ATPase from oat roots. *Plant Physiol.* 79, 1111-1117.

Schwappach, B., et al., *J. Biol. Chem.,* 273:15110-15118 (1998).

Serrano, R., et al., *Crit. Rev. Plant Sci.,* 13:121-138 (1994).

Shen, H., Chen, J., Wang, Z., Yang, C., Sasaki, T., Yamamoto, Y., Matsumoto, H. and Yan, X. (2006) Root plasma membrane $H^+$-ATPase is involved in the adaptation of soybean to phosphorus starvation. *J. Exp. Bot.* 57, 1353-1362.

Sorin, A., et al, *J. Biol. Chem.,* 272:9895-9901 (1997).

Stitt, M., *Bot. Acta* 111:167-175 (1998).

Topfer, R., Matzeit, V., Gronenbom, B., Schell, J. and Steinbiss, H H. (1987) A set of plant expression vectors for transcriptional and translational fusions. *Nucleic Acids Res.* 15, 5890.

Tsiantis, M. S., et al., *Plant J.,* 9:729-736 (1996).

Vance, C. P., Uhde-Stone, C. and Allan, D. L. (2003) Phosphorus acquisition and use: critical adaptations by plants for securing a nonrenewable resource. *New Phytologist,* 157, 423-447.

Vitale, A. V., et al., *Trends Plant Sci.,* 4:148-154 (1999).

Ward, J., Reinders, A., Hsu, H. and Sze, H. (1992) Dissociation and reassembly of the vacuolar $H^+$-ATPase complex from oat roots. *Plant Physiol.* 99, 161-169.

Wu, S. J., et al., *Plant Cell,* 8:617-627 (1996).

Xiang, C., Han, P., Lutziger, I., Wang, K. and Oliver, D. J. (1999) A mini binary vector series for plant transformation. *Plant Mol. Biol.* 40, 711-717.

Xie, X. S., et al., *J. Biol. Chem.*, 264:18870-18873 (1989).

Yan, F., Zhu, Y., Muller, C., Zorb, C. and Schubert, S. (2002) Adaptation of H+-pumping and plasma membrane H+ ATPase activity in proteoid roots of white lupin under phosphate deficiency. *Plant Physiol.* 129, 50-63.

Yoshida, S., Formo, D. A., Cock, J. H. and Gomez, K. A. (1976) Laboratory Manual for Physiological Studies of Rice, 3rd edn. Manila: The International Rice Research Institute.

Zhen, R. G., et al., *Plant Physiol.*, 104:153-159 (1994).

Zhen, R. G., et al., "The Molecular and Biochemical Basis of Pyrophosphate-Energized Proton Translocation at the Vacuolar Membrane," Academic Press Limited (1997).

Zhen, R. G., Kim, E. J. and Rea, P. A. (1997) Acidic residues necessary for pyrophosphate-energized pumping and inhibition of the vacuolar H+-pyrophosphatase by N,N'-dicyclohexylcarbodiimide. *J. Biol. Chem.* 272, 22 340-22 348.

Zhu, Y., Yan, F., Zorb, C. and Schubert, S. (2005) A link between citrate and proton release by proteoid roots of white lupin (*Lupinus albus* L.) grown under phosphorus-deficient conditions. *Plant Cell Physiol.* 46, 892-901.

---

What is claimed is:

1. A method of making a transgenic plant with one or more enhanced phenotypic traits relative to non-transgenic wild-type plants of the same species, wherein the enhanced phenotypic traits are selected from the group consisting of increased tolerance to one or more salts, increased yield and larger plant size, said method comprising:

a) introducing an exogenous nucleic acid comprising a nucleic acid sequence encoding a plant vacuolar pyrophosphatase into one or more cells of a plant to produce transgenic plant cells, wherein the exogenous nucleic acid is operably linked to at least one regulatory element that causes over-expression of the plant vacuolar pyrophosphatase in the transgenic plant cells;

b) regenerating transgenic plants from the transgenic plant cells; and c) selecting a transgenic plant with one or more enhanced phenotypic traits relative to non-transgenic wild-type plants of the same species, wherein the enhanced phenotypic traits are selected from the group consisting of increased tolerance to one or more salts, increased yield, and larger plant size.

2. The method of claim 1, wherein the transgenic plant is selected from the group consisting of tomato, rice, tobacco, sorghum, cucumber, lettuce, turf grass, *Arabidopsis* and corn.

3. The method of claim 2, wherein the one or more cells of a plant are obtained from a tissue selected from the group consisting of roots, stems, leaves, flowers, fruits and seeds.

4. The method of claim 3, wherein the nucleic acid sequence encoding a plant vacuolar pyrophosphatase is from a non-transgenic wild-type plant of the same species as the transgenic plant.

5. The method of claim 3, wherein the nucleic acid sequence encoding a plant vacuolar pyrophosphatase is from a non-transgenic wild-type plant of a species different from the transgenic plant.

6. The method of claim 1, wherein the nucleic acid sequence encoding a plant vacuolar pyrophosphatase is obtained from a plant selected from the group consisting of *Arabidopsis*, tobacco, tomato and corn.

7. The method of claim 1, wherein the regulatory element is selected from the group consisting of tissue-specific promoters, constitutive promoters, inducible promoters and promoters that are both tissue-specific and inducible.

8. The method of claim 1, wherein the regulatory element comprises a double tandem enhancer of a 35S CaMV promoter.

9. The method of claim 1, wherein the plant vacuolar pyrophosphatase is *Arabidopsis* vacuolar pyrophosphatase AVP1 or a homolog thereof with vacuolar pyrophosphatase activity.

10. The method of claim 1, wherein the enhanced phenotypic trait is increased tolerance to one or more salts and the salts are selected from the group consisting of NaCl, KCl and $CaCl_2$.

11. The method of claim 10, wherein the one or more salts have a concentration of about 0.2M to about 0.3M in water.

12. A method of making a transgenic plant with enhanced phenotypic traits relative to non-transgenic wild-type plants of the same species grown under Pi-deficient growth conditions, wherein the enhanced phenotypic traits include a first enhanced phenotypic trait selected from the group consisting of increased yield and increased biomass and the enhanced phenotypic traits additionally include a second enhanced phenotypic trait selected from the group consisting of increased root structure, increased root and shoot biomass, delayed curtail of cell proliferation, increased Pi uptake, increased rhizosphere acidification, resistance to Al toxicity, increased organic acid exudates from root under Al stress, and increased root $K^+$ contents with or without Al stress, said method comprising:
   a) introducing an exogenous nucleic acid comprising a nucleic acid sequence encoding a plant vacuolar pyrophosphatase into one or more cells of a plant to produce transgenic plant cells, wherein the exogenous nucleic acid is operably linked to at least one regulatory element that causes over expression of the plant vacuolar pyrophosphatase in the transgenic plant cells;
   b) regenerating transgenic plants from the transgenic plant cells; and
   c) selecting a transgenic plant with said enhanced phenotypic traits relative to non-transgenic wild-type plants of the same species grown under Pi-deficient growth conditions.

13. The method of claim 12, wherein the transgenic plant is selected from the group consisting of tomato, rice, tobacco, sorghum, cucumber, lettuce, turf grass, *Arabidopsis* and corn.

14. The method of claim 13, wherein the one or more cells of a plant are obtained from a tissue selected from the group consisting of roots, stems, leaves, flowers, fruits and seeds.

15. The method of claim 14, wherein the nucleic acid sequence encoding a plant vacuolar pyrophosphatase is from a non-transgenic wild-type plant of the same species as the transgenic plant.

16. The method of claim 14, wherein the nucleic acid sequence encoding a plant vacuolar pyrophosphatase is from a non-transgenic wild-type plant of a species different from the transgenic plant.

17. The method of claim 12, wherein the nucleic acid sequence encoding a plant vacuolar pyrophosphatase is obtained from a plant selected from the group consisting of *Arabidopsis*, tobacco, tomato and corn.

18. The method of claim 12, wherein the regulatory element is selected from the group consisting of tissue-specific promoters, constitutive promoters, inducible promoters and promoters that are both tissue-specific and inducible.

19. The method of claim 12, wherein the regulatory element comprises a double tandem enhancer of a 35S CaMV promoter.

20. The method of claim 12, wherein the plant vacuolar pyrophosphatase is *Arabidopsis* vacuolar pyrophosphatase AVP1 or a homolog thereof with vacuolar pyrophosphatase activity.

21. A method of making a transgenic rice plant with enhanced phenotypic traits relative to non-transgenic wild-type rice plants, wherein the enhanced phenotypic traits include a first enhanced phenotypic trait selected from the group consisting of increased biomass and seed yield and a second enhanced phenotypic trait selected from the group consisting of more tillers, more panicles and increased P, Fe and Zn contents, said method comprising:
   a) introducing an exogenous nucleic acid comprising a nucleic acid sequence encoding a plant vacuolar pyrophosphatase into one or more cells of a rice plant to produce transgenic rice plant cells, wherein the exogenous nucleic acid is operably linked to at least one regulatory element that causes over expression of the plant vacuolar pyrophosphatase in the transgenic rice plant cells;
   b) regenerating transgenic rice plant from the transgenic rice plant cells; and
   c) selecting for a transgenic rice plant with said enhanced phenotypic traits relative to non-transgenic wild-type rice plants of the same species.

22. The method of claim 21, wherein the one or more cells of a rice plant are obtained from a tissue selected from the group consisting of roots, stems, leaves, flowers, fruits and seeds.

23. The method of claim 22, wherein the nucleic acid sequence encoding a plant vacuolar pyrophosphatase is from a non-transgenic wild-type rice plant.

24. The method of claim 22, wherein the nucleic acid sequence encoding a plant vacuolar pyrophosphatase is from a non-transgenic wild-type plant of a species different from the transgenic rice plant.

25. The method of claim 21, wherein the nucleic acid sequence encoding a plant vacuolar pyrophosphatase is obtained from a plant selected from the group consisting of *Arabidopsis*, tobacco, tomato and corn.

26. The method of claim 21, wherein the regulatory element is selected from the group consisting of tissue-specific promoters, constitutive promoters, inducible promoters and promoters that are both tissue-specific and inducible.

27. The method of claim 21, wherein the regulatory element comprises a double tandem enhancer of a 35S CaMV promoter.

28. The method of claim 21, wherein the plant vacuolar pyrophosphatase is *Arabidopsis* vacuolar pyrophosphatase AVP1 or a homolog thereof with vacuolar pyrophosphatase activity.

29. A method of making a transgenic plant with enhanced phenotypic traits including increased yield or increased biomass and enhanced Pi uptake relative to non-transgenic wild-type plants of the same species, said method comprising:
   a) introducing an exogenous nucleic acid comprising a nucleic acid sequence encoding a plant vacuolar pyrophosphatase into one or more cells of a plant to produce transgenic plant cells, wherein the exogenous nucleic acid is operably linked to at least one regulatory element that causes over-expression of the plant vacuolar pyrophosphatase in the transgenic plant cells;
   b) regenerating transgenic plants from the transgenic plant cells; and
   c) selecting a transgenic plant with said enhanced phenotypic traits relative to non-transgenic wild-type plants of the same species.

30. A transgenic progeny of a transgenic plant produced by the method of claim 1, wherein the transgenic progeny comprises said exogenous nucleic acid and having said enhanced phenotypic traits.

31. A seed produced by a transgenic plant produced by the method of claim 1 or produced by transgenic progeny of said transgenic plant, wherein the seed comprises said exogenous nucleic acid.

32. A transgenic progeny of a transgenic plant produced by the method of claim 12, wherein the transgenic progeny comprises said exogenous nucleic acid and having said enhanced phenotypic traits.

33. A seed produced by a transgenic plant produced by the method of claim 12 or produced by transgenic progeny of said transgenic plant, wherein the seed comprises said exogenous nucleic acid.

34. A transgenic progeny of a transgenic rice plant produced by the method of claim 21, wherein the transgenic rice progeny comprises said exogenous nucleic acid and having said enhanced phenotypic traits.

35. A seed produced by a transgenic rice plant produced by the method of claim 21 or produced by transgenic progeny of said transgenic rice plants, wherein the seed comprises said exogenous nucleic acid.

36. A transgenic progeny of a transgenic plant produced by the method of claim 29, wherein the transgenic progeny comprises said exogenous nucleic acid and having said enhanced phenotypic traits.

37. A seed produced by a transgenic plant produced by the method of claim 29 or produced by transgenic progeny of said transgenic plant, the seed comprises said exogenous nucleic acid.

\* \* \* \* \*